(12) United States Patent
Deng et al.

(10) Patent No.: US 12,180,509 B2
(45) Date of Patent: Dec. 31, 2024

(54) METHODS FOR REPROGRAMING NON-PLURIPOTENT CELLS INTO PLURIPOTENT STEM CELLS

(71) Applicants: Beihao Stem Cell and Regenerative Medicine Research Institute Co., Ltd., Guangdong (CN); Hong Guan Ltd., Beijing (CN)

(72) Inventors: Hongkui Deng, Beijing (CN); Yang Zhao, Beijing (CN); Ting Zhao, Beijing (CN); Jingyang Guan, Beijing (CN); Xu Zhang, Beijing (CN); Yao Fu, Beijing (CN); Junqing Ye, Beijing (CN)

(73) Assignees: BeiHao Stem Cell and Regenerative Medicine Research Institute Co., Ltd., Guangdong (CN); Hong Guan Ltd., Beijing (CN)

( * ) Notice: Subject to any disclaimer, the term of this patent is extended or adjusted under 35 U.S.C. 154(b) by 148 days.

(21) Appl. No.: 17/383,019

(22) Filed: Jul. 22, 2021

(65) Prior Publication Data

US 2022/0025321 A1 Jan. 27, 2022

Related U.S. Application Data

(62) Division of application No. 15/780,031, filed as application No. PCT/CN2015/095981 on Nov. 30, 2015, now abandoned.

(51) Int. Cl.
*C12N 5/0735* (2010.01)
*A61K 9/00* (2006.01)
*A61K 35/545* (2015.01)
*C12N 5/00* (2006.01)
*C12N 5/074* (2010.01)
*C12N 5/077* (2010.01)
*C12N 5/0775* (2010.01)

(52) U.S. Cl.
CPC .......... *C12N 5/0696* (2013.01); *A61K 9/0019* (2013.01); *A61K 35/545* (2013.01); *C12N 5/0018* (2013.01); *C12N 5/0606* (2013.01); *C12N 5/0656* (2013.01); *C12N 5/0667* (2013.01); *C12N 2501/01* (2013.01); *C12N 2501/06* (2013.01); *C12N 2501/115* (2013.01); *C12N 2501/15* (2013.01); *C12N 2501/385* (2013.01); *C12N 2501/415* (2013.01); *C12N 2501/602* (2013.01); *C12N 2501/604* (2013.01); *C12N 2501/606* (2013.01); *C12N 2501/727* (2013.01); *C12N 2501/73* (2013.01); *C12N 2501/999* (2013.01); *C12N 2506/1307* (2013.01); *C12N 2506/23* (2013.01)

(58) Field of Classification Search
None
See application file for complete search history.

(56) References Cited

U.S. PATENT DOCUMENTS 9,982,237 B2 * 5/2018 Deng .................. A61K 35/545
2012/0315703 A1   12/2012 Liu
2017/0275593 A1 * 9/2017 Hanna ................. C12N 5/0606

FOREIGN PATENT DOCUMENTS

| CN | 103380212 | 10/2013 |
| CN | 104278008 | 1/2015 |
| CN | 104673741 | 6/2015 |
| CN | 105039258 | 11/2015 |

OTHER PUBLICATIONS

Yao et al. PNAS 103(18):6907-6912, 2006 (Year: 2006).*
Extended European Search Report EP 15909460 mailed Apr. 10, 2019.
Hou, et al., "Pluripotent Stem Cells Induced form Mouse Somatic Cells by Small-Molecule Compounds", Science, 341(6146): 651-654 (2013).
International Search Report & Written Opinion PCT/CN2015/095981 mailed Sep. 5, 2016.
Masuda, et. al., "Chemically induced pluripotent stem cells (CiPSCs): a transgene-free approach", Journal of Molecular Cell Biology, 5(5): 354-355 (2013).
Yang, et al., "A XEN-like State Bridges Somatic Cells to Pluripotency during Chemical Reprogramming", Cell, 163(7): 1678-1691 (2015).
Zhou, "Generation of Induced Pluripotent Stem Cells Using Recombinant Proteins", Cell Stem Cell, 4:381-384 (2009).

* cited by examiner

*Primary Examiner* — Marcia S Noble
(74) *Attorney, Agent, or Firm* — PABST PATENT GROUP LLP

(57) ABSTRACT

Provided are chemical inducers of pluripotency (CIP) which include glycogen synthase kinase inhibitors, TGFβ receptor inhibitors, cyclic AMP agonists and S-adenosylhomocysteine hydrolase (SAH) inhibitors or histone acetylators. A method of inducing pluripotency in a partially or completely differentiated cell by using such chemical inducers of pluripotency is also provided. The method includes: (i) contacting a cell with the CIPs for a sufficient period of time to result in reprograming the cell into a pluripotent stem cell having ESC-like characteristics (CiPSC). Isolated chemically induced pluripotent stem cells (CiPSCs) and their progeny, produced by inducing differentiation of the CiPSCs, can be used in a number of applications, including but not limited to cell therapy and tissue engineering.

20 Claims, 51 Drawing Sheets

Specification includes a Sequence Listing.

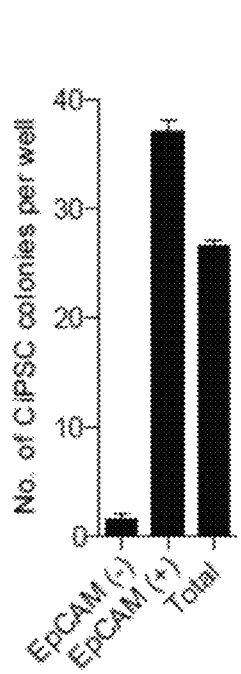 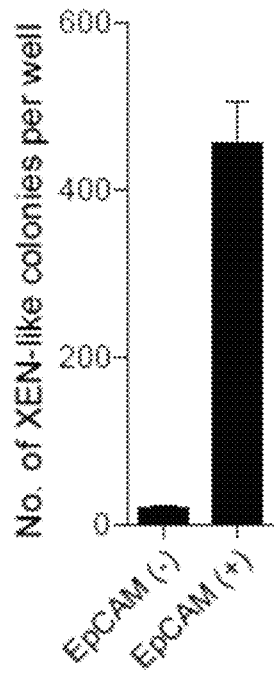
FIG. 16C
FIG. 16D
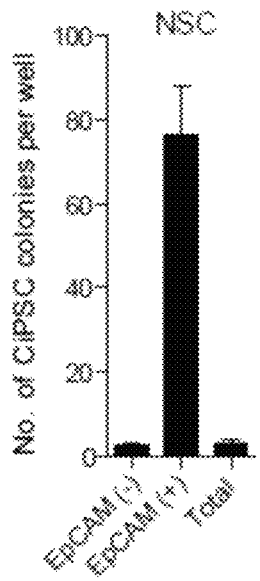 
FIG. 16E

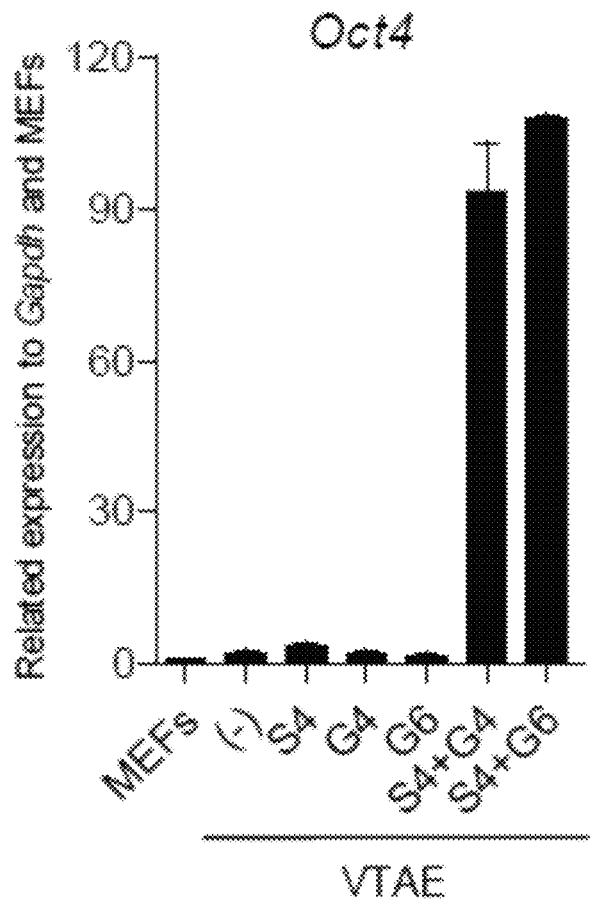
FIG. 21J
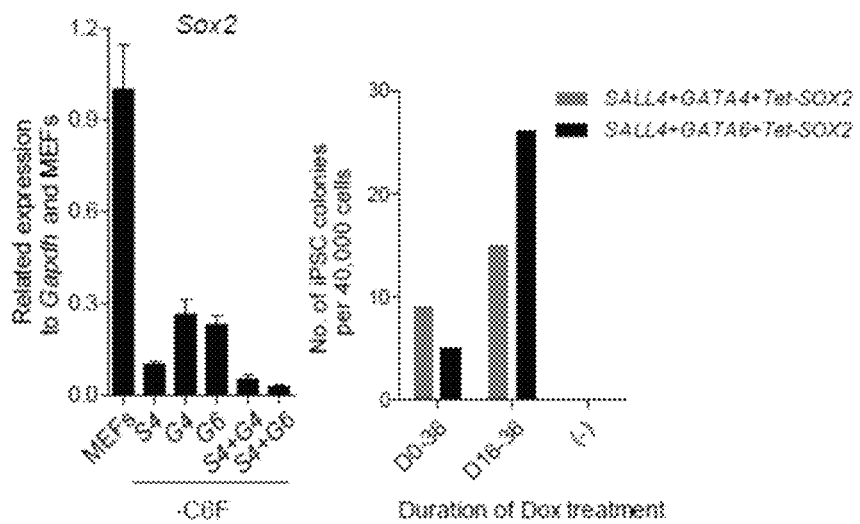
FIG. 21K
FIG. 21L

METHODS FOR REPROGRAMING NON-PLURIPOTENT CELLS INTO PLURIPOTENT STEM CELLS

CROSS REFERENCE TO RELATED APPLICATIONS

This application is divisional of U.S. application Ser. No. 15/780,031, filed May 30, 2018, which is a National Phase Application under 35 U.S.C. § 371 of PCT/CN2015/095981, filed Nov. 30, 2015, which are incorporated by references in their entirety.

REFERENCE TO SEQUENCE LISTING

The Sequence Listing submitted Oct. 11, 2021, as a text file named "HGL_101_DIV_ST25.txt," created on Nov. 6, 2018, and having a size of 16,949 bytes is hereby incorporated by reference.

FIELD OF THE INVENTION

The present invention generally relates to small molecule compositions and methods for reprograming eukaryotic cells into pluripotent cells.

BACKGROUND OF THE INVENTION

Pluripotent stem cells, such as embryonic stem cells (ESCs), can self-renew and differentiate into all somatic cell types. Somatic cells have been reprogrammed to become pluripotent via nuclear transfer into oocytes or through the ectopic expression of defined factors (Wilmut, et al., *Nature*, 385:810-813 (1997); Takahashi, et al., *Cell*, 126:663-676 (2006); Yamanaka, et al., *Nature*, 465:704-712 (2010) and Stadtfeld, et al., *Genes Dev.*, 24:2239-2263 (2010)). However, exogenous pluripotency-associated factors, especially Oct4, are indispensable in these methods for establishing pluripotency (Zhu, *Annu. Rev. Biomed. Eng.*, 13:73-90 (2011); Li, *Cell Res.*, 21:196-204 (2011) and Li, et al., *Proc. Natl. Acad. Sci. U.S.A.*, 109:20853-20858 (2012)). Additionally, the requirement for tumorigenic genes like c-Myc in these reprograming methods creates a risk of inducing cancerous cells. Accordingly, reprogramming strategies have raised concerns regarding the clinical applications (Saha, et al., *Cell Stem Cell*, 5:584-595 (2009) and Wu, et al., *Cell Biol.*, 13:497-505 (2011)).

Small molecules which can drive reprograming of somatic cells into pluripotent cells are disclosed in PCT/CN2014/081961. Small molecules have advantages because small molecules more readily penetrate the cells, they are nonimmunogenic, more cost-effective, and more easily synthesized, preserved, and standardized. There is still a need for a method of chemically reprograming non-pluripotent cells into pluripotent cells, that increases the efficiency of reprogramming, for example, by reducing to total reprograming time and/or increasing the number of reprogrammed cells obtained for the same length of time.

It is an object of the present invention to provide a combination of small molecules which can be used to reprogram partially or completely differentiated cells into pluripotent cells.

It is also an object of the present invention to provide a method of reprogramming partially or completely differentiated cells into pluripotent cells with improved efficiency.

SUMMARY OF THE INVENTION

Compositions and methods are disclosed for improving the efficiency of chemically inducing non-pluripotent cells into pluripotent cells. The methods are based on the discovery of an intermediate population of cells (XEN-like cells) during the reprogramming period, which are primed for conversion into pluripotency, small molecule combinations that preferentially bias partially or completely differentiated cells into a XEN-like state and subsequently reprogram the XEN-like cells into pluripotent cells, and the required replating concentration/density. Thus, by selecting small molecules which bias/enrich the conversion of partially or completely differentiated cells into a XEN-like state, small molecules which reprogram the XEN-like cells into pluripotent cells, and the appropriate replating concentration, the efficiency of reprograming partially or completely differentiated cells is enhanced in terms of number of colonies obtained and reprogramming time.

Accordingly, small molecule cocktails have been identified which can be used to enhance reprogramming of partially or completely differentiated cells (including cells that are not genetically engineered to express one or more markers of pluripotency such as Oct4, and which do not naturally express Oct4), into a XEN-like state and subsequently, into pluripotent cells. The required chemical inducers of pluripotency (CIPs) include (1) a glycogen synthase kinase (GSK) inhibitor, (2) a TGFβ receptor inhibitor, (3) a cyclic AMP agonist, (4) a S-adenosylhomocysteine hydrolase (SAH) inhibitor, (5) a histone acetylator/deacetylase inhibitor such as valproic acid (VPA; "V"), (6) a DOT1L methyltransferase inhibitor, (7) a retinoic acid receptor (RAR) agonist, (8) an epigenetic modulator, (9) an inhibitor of histone demethylation and combinations thereof. The CIPs may be provided separately or in combination as a CIP composition. One or more epigenetic modulators and retinoic acid receptor agonists, for example, retinoic receptor ligands may also be administered with the CIPs. In some preferred embodiments, the CIPs include DZNep as an SAH inhibitor.

In a preferred embodiment, the GSK inhibitor is the aminopyrimidine, CHIR99021 (CHIR; "C") [6-[[2-[[4-(2,4-Dichlorophenyl)-5-(5-methyl-1H-imidazol-2-yl)-2-pyrimidinyl]amino]ethyl]amino]-3-pyridinecarbonitrile]; the TGFβ receptor inhibitor is 616452 ("6") [2-(3-(6-Methylpyridin-2-yl)-1H-pyrazol-4-yl)-1,5-naphthyridine]; the cAMP agonist is Forskolin (FSK: "F") and the SAH inhibitor is 3-deazaneplanocin A (DZNep; "Z"). Preferred methyltransferase inhibitors include SGC 0946 ("S") (1-[3-[[[(2R,3S,4R,5R)-5-(4-Amino-5-bromo-7H-pyrrolo[2,3-d]pyrimidin-7-yl)-3,4-dihydroxytetrahydrofuran-2-yl]methyl](isopropyl)amino]propyl]-3-[4-(2,2-dimethylethyl)phenyl]urea) and EPZ004777, "1-(3-((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea ("E"). A preferred RAR agonists include AM 580 ("A") (4-[(5,6,7,8-Tetrahydro-5,5,8,8-tetramethyl-2-naphthalenyl)carboxamido]benzoic acid). A preferred inhibitor of histone demethylation is tranylcypromine ("T"). A preferred epigenetic modulator is 5-azacytidine ("D").

Also provided is a method of enhancing reprograming of a cell of a first type which is not a pluripotent cell, such as a somatic cell, into a pluripotent cell. Preferred cells to reprogram include fibroblast cells, adipose-derived stem cells (ADSC), neural derived stem cells and intestinal epithelial cells. In a preferred embodiment the method does not include transfecting the cell to be reprogrammed so that it expresses any of Oct4, KLF4, SOX2, C-Myc or NANOG. In this embodiment, the method also does not include contacting the cell to be reprogrammed with a polypeptide such as a transcription factors. The method disclosed herein includes the steps of (a) contacting the cell to be reprogrammed with a first cocktail of CIPs (herein, XEN-Cocktail) for a sufficient period of time to bias the cells into a XEN-like cell population; (b) contacting the population of XEN-like cells for a sufficient period of time to reprogram the cell into a chemically induced pluripotent stem cell (CiPSC) with a second cocktail of CIPS (herein, XEN-CiPSC cocktail) and (c) culturing the cells in 2i-medium. The cells are preferably replating during step (a) at a density of about 50,000-100,000 cells per well in a 6-well plate. The 2i-medium preferably additionally includes N2B27. The method optionally includes selecting for EpCAM (Epithelial cell adhesion molecule)-positive cells after step (a). The reprogrammed cell is identified as a pluripotent cell based on ESC-like properties such as morphology, doubling time, expression of ESC markers such as alkaline phosphatase (AP), nanog, Rex1, Sox2, Dax1, Sall4, undifferentiated embryonic cell transcription factor (Utf1), stage specific embryonic antigen-4 (SSEA-4), and the ability of the cell to differentiate into tissues of the three embryonic germ layers. The CiPSCs are isolated and can be further cultured.

Isolated chemically induced pluripotent stem cells (CiPSCs), are not naturally occurring pluripotent stem cells. CiPSCs possess ESC-like properties such as ESC morphology, doubling time similar to ESC, expression of ESC markers such as alkaline phosphatase (AP), nanog, Rex1, Sox2, Dax1, Sall4, undifferentiated embryonic cell transcription factor (Utf1), stage specific embryonic antigen-4 (SSEA-4), and the ability of the cell to differentiate into tissues of the three embryonic germ layers. CiPSCs are different from ESCs for example, in that they are not directly derived/isolated from the inner cell mass of a blastocyst. CiPSCs are different from other induced pluripotent stem cells (iPSC) in that they are not engineered to express a transgene such as genes expressing Oct4, KLF4, SOX2, c-Myc or NANOG, or are not produced by a process that includes transfecting the cells from which they obtained to express any of these transgenes. CiPSCs are also different from other induced pluripotent stem cells (iPSC) in that they are not produced by a process that includes contacting non-pluripotent cells with one or more polypeptides such as K1f, Oct, Myc or Sox. In a preferred embodiment, the CiPSCs are not genetically engineered, i.e., the CiPSCs are not altered by introducing or removing genetic elements from the cells. There is no obvious difference among CiPSCs, iPSCs and ESCs. However, CiPSCs disclosed herein can be distinguished from ESC at least by the methods that are used to generate them i.e., by their origin. Where ESC are naturally occurring cells, CiPSCs on the other hand are not naturally occurring and are obtained by treating non-pluripotent cells with a combination of small molecules, as described herein.

The CiPSCs can be cultured or induced to differentiate into cells of a desired type. The CiPSCs and their progeny can be used in a number of applications, including but not limited to cell therapy and tissue engineering.

BRIEF DESCRIPTION OF THE DRAWINGS

FIGS. 5A-G show the number of colonies of CiPSC cells as a function of the concentrations of small molecules as indicated (titrated during CiPSC induction). FIG. 5H shows Durations of each small molecule. FIGS. 5I-K show durations of the chemical combinations. The chemical reprogramming medium plus VC6TFZ was replaced with 2i-medium at different time points. Error bars indicate the s.d. (n≥2).

FIG. 6A shows validated small molecules improving chemical reprogramming efficiency in combination with VC6TFZ in MEFs. Chemicals added from day 0 to day 12: PGE2, DY131, RG108, 2-Me-5HT and IBMX; chemicals added after day 12: SF1670, UNC0638 and SRT1720. (−) control, DMSO. Error bars indicate the s.d. (n≥2). FIG. 6B shows the effect of TTNPB on improving chemical reprogramming efficiency in combination with C6FZ or VC6TFZ in MEFs. CiPSC colonies were quantified on day 50 and day 40 for chemical reprogramming by C6FZ and VC6TFZ, respectively. iPSC colonies were quantified on day 24 and day 16 for OSK- and OSKM-induced reprogramming, respectively. Error bars indicate s.d. (n=3). FIG. 6C shows the effect of TTNPB on improving chemical reprogramming kinetics in combination with VC6TFZ in MEFs. GFP-positive colonies were quantified on the indicated days. (−) control, VC6TFZ. Error bars indicate s.d. (n=3). FIGS. 6D-F show Genomic PCR analysis for CiPSCs.

FIGS. 7A and B shows genomic PCR for two sets of viral vectors used. FIG. 7C is a southern blot analysis to detect viral integration events. DNA probe was designed on psi sequence to target both pLL3.7-ΔU6 and tet-on vectors. CiPSCs were analyzed and Tet-O-iPS, pLL-O-iPS and MEFS were used as controls. FIG. 7D shows the ethidium-bromide stained gel used for the southern blot.

FIGS. 9B-D show RT-PCR analysis of pluripotency markers in MAF-CiPS cells, ADSC-CiPSC and MNF-CiPSCs.

FIGS. 11E-F shows the effects of individual and combined chemicals on the expression of Sall4 and Sox2 on day 12. FIG. 11G-H show the effects of removing chemicals from VC6TF on the expression of Sall4 and Sox2 on day 12. FIG. 11I shows the effects of withdrawing individual chemicals (CHIR, 616452 and FSK) from VC6TFZ on the expression of the pluripotency marker genes on day 32.

FIG. 13A shows relative expression changes of Sall4, Gata6 and Gata4 by Sall4, Gata6 or Gata4 knockdown. FIG. 13B shows relative expression changes of Sox17, Sall4, Gata6, Gata4 and Oct4 by Sox17 knockdown. FIG. 13C shows relative expression changes of Sox17 by the knockdown of Sall4, Gata6 or Gata4. FIG. 13D shows relative expression changes of Sox2 by the knockdown of Sall4, Gata6 or Gata4. Error bars indicate the s.d. (n=2). FIG. 13E shows Oct4 expression change by Sall4, Gata6 or Gata4 knockdown on day 32. Error bars indicate the s.d. (n=2). FIG. 13F shows numbers of GFP-positive and iPSC colonies when Sall4, Gata6 or Gata4 was knockdown during chemical reprogramming. Error bars indicate the s.d. (n=3).

FIG. 14A shows the relative ratios of intracellular levels SAH to SAM compared to that in MEFs as measured by HPLC analysis. Error bars indicate the s.d. (n=2). FIG. 14B shows the use of replacement of DZNep by SAH hydrolase inhibitors (Nep A, Adox and DZA) in combination with VC6TF treatment to induce CiPSC generation. Error bars indicate the s.d. (n=3). Abbreviations: HPLC (high-performance liquid chromatography).

15G shows mRNA levels of Sall4, Gata4, Gata6 and Sox17 genes detected by RNA-seq analysis in MEFs, IECs and NSCs.

Figure 16A:
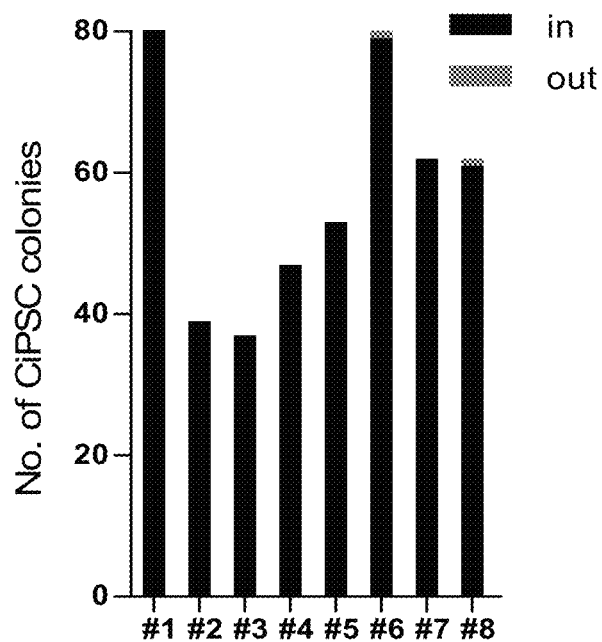
Figure 16B:
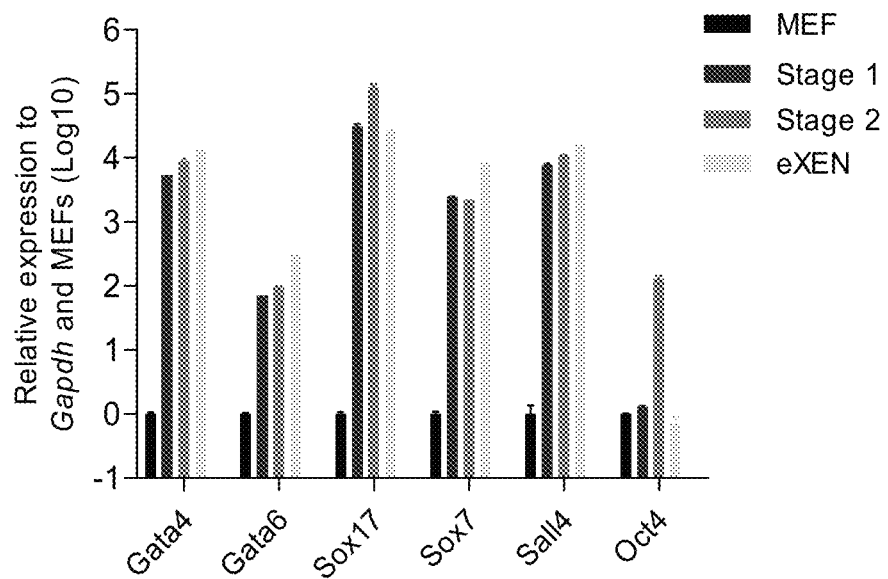

FIG. 16A shows numbers of CiPSC colonies generated from the inside (blue) and outside (red) of epithelial colonies in 8 batches of experiments. For experiments #5 and #7, the cell confluence of epithelial colonies was less than 20%. FIG. 16B shows qRT-PCR analysis of XEN cell markers (Gata4, Gata6, Sox17, Sox7, Sall4) and pluripotency marker Oct4 in MEFs, cells at the end of stage 1 (day 16) and stage 2 (day28) and eXEN (embryo-derived XEN cells). FIG. 16C shows CiPSC colony numbers generated at the end of stage 3 from EpCAM-negative (−), EpCAM-positive (+) and total cell populations sorted at day 20 (in stage 2 of chemical reprogramming). FIG. 16D shows XEN-like colony numbers at day 16 generated from EpCAM positive (+), negative (−) populations and total cells after FACS sorting at day 12 (in stage 1 of chemical reprogramming). Error bars indicate the SD (n≥2). FIG. 16E shows CiPSC colony numbers induced from neural stem cells (NSC, left) from indicated populations and intestinal epithelium cells (IEC, right). EpCAM negative (−), positive (+) and total populations were sorted by FACS at day 13 (for IECs) and day 20 (for NSCs), respectively.

Figure 17A:
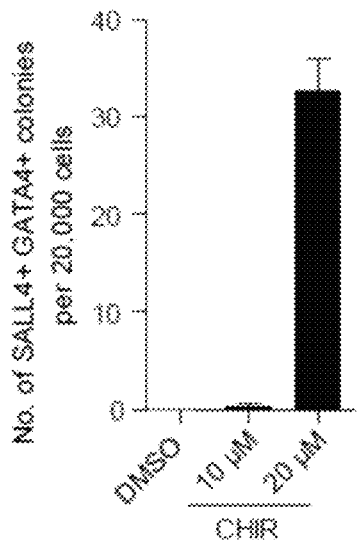
Figure 17B:
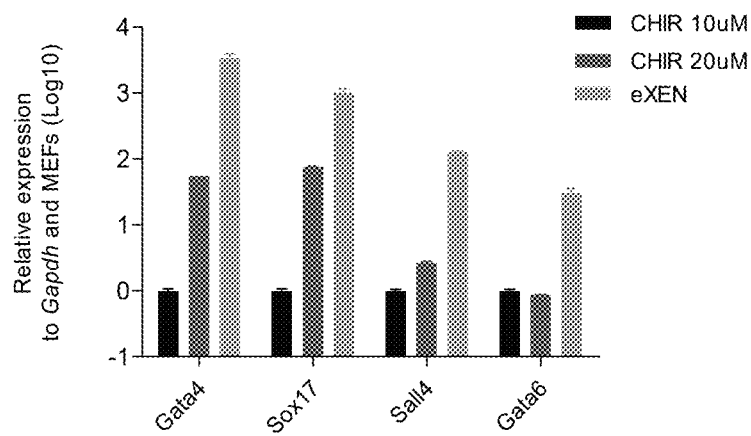
Figure 17C:
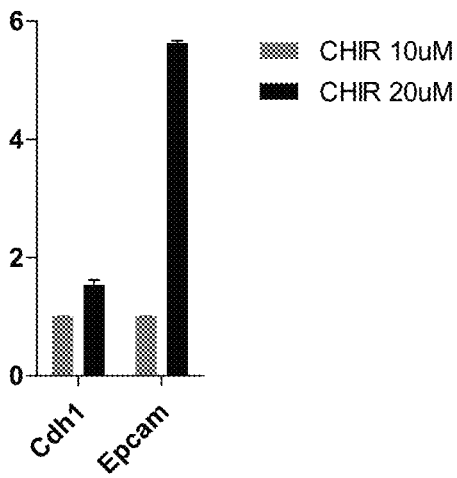
Figure 17D:
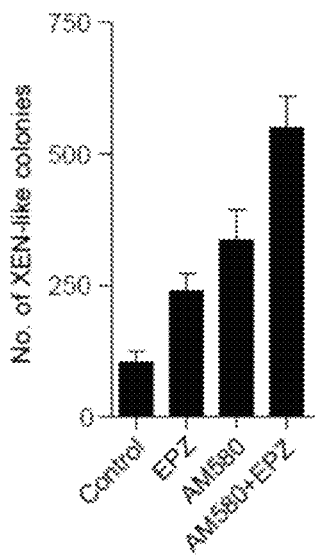
Figure 17E:
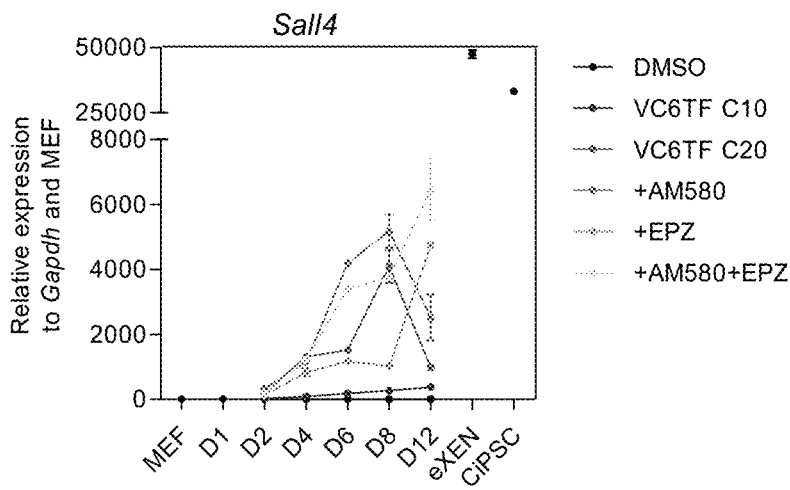
Figure 17F:
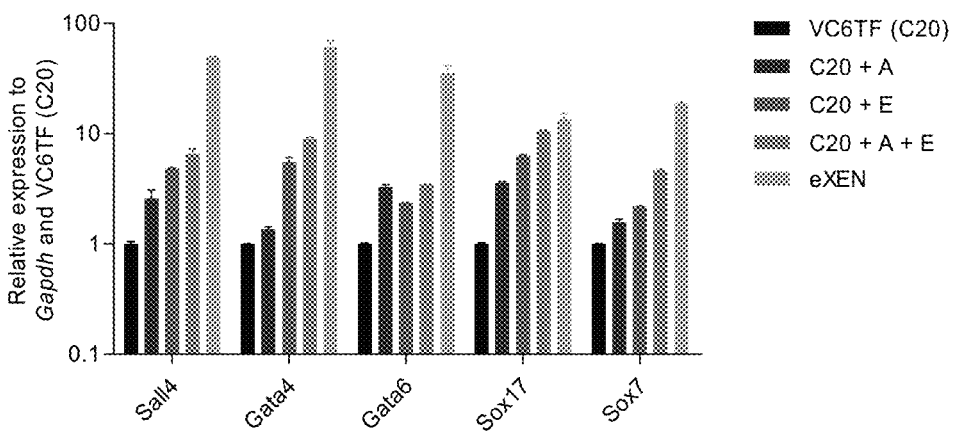
Figure 17G:
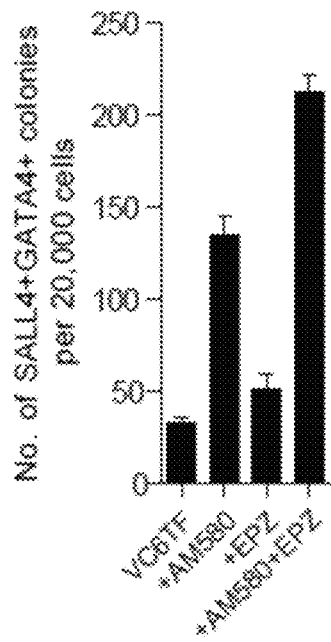
Figure 17H:
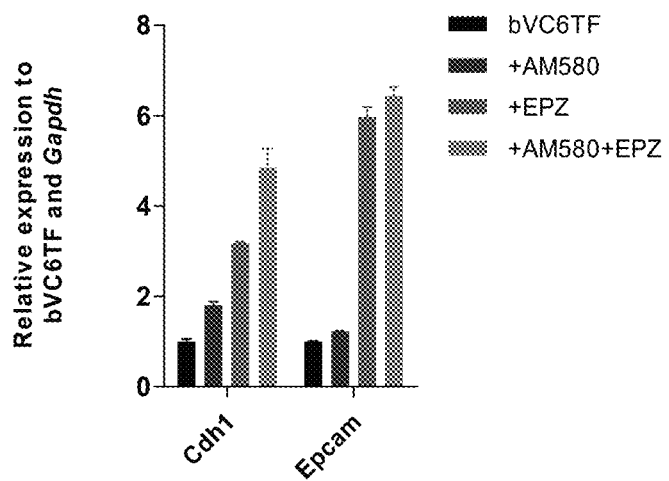
Figure 17I:
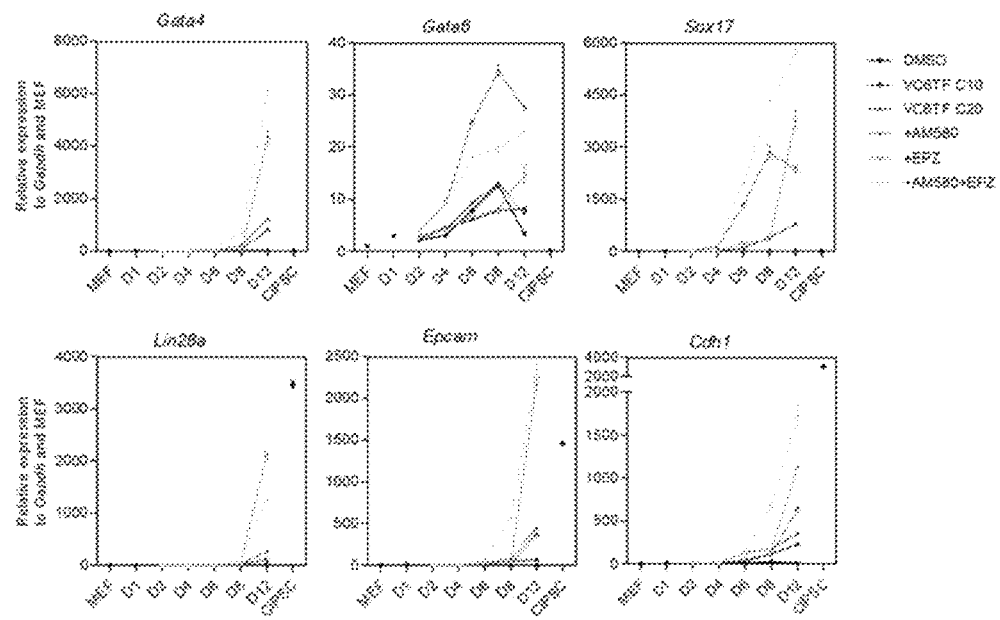
Figure 18A:
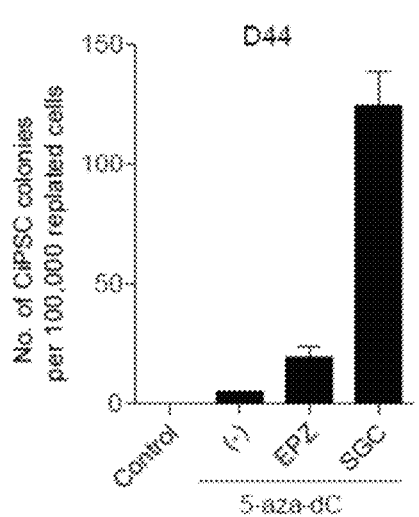
Figure 18B:
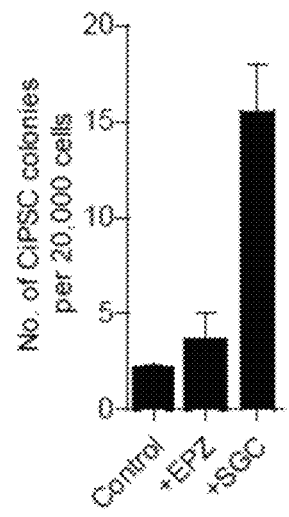
Figure 18C:
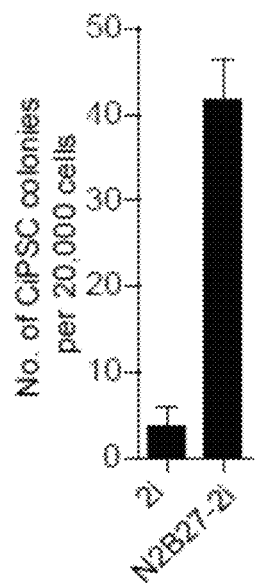
Figure 18D:
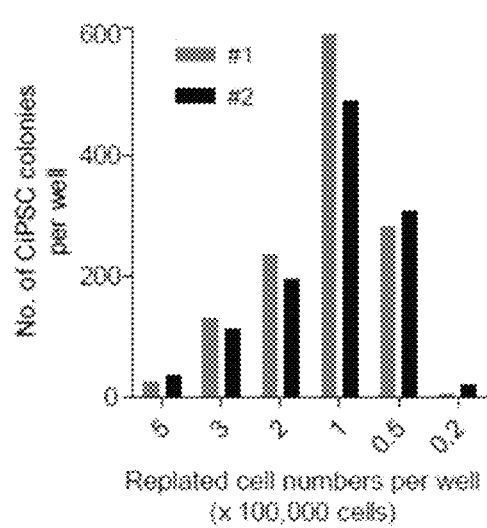
Figure 18E:
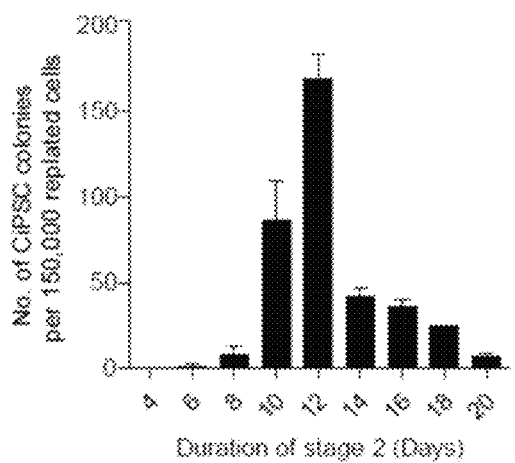
Figure 18F:
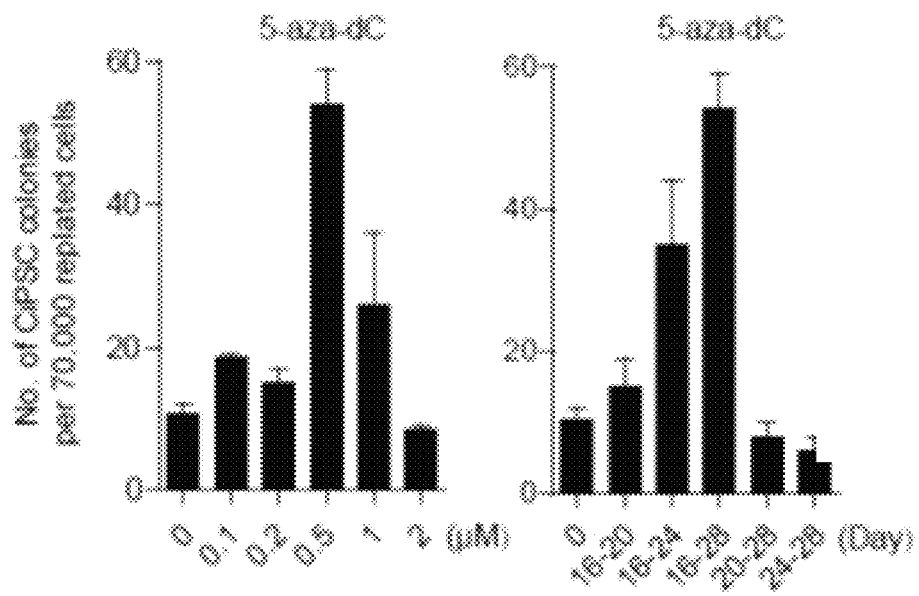
Figure 18G:
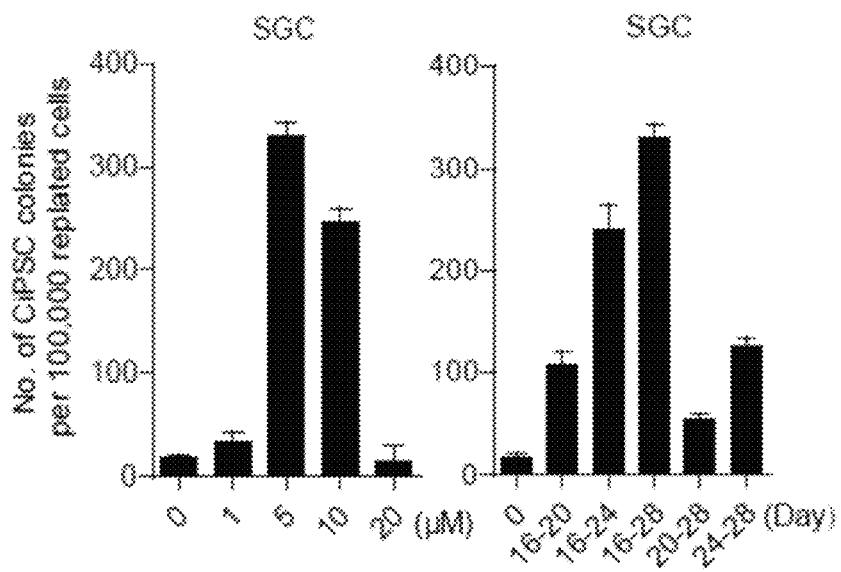
Figure 18H:
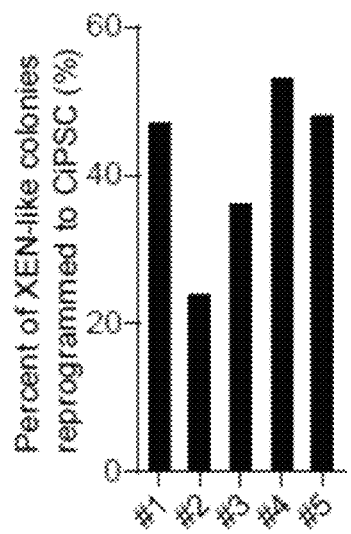
Figure 18I:
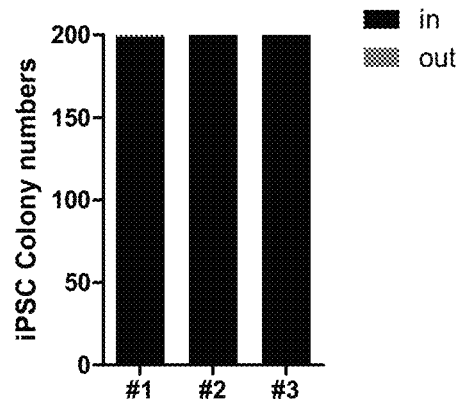

FIG. 17A shows numbers of SALL4 and GATA4 double-positive colonies after treatment with DMSO and VC6TF (CHIR, 10 UM and 20 µM) for 12 days. FIG. 17B shows qRT-PCR analysis of XEN cell markers (Gata4, Gata6, Sox17, Sall4) expression after treatment with VC6TF (CHIR, 10 UM and 20 UM) for 12 days. eXEN was set as a positive control. FIG. 17C shows qRT-PCR analysis of MET markers (EpCAM, Cdh1) expression after treatment of VC6TF (CHIR, 10 UM and 20 µM) for 12 days. FIG. 17D shows numbers and phase images of XEN-like colonies after treatment with control cocktail (VC6TF with CHIR, 20 µM) and that with additional small molecule EPZ004777 (E) and AM580 (A) for 16 days. Cells were re-plated at day 12 by 1:2. FIG. 17E shows qRT-PCR analysis of Sall4 expression in cells treated with different small-molecule cocktails during stage 1. FIG. 17F shows qRT-PCR analysis of XEN cell markers (Gata4, Gata6, Sox17, Sox7 and Sall4) expression induced with VC6TF (CHIR, 20 µM) and AM580 (A), EPZ004777 (E) or A plus E for 12 days. eXEN was set as a positive control. FIG. 17G shows numbers of SALL4 and GATA4 double-positive colonies after treatment with VC6TF (CHIR, 20 µM), and that with AM580, EPZ004777 (EPZ) and with their combination for 12 days. FIG. 17H shows qRT-PCR analysis of MET markers (Cdh1, EpCAM) expression after treatment with VC6TF (CHIR, 20 µM) and that with AM580 (A), EPZ004777 (E) and A plus E for 12 days. FIG. 17I shows qRT-PCR analysis of Gata4, Gata6, Sox17, Lin28a, EpCAM and Cdh1 expression in cells treated by different small molecule cocktails during stage 1. eXEN and CiPSCs were set as controls. Error bars indicate the SD (n≥2). FIG. 18A shows numbers of CiPSC colonies at day 44 induced with a control cocktail (VC6TFZ) and with 5-aza-dC, 5-aza-dC plus EPZ004777 (EPZ) or SGC0946 (SGC) in stage 2 of 12 days. FIGS. 18B and C show number of CiPSC colonies with treatment of control (VC6TFZ) and with EPZ004777 (EPZ) or SGC0946 (SGC) in stage 2 and numbers of CiPSC colonies in 2i-medium with different components in stage 3. FIG. 18D shows Numbers of CiPSC colonies at the end of reprogramming from different densities of cells in each well (6-well plate) re-plated at day 12. #1 and #2 were two independent experiments. FIG. 18E shows Numbers of CiPSC colonies at the end of reprogramming, with a different time course in stage 2. Error bars indicate the SD (n≥3). FIG. 18F shows the effect of the concentration (left) and duration (right) of 5-aza-dC. 5-aza-dC added in stage 2. FIG. 18G shows the effect the concentration (left) and duration (right) of SGC0946 (SGC). SGC was added in stage 2. FIG. 18H shows percentage of XEN-like colonies that reprogrammed to CiPSC colonies at day 40 by new protocol in 5 batches of experiments. FIG. 18I shows numbers of CiPSC colonies generated inside (blue) and outside (red) XEN-like colonies by new protocol in 3 batches of experiments. Error bars indicate the SD (n≥2).

Figure 19A:
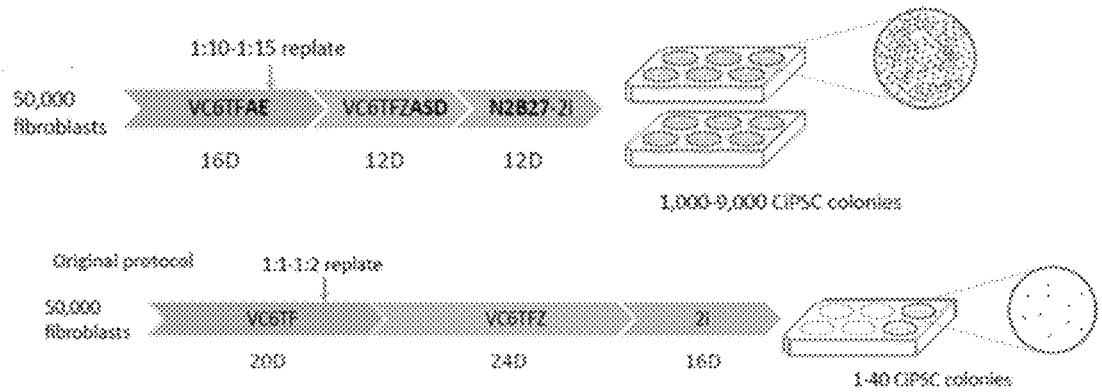
Figure 19B:
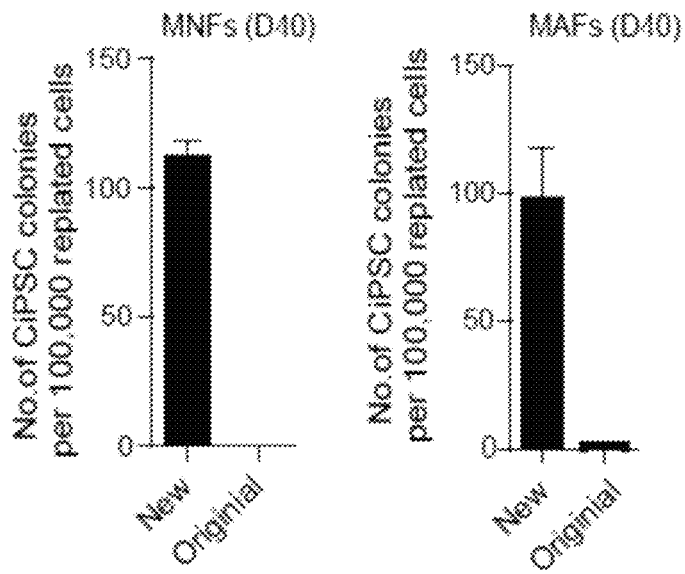
Figure 19C:
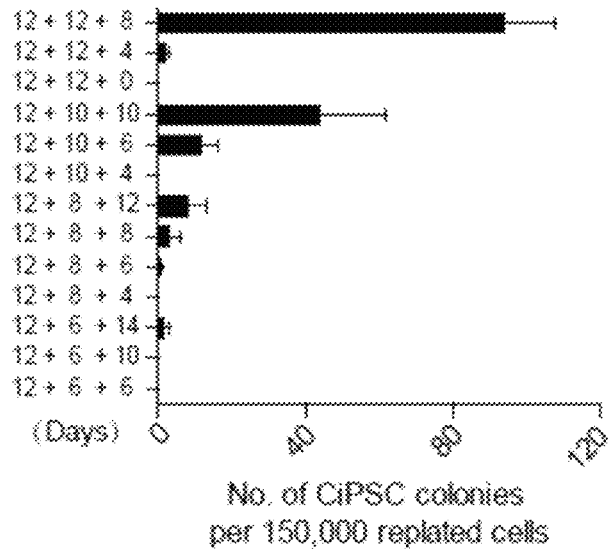
Figure 19D:
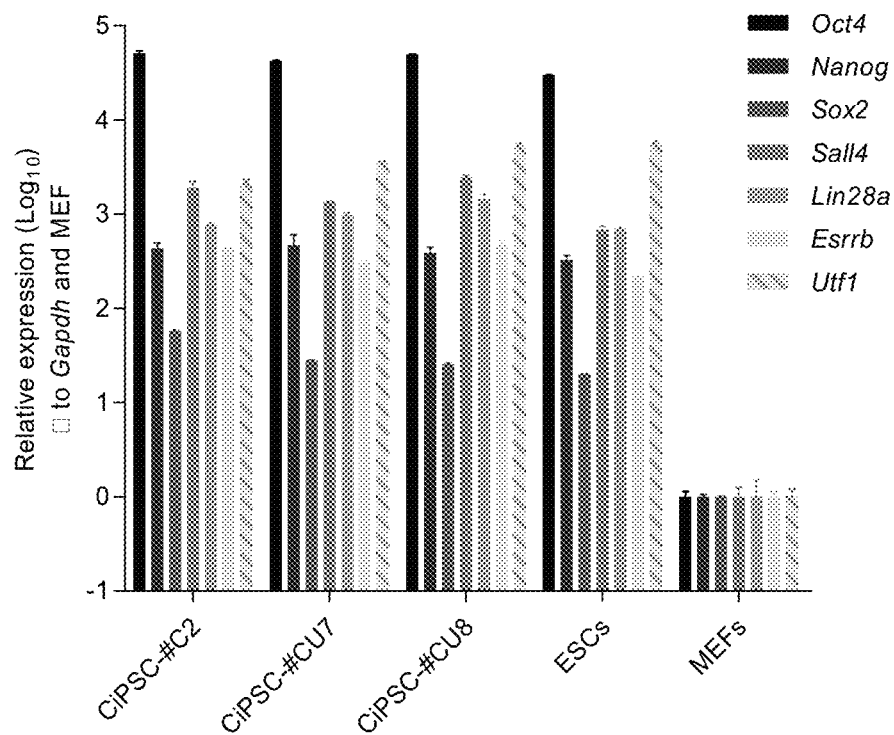

FIG. 19A is a schematic comparison of the new protocol in this study and the protocol disclosed in Hou et al., 2013 . . . . In total, 1-40 CiPSC colonies (in 2 wells) were induced from initial 50,000 fibroblasts in a 60-day induction using the initial protocol. Whereas 1,000-9,000 CiPSC colonies (in 10-15 wells) were obtained from initial 50,000 fibroblasts after 40 days of small-molecule treatment by using the new protocol. FIG. 19B is a comparison of the previously described protocol (no XEN-like state bias) and the protocol which takes advantage of the CEN-like state, in primary CiPSC colony numbers (day 40) induced from mouse neonatal fibroblasts (MNFs, left) and mouse adult fibroblasts (MAFs, right), respectively. FIG. 19C shows Numbers of CiPSC colonies generated under shortened durations for each stage. For example, "12+10+6" represents a sequential duration of 12 days for stage 1, 10 days for stage 2, and 6 days for stage 3. The minimal time course required for CiPSC induction was 26 days (12+8+6), by which one CiPSC colony was obtained. FIG. 19D shows Pluripotency marker expression in CiPSC colonies induced by the new protocol, analyzed by qRT-PCR.

Figure 20A:
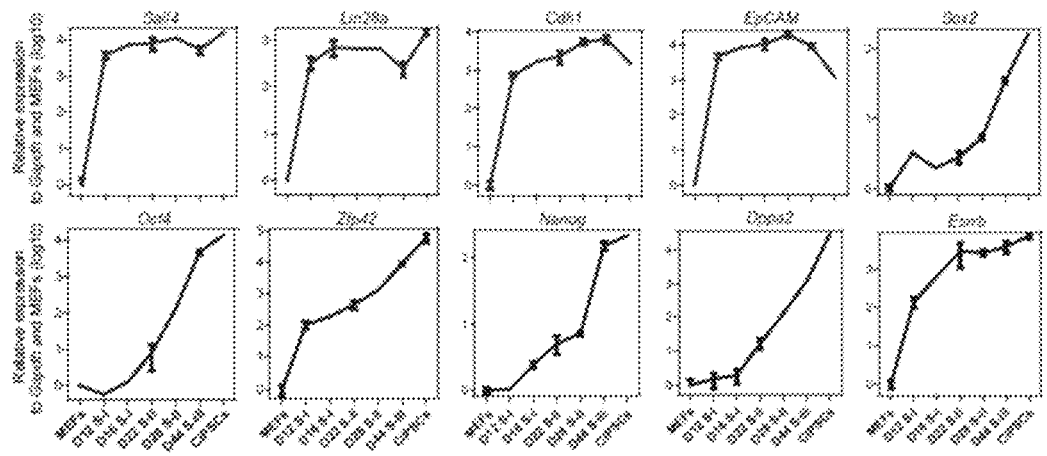
Figure 20B:
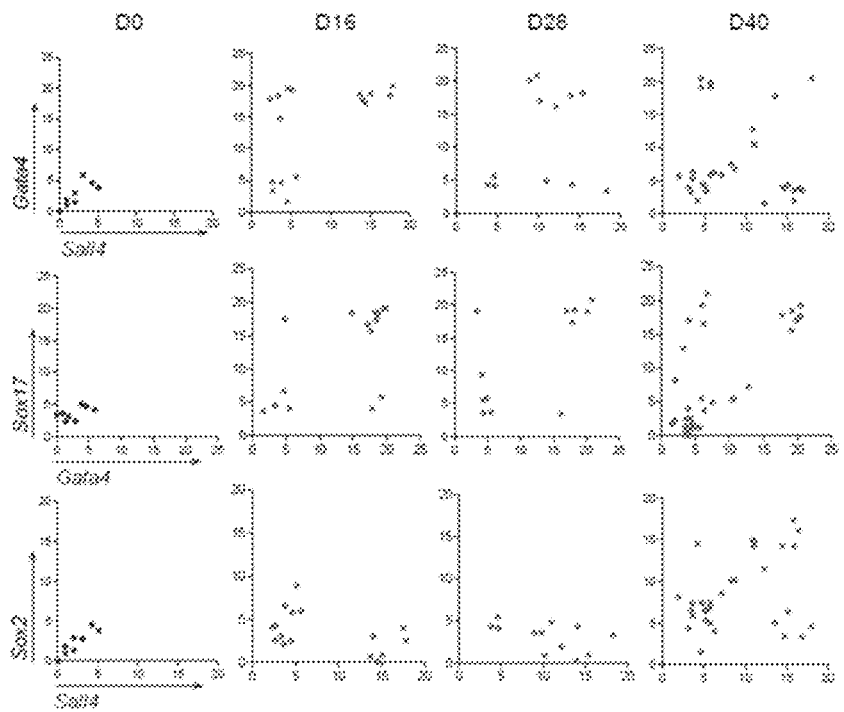
Figure 20C:
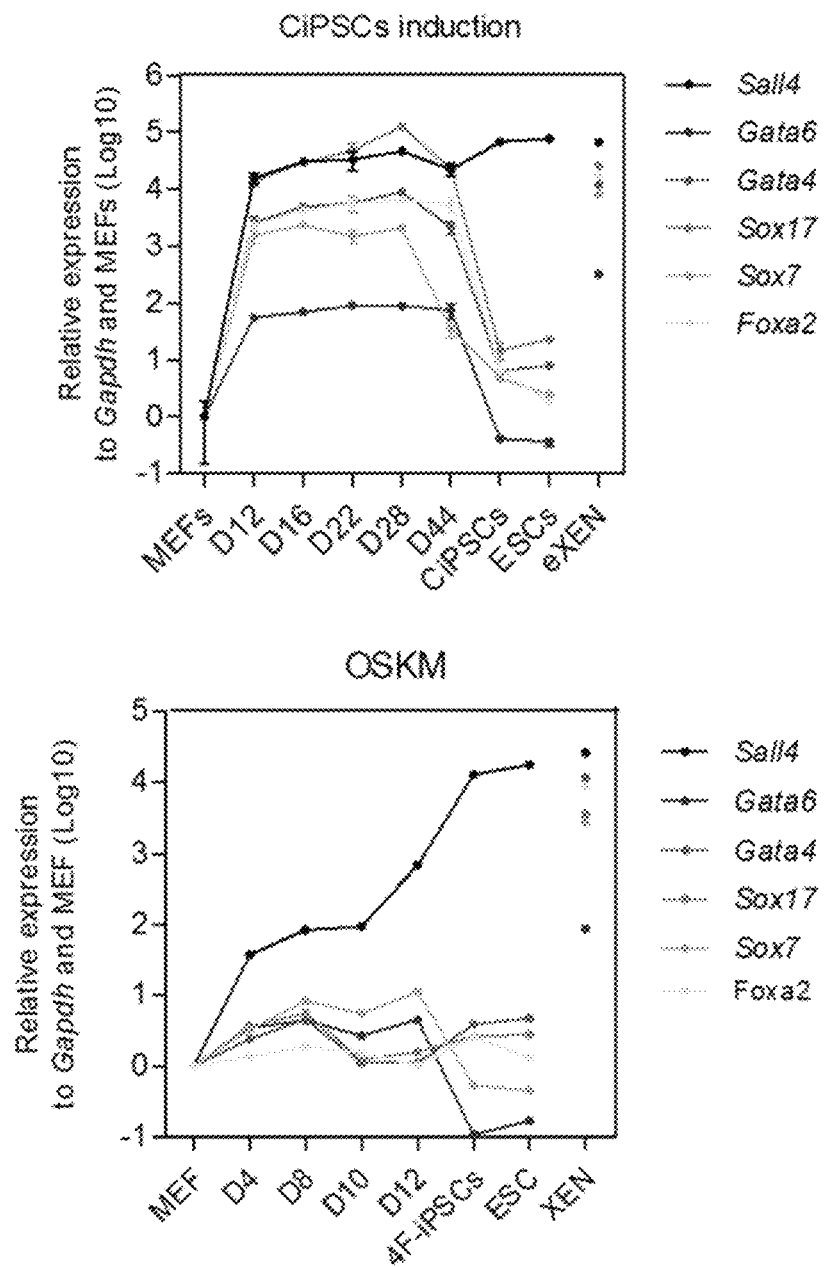
Figure 20D:
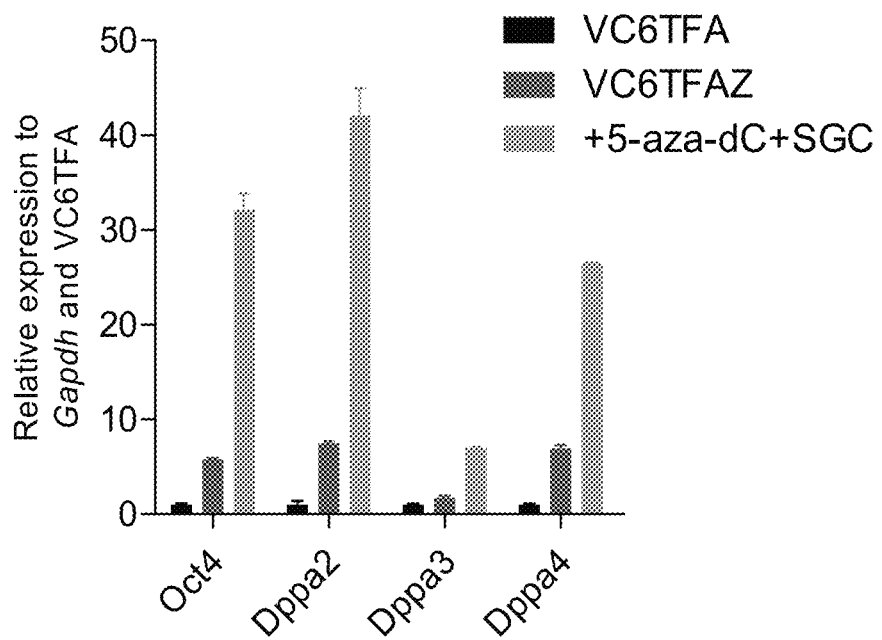
Figure 20E:
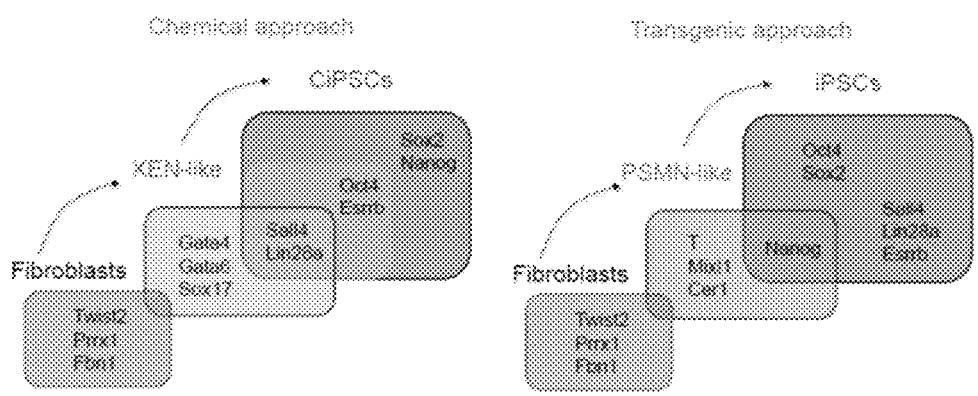

FIG. 20A shows Dynamic expression change in pluripotency-associated genes (Oct4, Sox2, Nanog, Sall4, Lin28a, Zfp42, Dppa2, Esrrb) and MET related genes (Cdh1, EpCAM) at the indicated time points during chemical reprogramming, examined by qRT-PCR. FIG. 20B is a scatter plot diagram of single cell qRT-PCR analysis in the expression of Sall4 and Gata4, Gata4 and Sox17, and Sall4 and Sox2, respectively, at the indicated time points. Gene expression levels were indicated by log 2 (fold change to the minimal level in these samples). FIG. 20C is a Comparison of XEN-related gene expression pattern at indicated time points during chemical reprogramming (upper) and OSKM-induced reprogramming (bottom) measured by qRT-PCR. CiPSCs, 4F-iPSCs, ESCs and eXEN were set as controls. FIG. 20D is qRT-PCR analysis of some pluripotency-associated genes in the cells treated with different cocktails as indicated in stage 2. FIG. 20E is a schematic representation of the two routes of somatic reprogramming by using chemical approach (left) and transgenic approach (right). Error bars indicate biological repeats and the SD (n≥2).

Figure 21A:
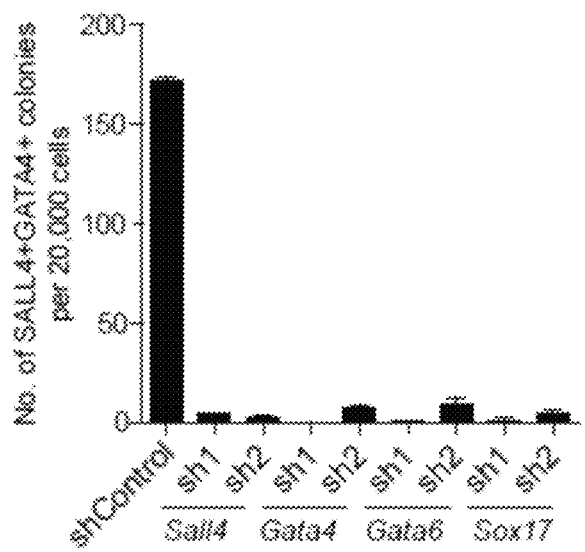
Figure 21B:
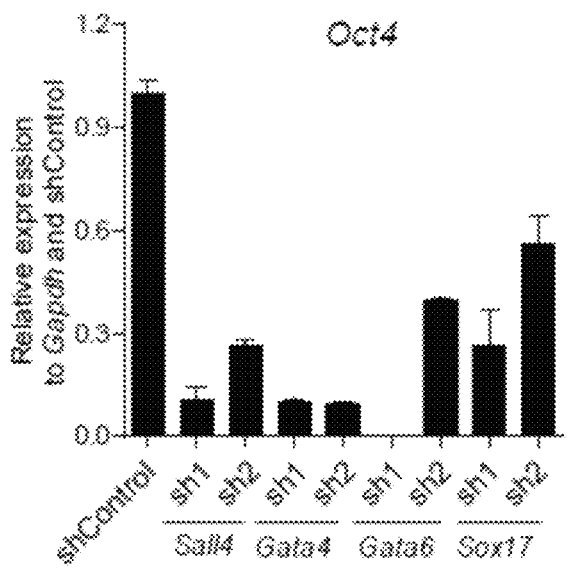
Figure 21C:
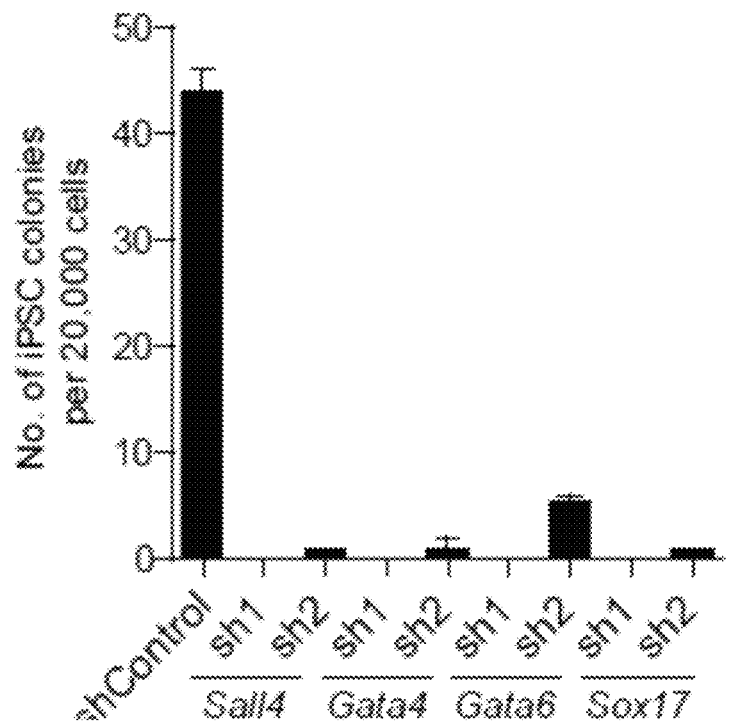
Figure 21D:
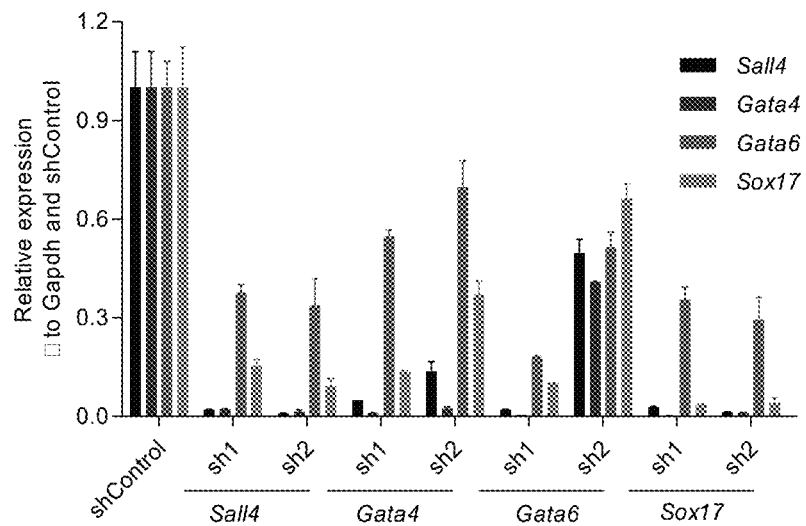

FIG. 21A shows numbers of SALL4 and GATA4 double-positive colonies with Sall4, Gata4, Gata6 or Sox17 knockdown at day 12 of chemical reprogramming. Non-targeting vector shRNA (shControl) was used as negative control. Sh1 and sh2 represent two shRNA vectors for each gene. FIG. 21B shows the expression of Oct4 on day 28 with Sall4, Gata4, Gata6 or Sox17 knockdown measured by qRT-PCR relative to that treated with a non-targeting vector (shControl). FIG. 21C shows numbers of CiPSC colonies with Sall4, Gata4, Gata6 or Sox17 knockdown. FIG. 21D shows The expression of Sall4, Gata4, Gata6 and Sox17 with Sall4, Gata6, Gata4 or Sox17 knockdown measured by qRT-PCR on day 16, relative to that in the non-targeting vector (shControl).

Figure 21E:
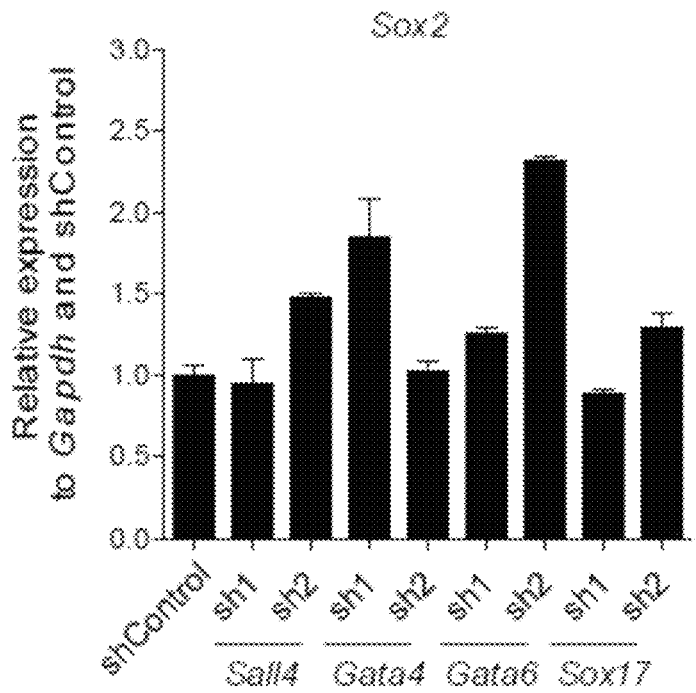
Figure 21F:
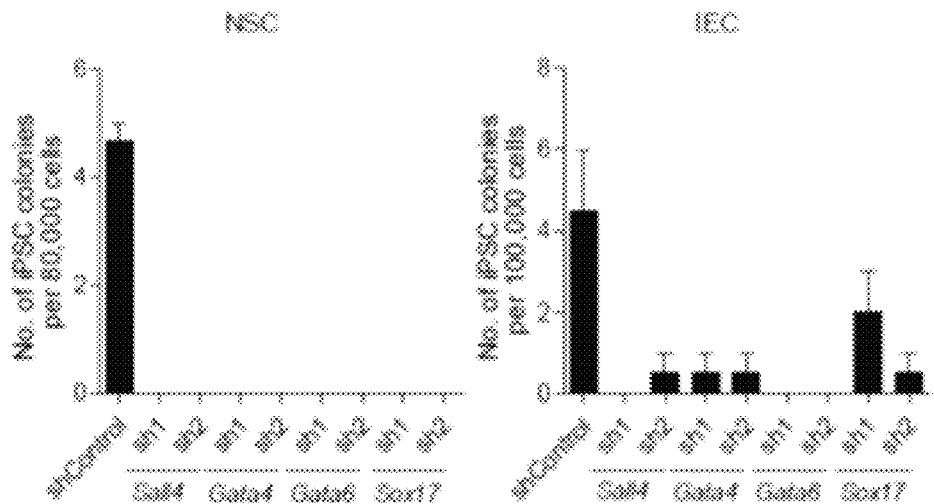
Figure 21G:
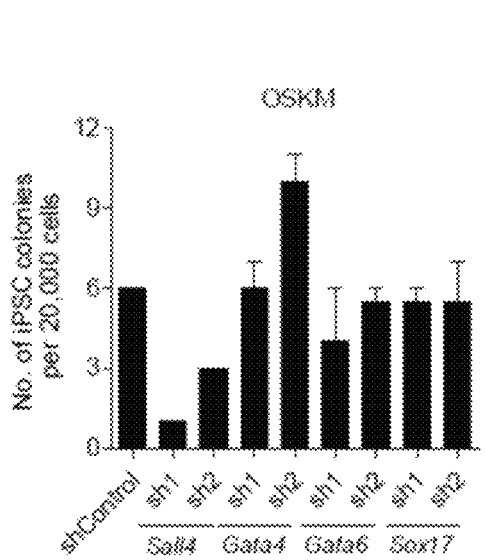
Figure 21H:
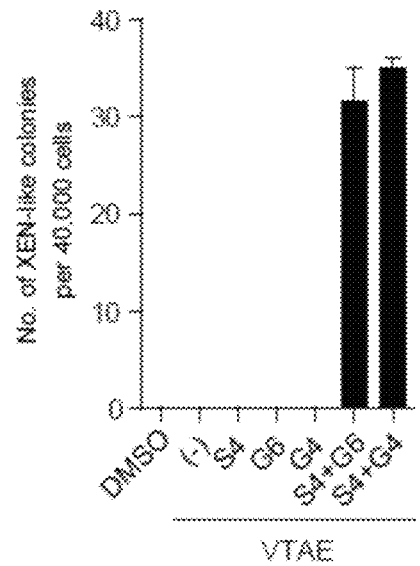
Figure 21I:
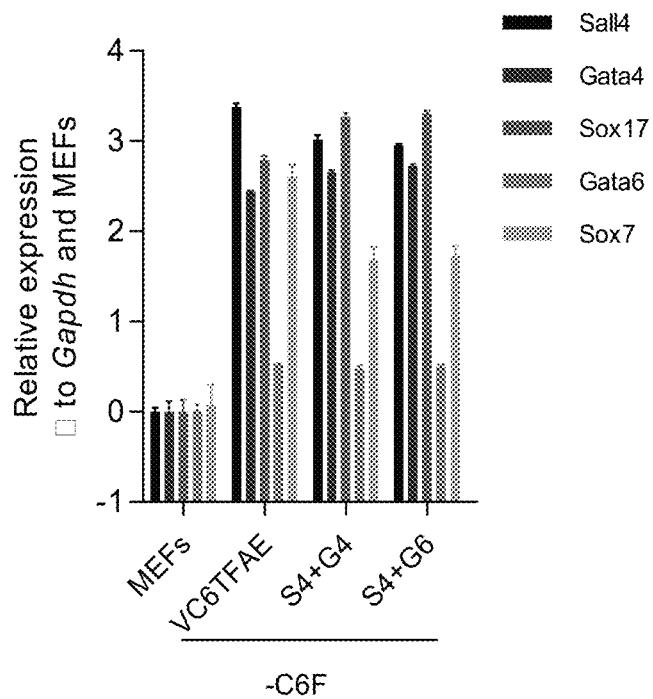

FIG. 21E shows the expression of Sox2 with Sall4,

Gata6, Gata4 or Sox17 knockdown measured by qRT-PCR on day 28, relative to that in the non-targeting vector (shControl). FIG. 21F shows numbers of iPSC colonies induced from neural stem cells (NSCs) and intestinal epithelium cells (IECs) with Sall4, Gata4, Gata6 or Sox17 knockdown. FIG. 21G shows numbers of iPSC colonies induced by OSKM with Sall4, Gata4, Gata6 or Sox17 knockdown. FIG. 21H shows numbers of XEN-like colonies by overexpression of SALL4 (S4), GATA4 (G4), GATA6 (G6) or their combinations in the presence of small-molecule cocktail VTAE (withdrawal of C6F from VC6TFAE) treatment. (−) represents cells treated with VTAE without the overexpression of XEN related genes. DMSO-treated cells are shown as negative controls. FIG. 21I shows qRT-PCR analysis of XEN cell markers Sall4, Gata4, Sox17, Gata6 and Sox7 by treatment of VC6TFAE or overexpression of Sall4 (S4) plus Gata4 (G4) or Gata6 (G6) in the presence of VTAE eXEN was set as a positive control. FIG. 21J shows qRT-PCR analysis of Oct4 induced by overexpression of SALL4, GATA4, GATA6 and their combination in the presence of VTAE on day 20. FIG. 21K shows the expression of Sox2 by the overexpression of SALL4 (S4), GATA4 (G4), GATA6 (G6) and SALL4 plus GATA6 or GATA4 in the presence of VTAE. FIG. 21L shows numbers of iPSC colonies generated by Dox-induced expression of Sox2 in the indicated time courses, with the expression of Sall4 plus Gata4 or Gata6 in the presence of VTAEZ. Error bars indicate the SD (n≥2).

Figure 22A:
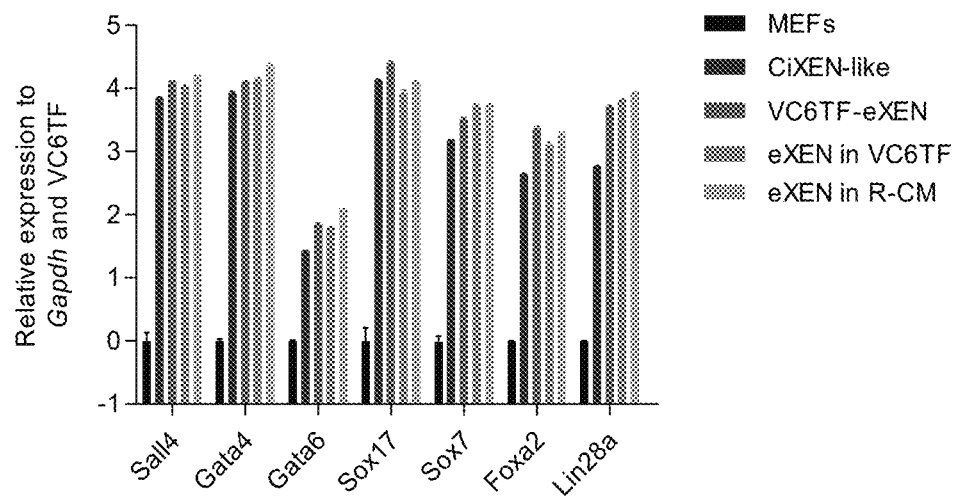
Figure 22B:
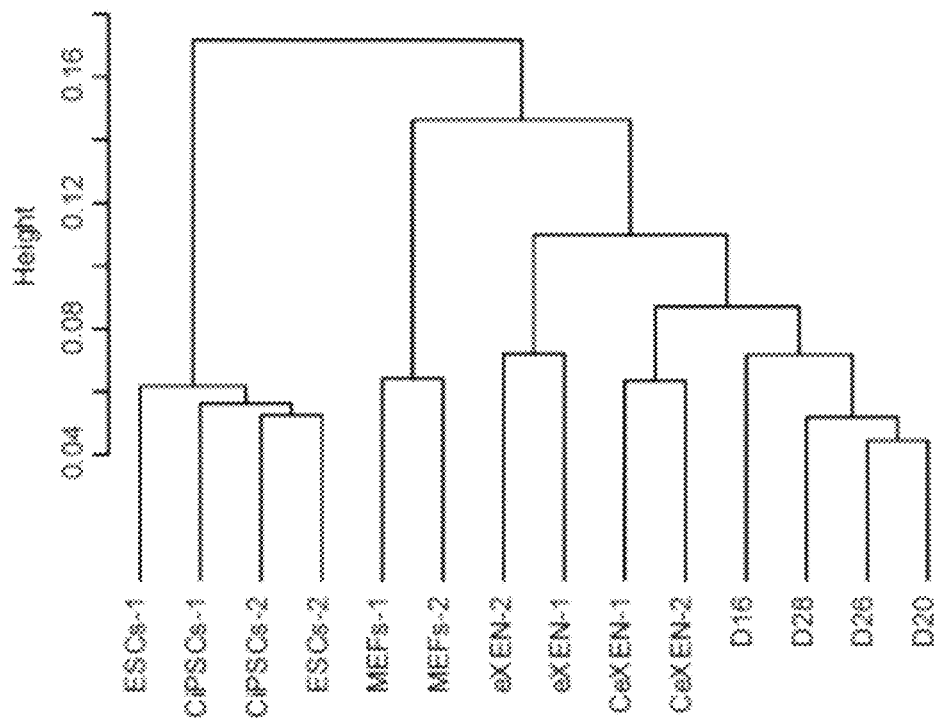
Figure 22C:
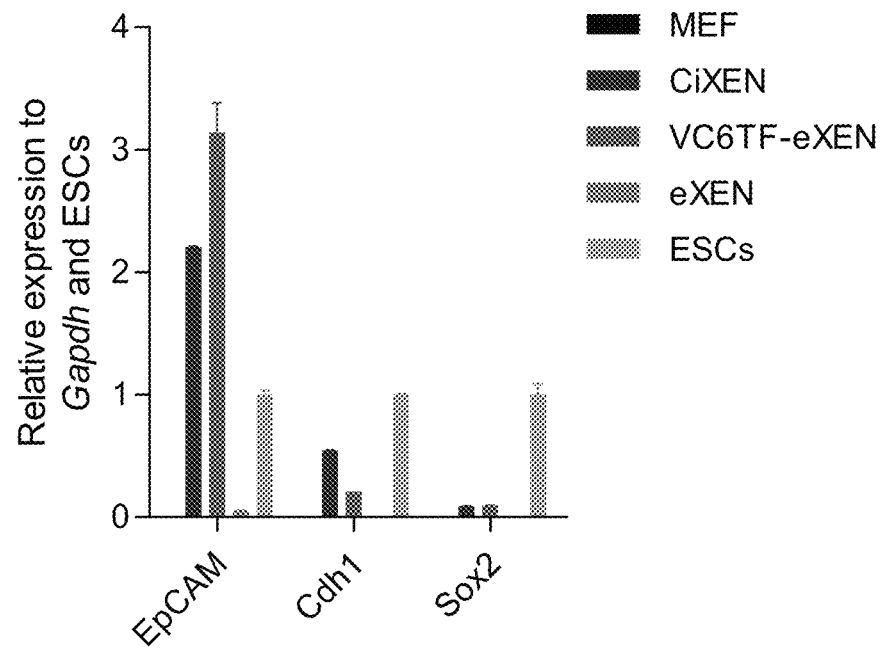
Figure 22D:
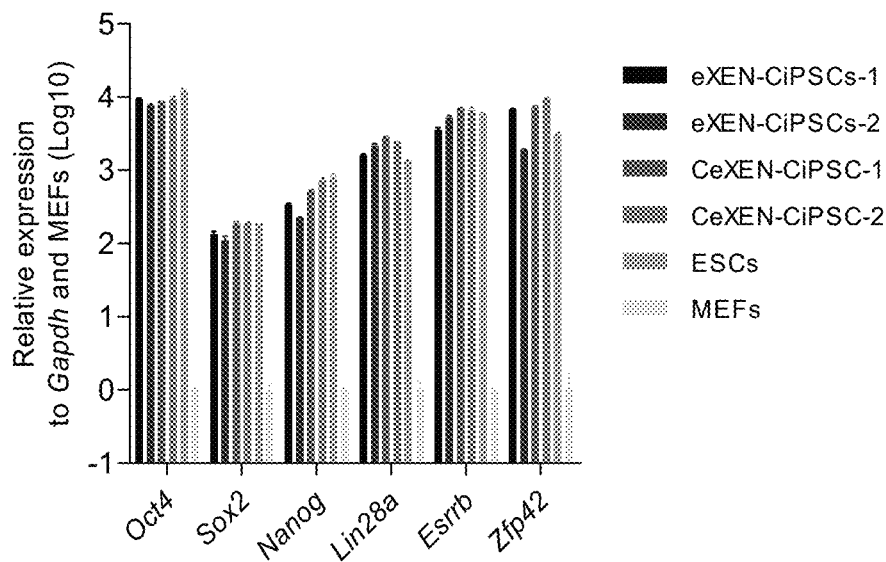

FIG. 22A shows relative expression of XEN-related genes in different cell types as indicated measured by qRT-PCR. eXEN-1 and eXEN-2 were two sublines of eXENs, maintained in traditional XEN culture medium (Kunath et al., 2005) and stage 1 medium of chemical reprogramming, respectively. FIG. 22B shows hierarchical clustering of global gene expression profiles in different cell types. XEN-like cell samples at different time points (day 16, 20, 26 and 28) during chemical reprogramming were indicated as D16, D20, D26 and D28. Controls were two batches of MEFs (MEFs-1, MEFs-2), eXEN-1, eXEN-2, two CeXEN cell lines (CeXEN-1, CeXEN-2), two CiPS cell lines (CiPSCs-1, CiPSCs-2) and two ES cell lines (ESCs-1, ESCs-2). FIG. 22C shows qRT-PCR analysis of EpCAM, Cdh1 and Sox2 in different types of XEN cells as indicated. MEFs and ESCs were set as controls. FIG. 22D shows qRT-PCR analysis of pluripotency marker expression in two CiPSC colonies induced from eXEN and two CiPSC colonies induced from CeXEN. MEFs and ESCs were set as controls. Error bars indicate the SD (n≥2).

DETAILED DESCRIPTION OF THE INVENTION

I. Definitions

The term "chemically induced pluripotent stem cells" (CiPSCs) as used herein refers to pluripotent cells derived from a cell that is not pluripotent, i.e., a multipotent or differentiated cells, by contacting the non-pluripotent cell with chemical compounds, not by expression of one or more transfected genes.

As used herein a "culture" means a population of cells grown in a medium and optionally passaged. A cell culture may be a primary culture (e.g., a culture that has not been passaged) or may be a secondary or subsequent culture (e.g., a population of cells which have been subcultured or passaged one or more times).

As used herein "enhancing", or "increasing" the efficiency of reprogramming means reducing to total reprograming time and/or increasing the number of reprogrammed cells obtained from the same starting cell density the same length of time when compared to a chemical reprograming method that does not proceed via biasing the cells to be programing towards a XEN-like state.

The term "Induced pluripotent stem cell" (iPSC), as used herein, is a type of pluripotent stem cell artificially derived from a non-pluripotent cell. CiPSCs are iPSCs; however, they differ from some iPSCs in that they are not genetically engineered.

The term "isolated" or "purified" when referring to CiPSCs means chemically induced pluripotent stem cells at least 30%, 35%, 40%, 45%, 50%, 55%, 60%, 65%, 70%, 75%, 80%, 85%, 90%, 95%, or 99% free of contaminating cell types such as non-pluripotent cells. The isolated stem cells may also be substantially free of soluble, naturally occurring molecules.

The term "pluripotency" (or pluripotent), as used herein refers to a stem cell that has the potential to differentiate into any of the three germ layers: endoderm (for example, interior stomach lining, gastrointestinal tract, the lungs), mesoderm (for example, muscle, bone, blood, urogenital), or ectoderm (for example, epidermal tissues and nervous system). The term "not pluripotent" means that the cell does not have the potential to differentiate into all of the three germ layers. A multipotent stem cell is less plastic and more differentiated, and can become one of several types of cells within a given organ. For example, multipotent blood stem cells can develop into red blood cell progenitors, white blood cells or platelet producing cells. Adult stem cells are multipotent stem cells. Adipose-derived stem cells are multipotent.

"Reprogramming" as used herein refers to the conversion of a one specific cell type to another. For example, a cell that is not pluripotent can be reprogrammed into a pluripotent cell. Where the non-pluripotent cell is reprogrammed into a pluripotent cell using chemical compounds, the resulting cell is a chemically induced pluripotent stem cell.

"Reprograming medium" as used herein refers to cell culture medium that includes one or more chemical inducers of pluripotency.

"2i medium" as use herein refers to ESC culture medium with dual inhibition of glycogen synthase kinase-3 and mitogen-activated protein kinase signaling, for example, ESC culture medium supplemented with 2i (CHIR99021 and PD0325901).

The term "small molecule" refers to a molecule, such as an organic or organometallic compound, with a molecular weight of less than 2,000 Daltons, more preferably less than 1,500 Daltons, most preferably less than 1,000 Daltons.

"XEN-like cells" are used herein refers to cells which are characterized as epithelial cells, and which express XEN markers such as SALL4, GATA4 and SOX17. XEN-like state when used connection with cells refers to expression of one or more XEN markers.

II. Compositions

A. Small Molecules Inducing Pluripotency

Chemical compounds that induce pluripotency i.e., chemical inducers of pluripotency (CIP) include small molecules having a molecular weight of less than 2,000 Daltons, more preferably less than 1,500 Daltons, most preferably less than 1,000 Dalton, alone or in combination with proteins. The small molecules may have a molecular weight less than or equal to 900 Daltons or, less than or equal to 500 Daltons. Larger molecules can be used in chemically-induced reprogramming, preferably targeting the same pathway as the small molecules identified here. Several protein factors, such as recombinant bFGF, have been demonstrated to be effective in the following protocol for chemical reprogramming.

Accordingly, small molecule cocktails have been identified which can be used to enhance reprogramming of partially or completely differentiated cells (including cells that are not genetically engineered to express one or more markers of pluripotency such as Oct4, and which do not naturally express Oct4), into a XEN-like state and subsequently, into pluripotent cells. The required chemical inducers of pluripotency (CIPs) include (1) a glycogen synthase kinase (GSK) inhibitor, (2) a TGFβ receptor inhibitor, (3) a cyclic AMP agonist, (4) a S-adenosylhomocysteine hydrolase (SAH) inhibitor, (5) a histone acetylator such as valproic acid ("V"), (6) a DOT1L methyltransferase inhibitor, (7) a retinoic acid receptor (RAR) agonist, (8) an epigenetic modulator, (9) an inhibitor of histone demethylation and combinations thereof. The CIPs may be provided separately or in combination as a CIP composition. One or more epigenetic modulators and retinoic acid receptor agonists, for example, retinoic receptor ligands may also be administered with the CIPs. In some preferred embodiments, the CIPs include DZNep as an SAH inhibitor.

(1). GSK Inhibitors

The preferred GSK inhibitor is the aminopyrimidine, CHIR99021 having the chemical name [6-[[2-[[4-(2,4-Dichlorophenyl)-5-(5-methyl-1H-imidazol-2-yl)-2-pyrimidinyl]amino]ethyl]amino]-3-pyridinecarbonitrile] ("C"), used in a concentration of about 20 µM. Other GSK inhibitors can also be used in the methods disclosed herein, and they include, but are not limited to BIO-acetoxime (for example 1 M); GSK 31 inhibitor XV; SB-216763; CHIR 99021 trihydrochloride, which is the hydrochloride salt of CHIR99021; GSK-3 Inhibitor IX [((2Z,3E)-6'-bromo-3-(hydroxyimino)-[2,3'-biindolinylidene]-2'-one]; GSK 3 IX [6-Bromoindirubin-3'-oxime]; GSK-3B Inhibitor XII [3-[6-(3-Aminophenyl)-7H-pyrrolo[2,3-d]pyrimidin-4-yl]oxy] phenol]; GSK-3 Inhibitor XVI [6-(2-(4-(2,4-dichlorophenyl)-5-(4-methyl-1H-imidazol-2-yl)-pyrimidin-2-ylamino) ethyl-amino)-nicotinonitrile]; SB-415286 [3-[(3-chloro-4-hydroxyphenyl)amino]-4-(2-nitrophenyl)-1H-pyrrole-2,5-dione]; and Bio [(2'Z,3'E)-6-bromoindirubin-3'-oxime], used at a concentration equivalent to 20 µM CHIR99021.

(2). TGFβ Receptor Inhibitor

The TGFβ inhibitor is preferably inhibits the TGFβ type 1 receptor activing receptor-like kinase (ALK) 5 in some embodiments, and can additionally inhibit ALK 4 and the nodal type receptor 1 receptor ALK7 in other embodiments The preferred TGFβ receptor inhibitor is 616452. Other TGFβ inhibitors are known in the art and are commercially available. Examples include E-616452 [2-(3-(6-Methylpyridin-2-yl)-1H-pyrazol-4-yl)-1,5-naphthyridine]; A 83-01 [3-(6-Methyl-2-pyridinyl)-N-phenyl-4-(4-quinolinyl)-1H-pyrazole-1-carbothioamide]; SB 505124 [2-[4-(1,3-Benzodioxol-5-yl)-2-(1,1-dimethylethyl)-1H-imidazol-5-yl]-6-methyl-pyridine]; GW 788388 [4-[4-[3-(2-Pyridinyl)-1H-pyrazol-4-yl]-2-pyridinyl]-N-(tetrahydro-2H-pyran-4-yl)-benzamide]; and SB 525334 [6-[2-(1,1-Dimethylethyl)-5-(6-methyl-2-pyridinyl)-1H-imidazol-4-yl]quinoxaline], and dorsomorphin.

(3) cAMP Agonists

The preferred cAMP agonist is Forskolin (F). However, any cAMP agonist can be included in the cocktail of CINPs disclosed herein. Examples include, but are not limited to prostaglandin E2 (PGE2), rolipram, genistein and cAMP analogs such as DBcAMP or 8-bromo-cAMP.

(4). SAH Inhibitors

The preferred SAH inhibitor is 3-deazaneplanocin A (DZNep; "Z"). Other useful SAH hydrolase inhibitors that can be included in the CIP combination compositions disclosed herein include, but are not limited to, (−) Neplanocin A (NepA), Adenozine periodate (oxidized) Adox and 3-deazaadenosine (DZA) and combinations thereof.

(5). Histone Acetylator/Deacetylase Inhibitors

The preferred histone acetylator is valproic acid. However, other histone deacetylase inhibitors are commercially available and can be used. Non-limiting examples include apicidin, CI 994 (N-acetyldinaline 4-(Acetylamino)-N-(2-aminophenyl)benzamide), Depsipeptide, KD 5170 (S-[2-[6-[[[4-[3-(Dimethylamino) propoxy]phenyl]sulfonyl]amino]-3-pyridinyl]-2-oxoethylJethanethioc acid ester), sodium, 4-phenyl butyrate, sodium butyrate, UF 010, etc.

(6). DOT1L Methyltransferase Inhibitors

DOT1L methyltransferase inhibitors are preferred. Preferred examples include methyltransferase inhibitors include SGC 0946 ("S") and EPZ004777 ("E").

(7). Retinoic Acid Receptor (RAR) Agonists

Ch 55 ([4-[(1E)-3-[3,5-bis (1,1-Dimethylethyl)phenyl]-3-oxo-1-propenyl]benzoic acid], a highly potent synthetic retinoid that has high affinity for RAR-α and RAR-β receptors and low affinity for cellular retinoic acid binding protein (CRABP)]; AM580 ([4-[(5,6,7,8-Tetrahydro-5,5,8,8-tetramethyl-2-naphthalenyl) carboxamido]benzoic acid]; an analog of retinoic acid that acts as a selective RARα agonist); [4-[(E)-2-(5,6,7,8-Tetrahydro-5,5,8,8-tetramethyl-2-naphthalenyl)-1-propenyl]benzoic acid] (TTNPB).

Preferred RAR agonists include AM 580 ("A") and Ch 55.

(8). Epigenetic Modulators

Epigenetic modulators that can be included in the CIP composition include one or more of 5-azacytidine, decitabine and RG108 and combinations thereof. A preferred epigenetic modulator is 5-azacytidine ("D").

(9). Inhibitors of Histone Demethylation

A preferred inhibitor of histone demethylation is tranylcypromine ("T"). Tranylcypromine is a nonselective and irreversible monoamine oxidase inhibitor (MAOI). Another useful MAOI which are also inhibitors of histone demethylation include phenelzine (Lee, et al. *Chem and Biol.*, 13:563-567 (2006), Additional non-limiting examples include compound XZ09 disclosed in Zhou, et al., *Chem Biol. and Drug Design*, 85 (6): 659-671 (2015) and non-peptide propargylamines (Schmidttt, et al. *J. Med. Chem.*, 56 (18), pp 7334-7342 (2013).

(10). Additional Small Molecule Boosters

In some embodiments, small molecules that facilitate late reprograming and small molecules that improve/boost chemical reprogramming efficiency over the levels seen with VC6TFZ are included. Improved/boosted efficiency can be manifested by reducing the time needed to generate such pluripotent cells (e.g., by shortening the time to development of pluripotent cells by at least a day compared to a similar or same process without the small molecule). Alternatively, or in combination, a small molecule can increase the number of pluripotent cells generated by a particular process (e.g., increasing the number in a given time period by at least 10%, 50%, 100%, 200%, 500%, etc. compared to a similar or same process without the small molecule).

Small molecules that improve/boost chemical reprogramming efficiency include [N-(9,10-dioxo-9,10-dihydrophenanthren-2-yl) pivalamide] (SF1670); [N-(4-(Diethylaminobenzylidenyl)-N-(4-hydroxybenzoyl)-hydrazine] (DY131); [2-Cyclohexyl-6-methoxy-N-[1-(1-methylethyl)-4-piperidinyl]-7-[3-(1-pyrrolidinyl) propoxy]-4-quinazolinamine] (UNC0638); [N-(2-(3-(piperazin-1-ylmethyl) imidazo [2,1-b]thiazol-6-yl)phenyl) quinoxaline-2-carboxamide hydrochloride] (SRT1720); 2-Me-5HT ("2M5" 2-methyl-5-hydroxytryptamine); and [3,7-Dihydro-1-methyl-3-(2-methylpropyl)-1H-purine-2,6-dioneand] (IBMX) and D4476 (D4476 (CAS 301836-43-1) (4-[4-(2,3-Dihydro-1,4-benzodioxin-6-yl)-5-(2-pyridinyl)-1H-imidazol-2-yl]benzamide), a high purity Casein kinase inhibitor and TGF-β type-I receptor (ALK5) inhibitor). An example of small molecule combinations used to reprogram cells is shown in Table 1A.

TABLE 1A small molecule combination for inducing pluripotency

| small molecule combination that can induce pluripotency | Initial cell numbers | CiPSC colony |
|---|---|---|
| CHIR99021 + 616452 + Forskolin | 100,000 | 1 |
| CHIR99021 + 616452 + Forskolin + DZNep | 50,000 | 3 |
| CHIR99021 + 616452 + Forskolin + DZNep + VPA | 40,000 | 8 |
| CHIR99021 + 616452 + Forskolin + DZNep + TTNPB | 28,000 | |
| CHIR99021 + 616452 + Forskolin + DZNep + Tranylcypromine | 90,000 | 1 |
| CHIR99021 + 616452 + Forskolin + VPA + Tranylcypromine | 50,000 | 1 |
| CHIR99021 + 616452 + DZNep + VPA + Tranylcypromine | 300,000 | 1 |
| CHIR99021 + 616452 + Forskolin + DZNep + 4PB + Tranylcypromine | 20,000 | 2 |
| CHIR99021 + 616452 + Forskolin + DZNep + VPA + Tranylcypromine (VC6TFZ) | 40,000 | 12 |
| CHIR99021 + 616452 + DBcAMP + DZNep + VPA + Tranylcypromine | 40,000 | 1 |
| CHIR99021 + 616452 + IBMX + DZNep + VPA + Tranylcypromine | 40,000 | 1 |
| CHIR99021 + 616452 + Rolipram + DZNep + VPA + Tranylcypromine | 40,000 | 1 |
| CHIR99021 + 616452 + Forskolin + NepA + VPA + Tranylcypromine | 50,000 | 32 |
| CHIR99021 + 616452 + Forskolin + Adox + VPA + Tranylcypromine | 50,000 | 28 |
| CHIR99021 + 616452 + Forskolin + DZA + VPA + Tranylcypromine | 50,000 | 10 |
| CHIR99021 + 616452 + Forskolin + Decitabine + EPZ + VPA + Tranylcy-promine | 30,000 | 14 |
| CHIR99021 + 616452 + Forskolin + DZNep + VPA + Tranylcypromine + TTNPB | 40,000 | 20 |
| CHIR99021 + 616452 + Forskolin + DZNep + VPA + Tranylcypromine + AM580 | 40,000 | 25 |
| CHIR99021 + 616452 + Forskolin + DZNep + VPA + Tranylcypromine + Ch55 | 40,000 | 19 |
| TD114-2 + 616452 + Forskolin + DZNep + VPA + Tranylcypromine | 40,000 | 40 |
| CHIR99021 + 616452 + Forskolin + VPA + Tranylcypromine + 2M5 + D4476 + Butyrate + UNC0638 + Scriptaid | 300,000 | 6 |
| CHIR99021 + 616452 + Forskolin + VPA + Tranylcypromine + TTNPB + PGE2 + 5-aza-C | 250,000 | 5 |
| CHIR99021 + 616452 + Forskolin + VPA + Tranylcypromine + TTNPB + PGE2 + Decitabine | 250,000 | 8 |
| CHIR99021 + 616452 + Forskolin + VPA + Tranylcypromine + Decitabine + EPZ | 30.000 | 14 |

Concentration ranges for exemplary small molecules that can be included in the formulations disclosed herein are provided in Table 1B.

TABLE 1B summary of small molecule concentrations

| Chemical names | Concentration ranges | preferred concentrations μM |
|---|---|---|
| CHIR99021 | 0.1-40 | 20 |
| 616452 | 0.1-50 | 10 |
| *Forskolin | 0.1-100 | 10 or 50 |
| DZNep | 0.005-0.5 | 0.05 |
| WA | 50-2000 | 500 |
| SGC 0946 | 2-10 | 5 |
| TTNPB | 0.01-5 | 2 |
| Tranylcypromine | 1-40 | 5 |
| 4PB | 0.1-50 | 2 |
| DBcAMP | 0.1-500 | 50 |
| IBMX | 0.1-500 | 50 |
| Rolipram | 0.1-50 | 10 |
| NepA | 0.01-5 | 0.05 |
| Adox | 0.1-50 | 10 |
| DZA | 0.1-50 | 10 |
| Decitabine | 0.01-5 | 0.1 |
| EPZ | 0.1-20 | 5 |
| AM580 | 0.01-5 | 0.05 |
| Ch55 | 0.01-5 | 2 |
| TD114-2 | 0.1-20 | 2 |
| 2M5 | 0.1-40 | 5 |
| D4476 | 0.1-40 | 5 |
| Butyrate | 1-400 | 200 |
| UNC0638 | 0.01-5 | 0.5 |
| Scriptaid | 0.01-5 | 0.5 |
| PGE2 | 0.1-20 | 5 |

TABLE 1B-continued summary of small molecule concentrations

| Chemical names | Concentration ranges | preferred concentrations μM |
|---|---|---|
| 5-aza-C | 0.01-50 | 5 |
| RG108 | 0.01-100 | 10 |
| SRT1720 | 0.1-20 | 2 |

*50 μM Forskolin is preferred in a XEN-cocktail 10 μM forskolin if preferred in a XEN-XiPSC cocktail.

B. Protein Factors

Protein factors, such as recombinant basic fibroblast growth factor (bFGF), have been demonstrated to be effective in the following protocol for chemical reprogramming. bFGF can be used in a concentration range from 10 ng/mL-200 ng/mL, preferably at concentration of 100 ng/mL.

C. Cells to be Induced

The induced pluripotent stem cells are obtained by inducing partially or completely differentiated cells obtained from a mammal such as any mammal (e.g., bovine, ovine, porcine, canine, feline, equine, primate), preferably a human. Sources include bone marrow, fibroblasts, fetal tissue (e.g., fetal liver tissue), peripheral blood, umbilical cord blood, pancreas, skin or any organ or tissue. In a preferred embodiment, the CiPSCs are obtained from chemically induced fibroblasts, adipose-derived stem cells, neural stem cells or cells from the intestinal epithelium. In a more preferred embodiment, CiPSCs are obtained from chemically induced neonatal (for example foreskin) or adult fibroblasts. However, CiPSCs can be obtained from other cell types including but not limited to: multipotent stem cells, cells of hematological origin, cells of embryonic origin, skin derived cells, fibroblasts, adipose cells, epithelial cells, endothelial cells, mesenchymal cells, parenchymal cells, neurological cells, and connective tissue cells. multipotent stem cells, cells of hematological origin, cells of embryonic origin, skin derived cells, fibroblasts, adipose cells, epithelial cells, endothelial cells, mesenchymal cells, parenchymal cells, neurological cells, and connective tissue cells. The cell to be reprogrammed can be obtained from a sample obtained from a mammalian subject. The subject can be any mammal (e.g., bovine, ovine, porcine, canine, feline, equine, primate), including a human. The sample of cells may be obtained from any of a number of different sources including, for example, bone marrow, fetal tissue (e.g., fetal liver tissue), peripheral blood, umbilical cord blood, pancreas, skin or any organ or tissue.

In a preferred embodiment, the CiPSCs are obtained from fibroblasts and adipose-derived stem cells. In a more preferred embodiment, CiPSCs are obtained from fibroblast, which can be neonatal (for example foreskin fibroblasts) or adult fibroblast. In still another preferred embodiment, the non-pluripotent cells do not express Oct4 and/or are not genetically engineered to express one or more markers of pluripotency.

Cells may be isolated by disaggregating an appropriate organ or tissue which is to serve as the cell source using techniques known to those skilled in the art. For example, the tissue or organ can be disaggregated mechanically and/or treated with digestive enzymes and/or chelating agents that weaken the connections between neighboring cells, so that the tissue can be dispersed to form a suspension of individual cells without appreciable cell breakage. Enzymatic dissociation can be accomplished by mincing the tissue and treating the minced tissue with one or more enzymes such as trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators.

D. Chemically Induced Pluripotent Stem Cells (CiPSCs)

CiPSCs are physiologically and morphologically indistinguishable from Embryonic Stem Cells (ESC). The Examples show that CiPSCs grow with a doubling time similar to ESC, and like ESC, express pluripotency markers, have a similar gene expression profile to ESC, and have a similar DNA methylation and histone modifications at Oct4 and Nanog promoters. Karyotyping analysis also demonstrates that CiPSCs do not acquire chromosomal abnormalities. Further evidence that the CiPSCs are pluripotent is their ability to differentiate into tissues of the three embryonic germ layers. These findings demonstrate the ability to manipulate differentiated human cells to generate an unlimited supply of patient-specific pluripotent stem cells.

CiPSCs possess ESC-like properties such as ESC morphology, doubling time similar to ESC, expression of ESC markers such as alkaline phosphatase (AP), nanog, Rex1, Sox2, Dax1, Sall4, undifferentiated embryonic cell transcription factor (Utf1), stage specific embryonic antigen-4 (SSEA-4), and the ability of the cell to differentiate into tissues of the three embryonic germ layers. Such cells can also be characterized by the down-regulation of markers characteristic of the differentiated cell from which the CiPSC is induced. For example, CiPSCs derived from fibroblasts may be characterized by down-regulation of the fibroblast cell marker Thy1 and/or up-regulation of SSEA-1. There is no minimum number of pluripotency markers that must be displayed on CiPSCs. The gold standard for pluripotency is the differentiation potential into cell types of all three germ layers. Teratoma assay, chimeras assay and the germ-line transmission capability are some direct assays to test their differentiation potential.

III. Methods of Making

A. Induction of CiPSCs CiPSCs can be induced by providing partially or completely differentiated cells in a culture media containing the CIPs for a sufficient period of time to result in reprograming the cells into chemically induced pluripotent stem cell (CiPSC). The reprogrammed cells are defined as pluripotent cells based on possession of ESC-like properties such as morphology, doubling time, expression of ESC markers for example alkaline phosphatase (AP); nanog, Rex1; Sox2; Dax1; Sall4; undifferentiated embryonic cell transcription factor (Utf1); stage specific embryonic antigen-4 (SSEA-4), and the ability of the cell to differentiate into tissues of the three embryonic germ layers.

The CIP compounds are contacted with the cells to be induced in an amount effective to induce and/or enhance reprograming of non-pluripotent cells into pluripotent cells. One of skill in the art can readily determine the concentrations of the CIP compounds disclosed herein required to provide complete reprograming using methods outlined in the examples below, or other methods known in the art. In some preferred embodiments, the CIPs include an SAH inhibitor.

VPA is administered to the cells to a concentration between 500 UM and 0.5 mM, CHIR is administered to a concentration between 10 to 20 μM preferably, 20 μM, 616452 is administered to a concentration between 5 to 10 μM, FSK is administered to a concentration between 10 to 50 M and DZNep is administered to a concentration between 20 nM and 0.1 µM, preferably, between 0.05 to 0.1 µM, and more preferably, between 20 and 200 nM. Exemplary combinations of small molecules that can be used to induce pluripotency in a non-pluripotent cell and concentration ranges are provided in Tables 1A and B.

616452 and Forskolin need to be present the entire time before the use of 2i-medium. CHIR99021 should be used in the first 12 days, and is preferably present the entire time before the use of 2i-medium. DZNep should be added at the late stage of reprogramming (day 12 to day 40), preferably, day 16 after the initial treatment of other small molecules. The small molecule combination should be changed into 2i-medium after a time point between day 26 and day 48, preferably day 28. Different cell types have different optimal concentrations of small molecules. These can be determined by routine experimentation based on the studies described herein. The order of exposure and the period of time of exposure are similar between cell types.

In a preferred embodiment, the method includes culturing cells in a reprograming medium containing the CIPs, and further culturing the cells in an ESC culture medium for more than 4 days with dual inhibition of glycogen synthase kinase-3 (GSK3) and mitogen-activated protein kinase (MAPK) signaling after about day 28 post treatment with the reprograming medium. In one embodiment, dual inhibition of GSK3 and MAPK is accomplished using CHIR99021 and PD0325901.

In some embodiments, the method further includes contacting the cells with additional small molecules that facilitate late reprograming for example, cAMP agonists other than forskolin and/or epigenetic modulators disclosed herein, and/or small molecules that improve/boost chemical reprograming efficiency disclosed herein. Epigenetic modulators can be included in the composition containing VC6TF. Alternatively, these small molecules can be included in cell culture medium following treatment of the cells with VC6TF. The cells are preferably exposed to the small molecules for more than 1 day. In some embodiments, treatment of cells with cAMP agonists and epigenetic modulators does not exceed the period of treatment with VC6TF. In other embodiments treatment of cells with cAMP agonists and epigenetic modulators does not exceed the period of treatment with VC6TFZ. In still other embodiments, treatment of cells with cAMP agonists and epigenetic modulators does not exceed the period of treatment with VC6TF plus VC6TFZ. A preferred small molecule for boosting chemical reprogramming efficiency is TTNPB.

The disclosed methods yield induced pluripotent stem cells without the need to transfect cells with genes such as Oct4, KLF4, SOX2, C-Myc or NANOG or the need to contact the cells with any of the KLF, Oct, Myc and/or Sox polypeptide.

B. Induction of CiPSCs Via Specific Selection of Conditions for XEN-Like State Bias Reprogramming non-pluripotent cells via a XEN-like state bias includes the steps of (a) contacting the cell to be reprogrammed with a first cocktail of CIPs (XEN-cocktail) for a sufficient period of time to bias the cells into a XEN-like state, thus generating a subpopulation XEN-like cells; (b) contacting the population of XEN-like cells for a sufficient period of time to reprogram the cells into a chemically induced pluripotent stem cell (CiPSC) with a second cocktail of CIPS (XEN-CiPSC cocktail) and (c) culturing the cells in 2i-medium. The cells are preferably replated during step (a) at a density of about 50,000-100,000 cells per well in a 6-well plate.

In a preferred embodiment, cells to be reprogrammed are cultured initially in a reprograming medium containing the CIPs for a total period preferably between 26-30 days. The cells are then cultured in 2i-medium for more than 4 days. The cells are cultured in 2i-medium from preferably, between 10-14 days (FIG. 19A) In a preferred embodiment, the VC6TF cocktail is present the entire time before the use of 2i-medium. AM 580 should be used in step (a), and is preferably present the entire time before the use of 2i-medium. EPZ004777 is preferably added in step (a) and may be present the entire time before the use of the 2i-medium. Accordingly, a preferred XEN-cocktail for biasing/priming cells to be reprogrammed into a XEN-like state is VC6TFAE. 5-azacytidine and should be added in step (b) following treatment with the preferred VC6TFAE cocktail at the late stage of reprogramming (for example, day 16 to day28). SGC 0946 is preferably not included in the reprogramming medium in step (a) for biasing cells into a XEN-like state, but is preferably included in step (b) for programing XEN-like cells into caps. Accordingly, a preferred cocktail for step (b) (XEN-CiPSC-cocktail is VC6TFZASD. In some preferred embodiments, the concentration of forskolin in the XEN-cocktail is different from its concentration in the XEN-CiPSC cocktail (5:1). The XEN-CiPSC-cocktail should be changed into 2i-medium between day 26 to day 30, and preferably day 28. The 2i-medium preferably additionally includes N2B27. N2B27-2i medium (500 mL) includes the following: 240 ml DMEM/F12 (Invitrogen), 240 ml Neurobasal (Invitrogen), 5 ml N2 supplement (Invitrogen), 10 ml B27 supplement (Invitrogen), 2 mM GlutaMAX™-I (Invitrogen), 1% nonessential amino acids (Invitrogen), 0.1 mM 2-mercaptoethanol (Invitrogen), 1% penicillin-streptomycin (Invitrogen), 3 µM CHIR99021, 1 µM PD0325901 and 1,000 U/ml LIF.

Inducing CiPSCs via XEN-like state bias increases the efficiency of reprogramming. For example, the number of colonies obtained cells to be programmed are first biased towards a XEN-LIKE state from the same starting cell population is increased and/or the length of time it takes to obtain the same number of colonies is reduced when compared to a chemical reprograming method that does not selectively bias the cells to be programing towards a XEN-like state.

C. Isolation of CiPSCs

Media that can maintain the undifferentiated state and pluripotency of ES cells or induce differentiation are known in this field. Differentiation and proliferation abilities of isolated induced pluripotent stem cells can be easily confirmed by those skilled in the art by using confirmation means widely applied to ES cells.

A substantially purified population of CiPSCs can be obtained, for example, by extraction (e.g., via density gradient centrifugation and/or flow cytometry) from a culture source. Purity can be measured by any appropriate method. The pluripotent cells can be 99%-100% purified by, for example, flow cytometry (e.g., FACS analysis). Human induced pluripotent stem cells can be isolated by, for example, utilizing molecules (e.g., antibodies, antibody derivatives, ligands or Fc-peptide fusion molecules) that bind to a marker (e.g., a TRA-1-81, a TRA-1-61 or a combination of markers) on the induced pluripotent stem cells and thereby positively selecting cells that bind the molecule (i.e., a positive selection). Other examples of positive selection methods include methods of preferentially promoting the growth of a desired cell type in a mixed population of desired and undesired cell types. Alternatively, by using molecules that bind to markers that are not present on the desired cell type, but that are present on an undesired cell type, the undesired cells containing such markers can be removed from the desired cells (i.e., a negative selection). Other negative selection methods include preferentially killing or inhibiting the growth of an undesired cell type in a mixed population of desired and undesired cell types. Accordingly, by using negative selection, positive selection, or a combination thereof, an enriched population of stem cell can be made.

Procedures for separation may include magnetic separation, using antibody-coated magnetic beads, affinity chromatography, cytotoxic agents joined to a monoclonal antibody, or such agents used in conjunction with a monoclonal antibody, e.g., complement and cytotoxins, and "panning" with antibody attached to a solid matrix (e.g., plate), or other convenient technique. Techniques providing accurate separation include fluorescence activated cell sorters, which can have varying degrees of sophistication, e.g., a plurality of color channels, low angle and obtuse light scattering detecting channels, and impedance channels. Antibodies may be conjugated with markers, such as magnetic beads, which allow for direct separation, biotin, which can be removed with avidin or streptavidin bound to a support, or fluorochromes, which can be used with a fluorescence activated cell sorter, to allow for ease of separation of the particular cell type. Any technique may be employed which is not unduly detrimental to the viability of the induced pluripotent stem cells. In one embodiment, the cells are incubated with an antibody against a marker (e.g., a TRA-1-81 antibody) and the cells that stain positive for the marker are manually selected and subcultured.

Combinations of enrichment methods may be used to improve the time or efficiency of purification or enrichment. For example, after an enrichment step to remove cells having markers that are not indicative of the cell type of interest, the cells may be further separated or enriched by a fluorescence activated cell sorter (FACS) or other methodology having high specificity. Multi-color analyses may be employed with a FACS. The cells may be separated on the basis of the level of staining for a particular antigen or lack thereof. Fluorochromes may be used to label antibodies specific for a particular antigen. Such fluorochromes include phycobiliproteins, e.g., phycoerythrin and allophycocyanins, fluorescein, and Texas red.

Any cell type-specific markers can be used to select for or against a particular cell type. Induced stem cell markers useful for enrichment comprise expressed markers such as TRA-1-81 and loss of markers (e.g., GFP) associated with a retroviral vector or other exogenous vector.

C. Culture and Preservation of CiPSCs (and their Progeny)

The CiPSCs can be expanded in culture and stored for later retrieval and use. Once a culture of cells or a mixed culture of stem cells is established, the population of cells is mitotically expanded in vitro by passage to fresh medium as cell density dictates under conditions conducive to cell proliferation, with or without tissue formation. Such culturing methods can include, for example, passaging the cells in culture medium lacking particular growth factors that induce differentiation (e.g., IGF, EGF, FGF, VEGF, and/or other growth factor). Cultured cells can be transferred to fresh medium when sufficient cell density is reached. Some stem cell types do not demonstrate typical contact inhibition-apoptosis or they become quiescent when density is maximum. Accordingly, appropriate passaging techniques can be used to reduce contact inhibition and quiescence.

Cells can be cryopreserved for storage according to known methods, such as those described in Doyle et al., (eds.), 1995, Cell & Tissue Culture: Laboratory Procedures, John Wiley & Sons, Chichester. For example, cells may be suspended in a "freeze medium" such as culture medium containing 15-20% fetal bovine serum (FBS) and 10% dimethylsulfoxide (DMSO), with or without 5-10% glycerol, at a density, for example, of about $4\text{-}10\times10^6$ cells/ml. The cells are dispensed into glass or plastic vials which are then sealed and transferred to a freezing chamber of a programmable or passive freezer. The optimal rate of freezing may be determined empirically. For example, a freezing program that gives a change in temperature of $-1°$ C./min through the heat of fusion may be used. Once vials containing the cells have reached $-80°$ C., they are transferred to a liquid nitrogen storage area. Cryopreserved cells can be stored for a period of years.

IV. Methods of Use

Identification of a readily available source of stem cells that can give rise to a desired cell type or morphology is important for therapeutic treatments, tissue engineering and research. The availability of stem cells would be extremely useful in transplantation, tissue engineering, regulation of angiogenesis, vasculogenesis, and cell replacement or cell therapies as well as the prevention of certain diseases. Such stem cells can also be used to introduce a gene into a subject as part of a gene therapy regimen.

A. Providing Differentiated Somatic Cells (Re-Differentiated Cells)

Once established, a culture of stem cells may be used to produce progeny cells, for example, fibroblasts capable of producing new tissue. The CiPSCs can be induced to differentiate into cells from any of the three germ layers, for example, skin and hair cells including epithelial cells, keratinocytes, melanocytes, adipocytes, cells forming bone, muscle and connective tissue such as myocytes, chondrocytes, osteocytes, alveolar cells, parenchymal cells such as hepatocytes, renal cells, adrenal cells, and islet cells, blood cells, retinal cells (and other cells involved in sensory perception, such as those that form hair cells in the ear or taste buds on the tongue), and nervous tissue including nerves.

In one embodiment, the CiPSCs are induced to differentiate into cells of ectodermal origin by exposing the cells to an "ectodermal differentiating" media. In another embodiment the CiPSCs are induced to differentiate into cells of mesodermal origin by exposing the cells to "mesodermal differentiating media". In still another embodiment, the CiPSCs are induced to differentiate into cells of endodermal origin by exposing the cells to "endodermal media". Components of "endodermal", "mesodermal" and "ectodermal" media are known to one of skill in the art. Known cell surface markers can be used to verify that the cells are indeed differentiating into cells of the lineage of the corresponding cell culture medium. The most commonly accepted markers to confirm differentiation of the three germ layers are the expression of alpha fetal protein for endodermal cells, alpha smooth muscle actin for mesoderm, and Beta-III tubulin for ectoderm, all of which are normally expressed very early in the development of these tissues.

Differentiation of stem cells to fibroblasts or other cell types, followed by the production of tissue therefrom, can be triggered by specific exogenous growth factors or by changing the culture conditions (e.g., the density) of a stem cell culture. Methods for inducing differentiation of cells into a cell of a desired cell type are known in the art. For example, CiPSCs can be induced to differentiate by adding a substance (e.g., a growth factor, enzyme, hormone, or other signaling molecule) to the cell's environment. Examples of factors that can be used to induce differentiation include erythropoietin, colony stimulating factors, e.g., GM-CSF, G-CSF, or M-CSF, interleukins, e.g., IL-1, -2, -3, -4, -5, -6, -7, -8, Leukemia Inhibitory Factory (LIF), or Steel Factor (Stl), coculture with tissue committed cells, or other lineage committed cells types to induce the stem cells into becoming committed to a particular lineage.

The redifferentiated cells can be can be expanded in culture and stored for later retrieval and use.

B. Cell Therapy

Therapeutic uses of the induced pluripotent stem cells include transplanting the induced pluripotent stem cells, stem cell populations, or progeny thereof into individuals to treat a variety of pathological states including diseases and disorders resulting from cancers, wounds, neoplasms, injury, viral infections, diabetes and the like. Treatment may entail the use of the cells to produce new tissue, and the use of the tissue thus produced, according to any method presently known in the art or to be developed in the future. The cells may be implanted, injected or otherwise administered directly to the site of tissue damage so that they will produce new tissue in vivo. In one embodiment, administration includes the administration of genetically modified CiPSCs or their progeny.

In a preferred embodiment, the CiPSCs are obtained from autologous cells i.e., the donor cells are autologous. However, the cells can be obtained from heterologous cells. In one embodiment, the donor cells are obtained from a donor genetically related to the recipient. In another embodiment, donor cells are obtained from a donor genetically un-related to the recipient.

If the human CiPSCs are derived from a heterologous (non-autologous/allogenic) source compared to the recipient subject, concomitant immunosuppression therapy is typically administered, e.g., administration of the immunosuppressive agent cyclosporine or FK506. However, due to the immature state of the human induced pluripotent stem cells such immunosuppressive therapy may not be required. Accordingly, in one embodiment, the human induced pluripotent stem cells can be administered to a recipient in the absence of immunomodulatory (e.g., immunosuppressive) therapy. Alternatively, the cells can be encapsulated in a membrane, which permits exchange of fluids but prevents cell/cell contact. Transplantation of microencapsulated cells is known in the art, e.g., Balladur et al., Surgery, 117:189-94, 1995; and Dixit et al., Cell Transplantation 1:275-79 (1992).

(i) Diabetes

Diabetes mellitus (DM) is a group of metabolic diseases where the subject has high blood sugar, either because the pancreas does not produce enough insulin, or, because cells do not respond to insulin that is produced.

A promising replacement for insulin therapy is provision of islet cells to the patient in need of insulin. Shapiro et al., *N Engl J Med.*, 343 (4): 230-8 (2000) have demonstrated that transplantation of beta cells/islets provides therapy for patients with diabetes. Although numerous insulin types are commercially available, these formulations are provided as injectables. The human induced pluripotent stem cells provide an alternative source of islet cells to prevent or treat diabetes. For example, induced pluripotent stem cells can be isolated and differentiated to a pancreatic cell type and delivered to a subject. Alternatively, the induced pluripotent stem cells can be delivered to the pancreas of the subject and differentiated to islet cells in vivo. Accordingly, the cells are useful for transplantation in order to prevent or treat the occurrence of diabetes. Methods for reducing inflammation after cytokine exposure without affecting the viability and potency of pancreatic islet cells are disclosed for example in U.S. Pat. No. 8,637,494 to Naziruddin, et al.

(ii) Neurodegenerative Disorders

Neurodegenerative disorders are characterized by conditions involving the deterioration of neurons as a result of disease, hereditary conditions or injury, such as traumatic or ischemic spinal cord or brain injury. Neurodegenerative conditions include any disease or disorder or symptoms or causes or effects thereof involving the damage or deterioration of neurons. Neurodegenerative conditions can include, but are not limited to, Alexander Disease, Alper's Disease, Alzheimer Disease, Amyotrophic Lateral Sclerosis, Ataxia Telangiectasia, Canavan Disease, Cockayne Syndrome, Corticobasal Degeneration, Creutzfeldt-Jakob Disease, Huntington Disease, Kennedy's Disease, Krabbe Disease, Lewy Body Dementia, Machado-Joseph Disease, Multiple Sclerosis, Parkinson Disease, Pelizaeus-Merzbacher Disease, Niemann-Pick's Disease, Primary Lateral Sclerosis, Refsum's Disease, Sandhoff Disease, Schilder's Disease, Steele-Richardson-Olszewski Disease, Tabes *Dorsalis* or any other condition associated with damaged neurons. Other neurodegenerative conditions can include or be caused by traumatic spinal cord injury, ischemic spinal cord injury, stroke, traumatic brain injury, and hereditary conditions.

In particular, the disclosed methods include transplanting into a subject in need thereof NSCs, neural progenitors, or neural precursors that have been expanded in vitro such that the cells can ameliorate the neurodegenerative condition. Transplantation of the expanded neural stem cells can be used to improve ambulatory function in a subject suffering from various forms of myelopathy with symptoms of spasticity, rigidity, seizures, paralysis or any other hyperactivity of muscles. Methods for expanding and transplanting neural cells and neural progenitor cells for the treatment of different neurodegenerative conditions is disclosed for example, in U.S. Pat. No. 8,236,299 to Johe, et. al.

(iii) Cancer Therapy

Therapeutic uses of the CiPSCs and their progeny include transplanting the induced pluripotent stem cells, stem cell populations, or progeny thereof into individuals to treat and/or ameliorate the symptoms associated with cancer. For example, in one embodiment, the CiPSCs can be administered to cancer patients who have undergone chemotherapy that has killed, reduced, or damaged cells of a subject. In a typical stem cell transplant for cancer, very high doses of chemotherapy are used, often along with radiation therapy, to try to destroy all the cancer cells. This treatment also kills the stem cells in the bone marrow. Soon after treatment, stem cells are given to replace those that were destroyed.

In another embodiment, the CiPSCs can be transfected or transformed (in addition to the de-differentiation factors) with at least one additional therapeutic factor. For example, once CiPSCs are isolated, the cells may be transformed with a polynucleotide encoding a therapeutic polypeptide and then implanted or administered to a subject, or may be differentiated to a desired cell type and implanted and delivered to the subject. Under such conditions the polynucleotide is expressed within the subject for delivery of the polypeptide product.

(iii) Tissue Engineering

CiPSCs and their progeny can be used to make tissue engineered constructions, using methods known in the art. Tissue engineered constructs may be used for a variety of purposes including as prosthetic devices for the repair or replacement of damaged organs or tissues. They may also serve as in vivo delivery systems for proteins or other molecules secreted by the cells of the construct or as drug delivery systems in general. Tissue engineered constructs also find use as in vitro models of tissue function or as models for testing the effects of various treatments or pharmaceuticals. The most commonly used biomaterial scaffolds for transplantation of stem cells are reviewed in the most commonly used biomaterial scaffolds for transplantation of stem cells is reviewed in Willerth, S. M. and Sakiyama-Elbert, S. E., *Combining stem cells and biomaterial scaffolds for constructing tissues and cell delivery* (Jul. 9, 2008), StemBook, ed. The Stem Cell Research Community, StemBook. Tissue engineering technology frequently involves selection of an appropriate culture substrate to sustain and promote tissue growth. In general, these substrates should be three-dimensional and should be processable to form scaffolds of a desired shape for the tissue of interest.

U.S. Pat. No. 6,962,814 generally discloses method for producing tissue engineered constructs and engineered native tissue. With respect to specific examples, U.S. Pat. No. 7,914,579 to Vacanti, et al., discloses tissue engineered ligaments and tendons. U.S. Pat. No. 5,716,404 discloses methods and compositions for reconstruction or augmentation of breast tissue using dissociated muscle cells implanted in combination with a polymeric matrix. U.S. Pat. No. 8,728,495 discloses repair of cartilage using autologous dermal fibroblasts. U.S. Published application No. 20090029322 by Duailibi, et al., discloses the use of stem cells to form dental tissue for use in making tooth substitute. U.S. Published application No. 2006/0019326 discloses cell-seed tissue-engineered polymers for treatment of intracranial aneurysms. U.S. Published application No. 2007/0059293 by Atala discloses the tissue-engineered constructs (and method for making such constructs) that can be used to replace damaged organs for example kidney, heart, liver, spleen, pancreas, bladder, ureter and urethra.

(ii) Cells Produced from CiPSCs (Progeny)

The CiPSCs can be induced to differentiate into cells from any of the three germ layers, for example, skin and hair cells including epithelial cells, keratinocytes, melanocytes, adipocytes, cells forming bone, muscle and connective tissue such as myocytes, chondrocytes, osteocytes, alveolar cells, parenchymal cells such as hepatocytes, renal cells, adrenal cells, and islet cells (e.g., alpha cells, delta cells, PP cells, and beta cells), blood cells (e.g., leukocytes, erythrocytes, macrophages, and lymphocytes), retinal cells (and other cells involved in sensory perception, such as those that form hair cells in the ear or taste buds on the tongue), and nervous tissue including nerves.

(iii) Therapeutic Compositions

The CiPSCs can be formulated for administration, delivery or contacting with a subject, tissue or cell to promote de-differentiation in vivo or in vitrolex vivo. Additional factors, such as growth factors, other factors that induce differentiation or dedifferentiation, secretion products, immunomodulators, anti-inflammatory agents, regression factors, biologically active compounds that promote innervation, vascularization or enhance the lymphatic network, and drugs, can be incorporated.

The induced pluripotent cells can be administered to a patient by way of a composition that includes a population of CiPSCs or CiPSC progeny alone or on or in a carrier or support structure. In many embodiments, no carrier will be required. The cells can be administered by injection onto or into the site where the cells are required. In these cases, the cells will typically have been washed to remove cell culture media and will be suspended in a physiological buffer.

In other embodiments, the cells are provided with or incorporated onto or into a support structure. Support structures may be meshes, solid supports, scaffolds, tubes, porous structures, and/or a hydrogel. The support structures may be biodegradable or non-biodegradable, in whole or in part. The support may be formed of a natural or synthetic polymer, metal such as titanium, bone or hydroxyapatite, or a ceramic. Natural polymers include collagen, hyaluronic acid, polysaccharides, and glycosaminoglycans. Synthetic polymers include polyhydroxyacids such as polylactic acid, polyglycolic acid, and copolymers thereof, polyhydroxyalkanoates such as polyhydroxybutyrate, polyorthoesters, polyanhydrides, polyurethanes, polycarbonates, and polyesters. These may be in for the form of implants, tubes, meshes, or hydrogels.

Solid Supports

The support structure may be a loose woven or non-woven mesh, where the cells are seeded in and onto the mesh. The structure may include solid structural supports. The support may be a tube, for example, a neural tube for regrowth of neural axons. The support may be a stent or valve. The support may be a joint prosthetic such as a knee or hip, or part thereof, that has a porous interface allowing ingrowth of cells and/or seeding of cells into the porous structure. Many other types of support structures are also possible. For example, the support structure can be formed from sponges, foams, corals, or biocompatible inorganic structures having internal pores, or mesh sheets of interwoven polymer fibers. These support structures can be prepared using known methods.

The support structure may be a permeable structure having pore-like cavities or interstices that shape and support the hydrogel-cell mixture. For example, the support structure can be a porous polymer mesh, a natural or synthetic sponge, or a support structure formed of metal or a material such as bone or hydroxyapatite. The porosity of the support structure should be such that nutrients can diffuse into the structure, thereby effectively reaching the cells inside, and waste products produced by the cells can diffuse out of the structure The support structure can be shaped to conform to the space in which new tissue is desired. For example, the support structure can be shaped to conform to the shape of an area of the skin that has been burned or the portion of cartilage or bone that has been lost. Depending on the material from which it is made, the support structure can be shaped by cutting, molding, casting, or any other method that produces a desired shape. The support can be shaped either before or after the support structure is seeded with cells or is filled with a hydrogel-cell mixture, as described below.

An example of a suitable polymer is polyglactin, which is a 90:10 copolymer of glycolide and lactide, and is manufactured as VICRYL™ braided absorbable suture (Ethicon Co., Somerville, N.J.). Polymer fibers (such as VICRYL™), can be woven or compressed into a felt-like polymer sheet, which can then be cut into any desired shape. Alternatively, the polymer fibers can be compressed together in a mold that casts them into the shape desired for the support structure. In some cases, additional polymer can be added to the polymer fibers as they are molded to revise or impart additional structure to the fiber mesh. For example, a polylactic acid solution can be added to this sheet of polyglycolic fiber mesh, and the combination can be molded together to form a porous support structure. The polylactic acid binds the crosslinks of the polyglycolic acid fibers, thereby coating these individual fibers and fixing the shape of the molded fibers. The polylactic acid also fills in the spaces between the fibers. Thus, porosity can be varied according to the amount of polylactic acid introduced into the support. The pressure required to mold the fiber mesh into a desirable shape can be quite moderate. All that is required is that the fibers are held in place long enough for the binding and coating action of polylactic acid to take effect.

Alternatively, or in addition, the support structure can include other types of polymer fibers or polymer structures produced by techniques known in the art. For example, thin polymer films can be obtained by evaporating solvent from a polymer solution. These films can be cast into a desired shaped if the polymer solution is evaporated from a mold having the relief pattern of the desired shape. Polymer gels can also be molded into thin, permeable polymer structures using compression molding techniques known in the art.

Hydrogels

In another embodiment, the cells are mixed with a hydrogel to form a cell-hydrogel mixture. Hydrogels may be administered by injection or catheter, or at the time of implantation of other support structures. Crosslinking may occur prior to, during, or after administration.

V. Kits

Kits are provided which include the chemical inducers of pluripotency (CIP) disclosed herein. The CIPs are as described above. These may be in a form having defined concentrations to facilitate addition to cell culture media to produce a desired concentration. The kit may include directions providing desired concentration ranges and times of administration based on the types of cells to be induced. The kit may also include cell culture media which is pre-mixed with the CIPs for culture of cells to induce pluripotency.

The present invention will be further understood by reference to the following non-limiting examples.

EXAMPLES

Materials and Methods

Mice

The mouse strains C57BL/6J-Tg (GOFGFP) 11Imeg/Rbrc (OG), C57BL/6NCrlVr (C57), ICR and 129S2/SvPasCrlVr (129) were purchased as described by Li, *Cell Res.*, 21:196-204 (2011). The OG mice were mated with other strains to generate offspring carrying Oct4 promoter-driven GFP. Mouse strains including ICR, C57 X 129, OG X ICR, OG X 129 and OG X C57 were used to isolate primary mouse embryonic fibroblasts (MEFs), mouse neonatal fibroblasts (MNFs), mouse adult fibroblasts (MAFs) and adipose-derived stem cells (ADSCs). These cells were used for CiPSC induction. The neonatal mice used were 2-3 days old and the adult mice used were 7 weeks old. The Tet-On POU5F1 mouse strain B6; 129t (ROSA) 26Sortm1 (rtTA*M2) Jae Collaltm2 (tetO-Pou5f1) Jae/J was purchased from Jackson Laboratory (Hochedlinger, et al., *Cell*, 121:465-477 (2005)) and used only for reprogramming with Oct4 plus VC6T. Animal experiments were performed according to the Animal Protection Guidelines of Peking University, China.

Cell Culture

Primary MEFs were isolated as described by Takahashi, et al., *Cell*, 126:663-676 (2006)), with careful attention to the removal of the genital ridges. MNFs from skin, MAFs from lungs and ADSCs from inguinal fat pads were isolated as described by Lichti, et al., *Nat. Protoc.* 3:799-810 (2008); Seluanov, et al., *J. Vis. Exp.* 2010:2033 (2010); Tat, et al., *Cell Transplant.* 19:525-536 (2010) and McQualter, et al., *Stem Cells*, 27:623-633 (2009).

MEFs, MNFs, MAFs and ADSCs were cultured in DMEM/High Glucose (Hyclone) containing 10% fetal bovine serum (Hyclone). The cells used in reprogramming were from passages 1 to 5.

Mouse ESCs (R1 and TT2), iPSCs and CiPSCs were maintained on feeder layers of mitomycin C-treated MEFs in ESC culture medium (KnockOut DMEM (Invitrogen) containing 10% knockout serum replacement (Invitrogen), 10% fetal bovine serum (Hyclone), 2 mM GlutaMAX™-I (Invitrogen), 1% nonessential amino acids (Invitrogen), 0.1 mM 2-mercaptoethanol (Invitrogen), 1% penicillin-streptomycin (Invitrogen) and 1,000 U/ml leukemia inhibitory factor (LIF, Millipore)) or 2i-medium (ESC culture medium supplemented with 2i (3 µM CHIR99021 and 1 µM PD0325901)). The medium was changed daily. ESCs, iPSCs and CiPSCs were passaged by trypsin-EDTA (Invitrogen). For CiPSC induction, LIF-free ESC culture medium supplemented with 20-100 ng/ml bFGF (Origene) was used as the chemical reprogramming medium.

Fetal small intestinal epithelial cells were isolated from mouse embryonic small intestine at embryonic 13.5 day as previously described (Li et al., 2011), and cultured in Knockout™ DMEM (Invitrogen), supplemented with 10% fetal bovine serum (FBS; Pan-Biotech), 10% knockout serum replacement (KSR), 1% non-essential amino acids (NEAA), 2 mM GlutaMAX™-I (GlutaMAX), 10 U penicillin-streptomycin (PS), and 55 µM β-Mercaptoethanol (β-me) (all from Invitrogen).

Fetal neural stem cells (NSCs) were isolated from mouse forebrain at embryonic day 13.5 as previously described (Fischer et al., 2011), and postnatal NSCs were isolated from the subventricular zone of the postnatal mouse brain (Fischer et al., 2011; Guo et al., 2012). NSCs were cultured in NSC culture medium (DMEM/F-12 (1:1), DF12) containing N2 and B27 supplements, 1% NEAA, 2 mM GlutaMAX, 10 U PS, 55 µM β-me (all from Invitrogen), 25 ng/mL basic fibroblast growth factor (bFGF) (Origene), and 20 ng/mL epidermal growth factor (EGF) (R&D)), and passaged by accutase (Millipore) every 4-5 days. NSCs were single-cell suspended and formed neurospheres for 2-3 days. Mouse ESCs (R1) were maintained on feeder layers of mitomycin C-treated MEFs in 2i-medium plus LIF (Knockout™ DMEM containing 10% KSR, 10% FBS, 2 mM GlutaMAX, 1% NEAA, 55 UM β-me, 10 U PS (all from Invitrogen), 3 µM CHIR99021 (CHIR), 1 µM PD0325901 (PD03) and 10 ng/mL mouse leukemia inhibitory factor (mLIF; Millipore)). The medium was changed daily. ESCs and CiPSCs were passaged by trypsin-EDTA (Invitrogen).

For CiPSC induction, ESC culture medium without CHIR, PD03 and LIF supplemented with bFGF and Vc was used as chemical reprogramming medium. At the 2i-medium stage, the basal culture medium was DMEM/F12 plus N2 and B27 supplements (N2B27-2iL medium).

XEN Cell Derivation and Culture

Traditional eXEN (embryo-derived XEN) cell lines (gift from Dr. Rossant's laboratory) were cultured as previously described (Kunath et al., 2005). Briefly, eXEN cells were seeded on MEF feeders with RPMI1640 (Invitrogen) containing 20% fetal bovine serum, 2 mM GlutaMAX™-I (Invitrogen), 1% nonessential amino acids (Invitrogen), 0.1 mM 2-mercaptoethanol (Invitrogen), 1% penicillin-streptomycin (Invitrogen), and 1% sodium pyruvate (Invitrogen;

RPMI medium). For most experiments, eXEN cells were cultured in a feeder-free system, on gelatin (0.1% porcine skin gelatin, Sigma)-coated plates supplemented with 70% MEF-conditioned medium (RPMI-CM). Alternatively, eXEN could be cultured long-term in stage 1 medium (with VC6TFAE or VC6TF; with 20 ng/ml bFGF) on gelatin-coated plates (eXEN in VC6TF). Cells were routinely fed every 2 days and passaged at 1:20 to 1:30 every 3 days. eXEN were also derived directly from E3.5 blastocysts using stage 1 medium (with VC6TFAE or VC6TF; with 20 ng/ml bFGF; CeXEN). In brief, E3.5 blastocysts were plated on MEF feeders in stage 1 medium. The medium was changed every 2 days. Approximately 4-7 days (depending on the size of outgrowth) later, outgrowths could be disaggregated 1:1 to 1:2 onto new feeder cells. The medium was changed every 2 days, and XEN cells could grow to confluence in approximately 4-7 days. Then, CeXEN cells were routinely cultured in stage 1 medium and passaged 1:20-1:30 every 3 days. Three CeXEN cell lines were derived in this manner and were expanded long-term for more than 25 passages.

Small-Molecule Compounds and Libraries

The small-molecule compounds used in this study were purchased or synthesized as described in Table 1D. The concentration of compounds is shown in Table 1D. Small-molecule libraries used for the screen were purchased or generated in-house as described in Table 1C

TABLE 1C

Small molecule libraries used in reprograming

| Library | Source | Number of small-molecule compounds |
|---|---|---|
| BBP-2080NPs library | BioBioPha | 2,080 |
| The Spectrum Collection | MicroSource Disovery Systems | 2,000 |
| Sigma LOPAC ®,1280 | Sigma | 1,280 |
| Prestwick Chemical Library ® | Prestwick Chemical | 1,200 |
| Tocriscreen ™ Total | Tocris | 1,120 |
| US Drug Collection | MicroSource Discovery Systems | 1,040 |
| ICCB Known Bioactives Library | Enzo | 480 |
| Protein Kinase Inhibitor Library I, II, III | Millipone | 324 |
| StemSelect Small Molecule Regulations | Calbiochem | 303 |
| Nuclear Receptor Ligand Library | Enzo | 76 |
| Selected Small Molecules* | Our Lab | 88 |

*This library was generated in-house, including 88 selected small molecules related to pluripotency, reprogramming or epigenetic modification

TABLE 1D

Small-molecule compounds tested in reprogramming

| Full Name | Abbreviation | Concentration (μM) | Source | Molecular Weight | Structure |
|---|---|---|---|---|---|
| Valproic acid sodium salt | VPA, V | 500 | Sigma, cat. no. P4543 | 166.19 | 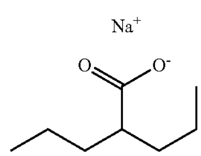 |
| CHIR99021 | CHIR, C | 10-20* | Synthesized by WUXI APPTEC | 465.34 | 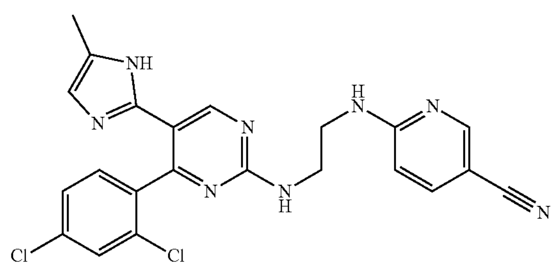 [SMILES: Cc1cnc(-c2cnc(NCCNc3ccc(C#N)cn3)nc2-c2ccc(Cl)cc2Cl)[nH]1] |
| 616452 | 6 | 5-10 | Synthesized by WUXI APPTEC | 287.12 | 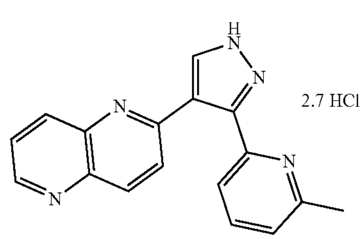 [SMILES: Cc1cccc(-c2n[nH]cc2-c2ccc3ncccc3n2)n1] |
| Tranylcypromine | Tranyl, T | 5-10 | Enzo, cat. no. BML-EI217-0005 | 182.23 | 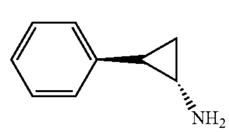 |

TABLE 1D-continued

Small-molecule compounds tested in reprogramming

| Full Name | Abbreviation | Concentration ($\mu M$) | Source | Molecular Weight | Structure |
|---|---|---|---|---|---|
| Forskolin | FSK, F | 10-50** | Enzo, cat. no. BML-CN100-0100 | 410.50 | 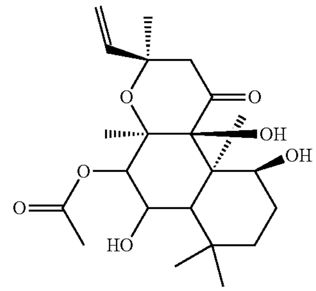 [SMILES: C=C[C@@]1(C)CC(=O)[C@@]2(O)[C@](C)(O1)C(OC(C)=O)C(O)C1C(C)(C)CC[C@H](O)[C@@]12C] |
| 3-deazaneplanocin A | DZNep, Z | 0.05-0.1 | Synthesized by WUXI APPTEC | 262.26 | |
| 2-Methyl-5-hydroxytryptamine hydrochloride | 2-Me-5HT, M | 5 | Synthesized by WUXI APPTEC | 233.99 | |
| D4476 | D | 5 | Synthesized by WUXI APPTEC | 398.41 | 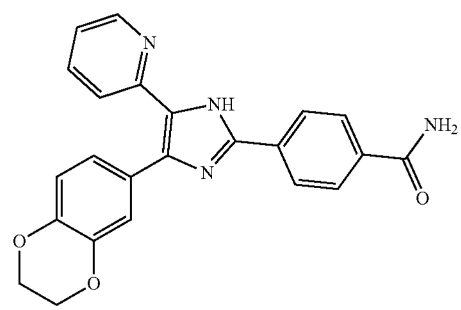 [SMILES: NC(=O)c1ccc(-c2nc(-c3ccc4c(c3)OCCO4)c(-c3ccccn3)[nH]2)cc1] |
| PD0325901 | | 1 | Synthesized by WUXI APPTEC | 482.00 | 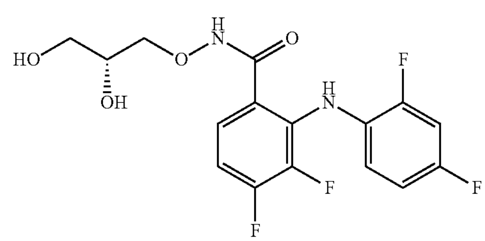 [SMILES: O=C(NOC[C@H](O)CO)c1ccc(F)c(F)c1Nc1ccc(F)cc1F] |
| Adenosine, periodate oxidized | Adox | 10 | Santa Cruz, cat. no. sc-214510 | 265.23 | 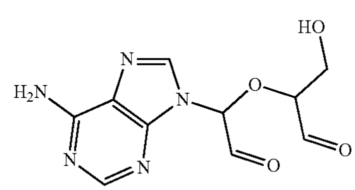 [SMILES: Nc1ncnc2c1ncn2C(C=O)OC(C=O)CO] |

TABLE 1D-continued

Small-molecule compounds tested in reprogramming

| Full Name | Abbreviation | Concentration (μM) | Source | Molecular Weight | Structure |
|---|---|---|---|---|---|
| IBMX | | 50 | Tocris, cat. no. 2845 | 222.24 | 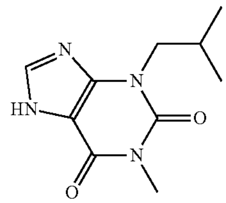 [SMILES: CC(C)Cn1c(=O)n(C)c(=O)c2[nH]cnc21] |
| Dibutyryl-cAMP | DBcAMP | 50 | Santa Cruz, cat. no. sc-201567 | 491.37 | 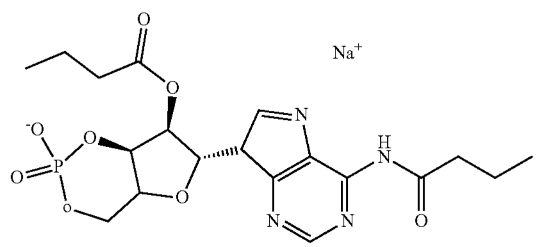 |
| 2',5'-Dideoxy-adenosine | 2'5'ddAdo | 5-20 | Santa Cruz, cat. no. sc-201562 | 235.2 | 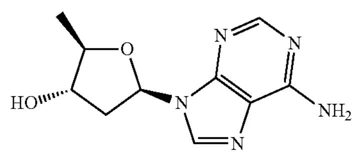 [SMILES: C[C@H]1O[C@@H](n2cnc3c(N)ncnc32)C[C@@H]1O] |
| Prostaglandin E2 | PGE2, P | 5 | Cayman, cat. no. 14010 | 352.46 | 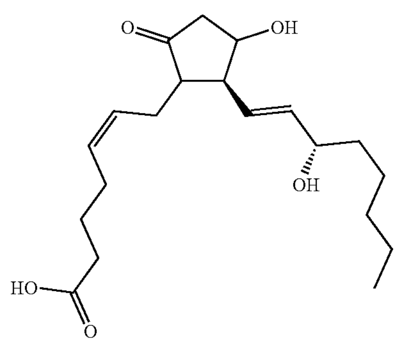 [SMILES: CCCCC[C@H](O)/C=C/[C@@H]1C(O)CC(=O)C1C/C=C\CCCC(=O)O] |
| Rolipram | | 10 | Tocris, cat. no. 0905 | 275.35 | 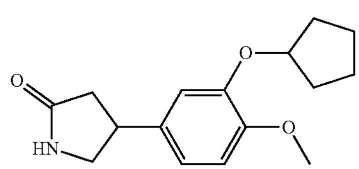 [SMILES: COc1ccc(C2CNC(=O)C2)cc1OC1CCCC1] |
| Sodium butyrate | NaB, B | 20 | Sigma, cat. no. B5887 | 110.09 | 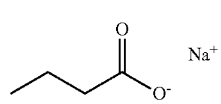 |
| SRT1720 | S | 1 | Selleck, cat. no. S1129 | 506.02 | 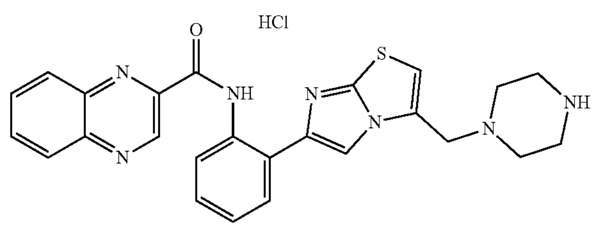 [SMILES: Cl ; O=C(Nc1ccccc1-c1cn2c(CN3CCNCC3)csc2n1)c1cnc2ccccc2n1] |

TABLE 1D-continued
Small-molecule compounds tested in reprogramming
| Full Name | Abbreviation | Concentration (μM) | Source | Molecular Weight | Structure |
|---|---|---|---|---|---|
| UNC0638 | UNC, U | 0.5 | Tocris, cat. no. 4343 | 509.73 | 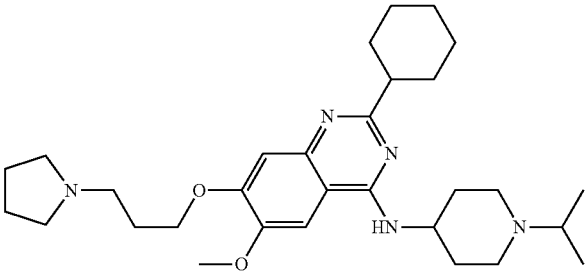 [SMILES: COc1cc2c(NC3CCN(C(C)C)CC3)nc(C3CCCCC3)nc2cc1OCCCN1CCCC1] |
| Ionomycin | | 4 | Calbiochem, cat. no. 407952 | 747.06 | 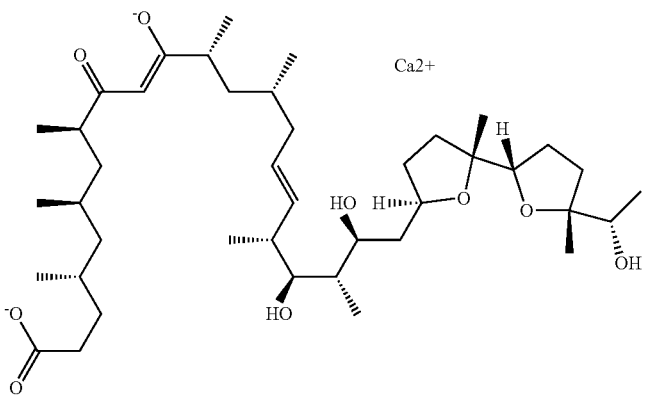 |
| BIX-01294 | | 1 | Stemgent, cat. no. 04-0002 | 490.64 | 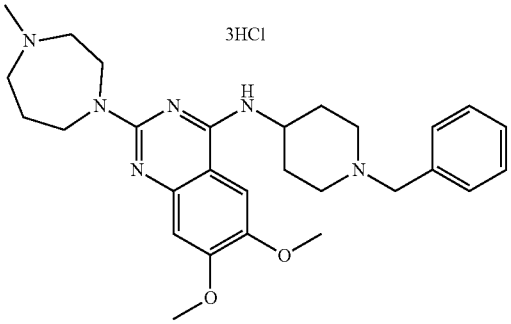 [SMILES: COc1cc2nc(N3CCCN(C)CC3)nc(NC3CCN(Cc4ccccc4)CC3)c2cc1OC] |
| (−)-Neplanocin A | Nep A | 1 | Cayman, cat. no. 10584 | 263.25 | 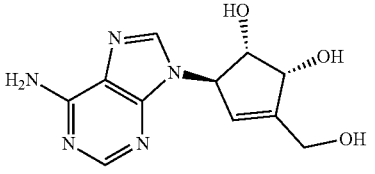 [SMILES: Nc1ncnc2c1ncn2[C@@H]1C=C(CO)[C@@H](O)[C@H]1O] |
| 3-Deazaadenosine | DZA | 10 | Cayman, cat. no. 9000785 | 266.25 | 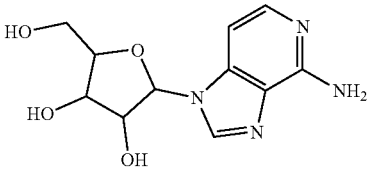 [SMILES: Nc1nccc2c1ncn2C1OC(CO)C(O)C1O] |

TABLE 1D-continued
Small-molecule compounds tested in reprogramming
| Full Name | Abbreviation | Concentration (μM) | Source | Molecular Weight | Structure |
|---|---|---|---|---|---|
| Budesonide | Bude | 5 | Tocris, cat. no. 2671 | 430.53 | 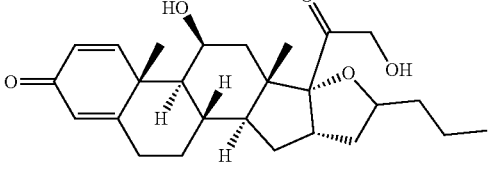 |
| RG108 | R | 20-40 | Tocris, cat. no. 3295 | 334.33 | 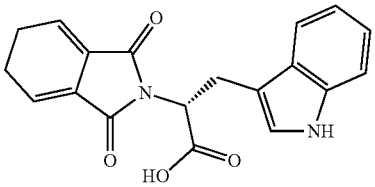 |
| 5-Azacytidine | 5-aza-C | 5 | Tocris, cat. no. 3842 | 244.2 | 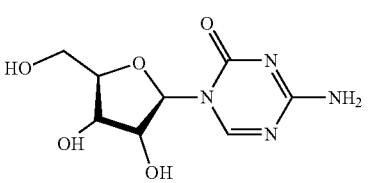 |
| Adenine | | 2 | Calbiochem, cat. no. 1152 | 135.13 | 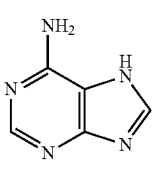 |
| Adenosine | | 2 | Calbiochem, cat. no. 1160CBC | 267.24 | 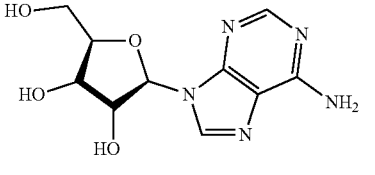 |
| SF1670 | | 1 | Cellagen Technology, cat. no. C7316-2s | 307.34 | 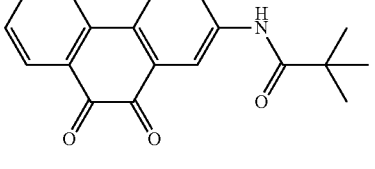 |
| DY131 | | 5 | Tocris, cat. no. 2266 | 311.38 | 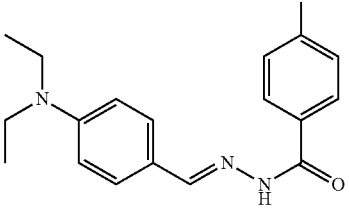 |
| Nimesulide | | 2 | Tocris, cat. no. 2470 | 308.31 | 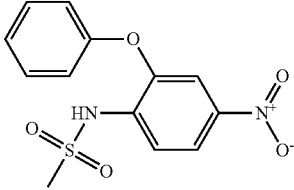 [SMILES: CS(=O)(=O)Nc1ccc([N+](=O)[O-])cc1Oc1ccccc1] |

TABLE 1D-continued

Small-molecule compounds tested in reprogramming

| Full Name | Abbreviation | Concentration (μM) | Source | Molecular Weight | Structure |
|---|---|---|---|---|---|
| Resveratrol | | 3 | Tocris, cat. no. 1418 | 228.25 | 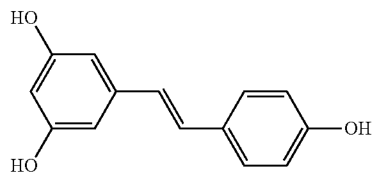 [SMILES: Oc1ccc(/C=C/c2cc(O)cc(O)c2)cc1] |
| TTNPB | N | 1 | Tocris, cat. no. 0761 | 348.48 | 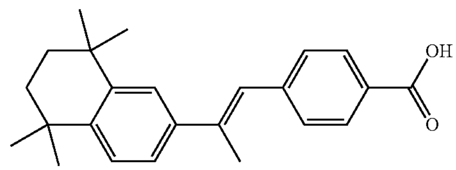 [SMILES: C/C(=C\c1ccc(C(=O)O)cc1)c1ccc2c(c1)C(C)(C)CCC2(C)C] |

Note: * For CiPSCs induction from MEFs, the concentration of CHIR99021 was 10 μM. For CiPSCs induction from MNFs, MAFs or ADSCs, and CiPSCs induction without replacing, the concentration CHIR99021 was elevated to 20 μM during day 0-12.
** For CiPSCs induction from MEFs, the concentration of Forskolin was 10 μM. For CiPSCs induction from MNFs, MAFs or ADSCs, the concentration of Forskolin was elevated to 50 μM during day 0-12

Plasmid Construction and Lentivirus Production

The pLL3.7-ΔU6 vector was described by (McQualter, et al., *Stem Cells*, 27:623-633 (2009). Mouse Sall4 was amplified from ESCs (TT2) by RT-PCR, cloned into the pEASY-Blunt vector (TransGen Biotech), confirmed by sequencing and then introduced into the XhoI/EcoRI sites of pLL3.7-ΔU6. The primers are listed in Table 2.

TABLE 2

Primer sets for PCR reactions

| Genes | Forward (5' to 3') | Reverse (5' to 3') |
|---|---|---|
| *For plasmid construction* | | |
| Sall4 | ACTCGAGCCACCATGTCGAGG CGCAAGCAGGCGAA (SEQ ID NO: 1) | GCAATTGTTAGCTGACAGC AATCTTATTTTCCTCC (SEQ ID NO: 2) |
| *For qRT-PCR* | | |
| Sox2 | CGGGAAGCGTGTACTTATCCT T (SEQ ID NO: 3) | GCGGAGTGGAAACTTTTGT CC (SEQ ID NO: 4) |
| Klf4 | TTGCGGTAGTGCCTGGTCAGT T (SEQ ID NO: 5) | CTATGCAGGCTGTGGCAAA ACC ( SEQ ID NO: 6) |
| Oct4 | CAGGGCTTTCATGTCCTGG (SEQ ID NO: 7) | AGTTGGCGTGGAGACTTTG C (SEQ ID NO: 8) |
| Gata4 | GAGCTGGCCTGCGATGTCTGA GTG (SEQ ID NO: 9) | AAACGGAAGCCCAAGAACC TGAAT (SEQ ID NO: 10) |
| Gata6 | TGAGGTGGTCGCTTGTGTAG (SEQ ID NO: 11) | ATGGCGTAGAAATGCTGAG G (SEQ ID NO: 12) |
| Sox17 | GTCAACGCCTTCCAAGACTTG (SEQ ID NO: 13) | GTAAAGGTGAAAGGCGAGG TG (SEQ ID NO: 14) |
| Esrrb | GTGGCTGAGGGCATCAATG (SEQ ID NO: 15) | AACCGAATGTCGTCCGAAG AC (SEQ ID NO: 16) |
| Sall4 | TGGCAGACGAGAAGTTCTTTC (SEQ ID NO: 17) | TCCAACATTTATCCGAGCA CAG (SEQ ID NO: 18) |
| Lin28a | CCGCAGTTGTAGCACCTGTCT (SEQ ID NO: 19) | GAAGAACATGCAGAAGCGA AGA (SEQ ID NO: 20) |
| Dppa2 | GCGTAGCGTAGTCTGTGTTTG (SEQ ID NO: 21) | TCAACGAGAACCAATCTGA GGA (SEQ ID NO: 22) |
| Nanog | AGTTATGGAGCGGAGCAGCAT (SEQ ID NO: 23) | AGGCCTGGACCGCTCAGT (SEQ ID NO: 24) |
| Actb | CATTGCTGACAGGATGCAGAA GG (SEQ ID NO: 25) | TGCTGGAAGGTGGACAGTG AGG (SEQ ID NO: 26) |
| Gadph | CATCACTGCCACCCAGAAGAC TG (SEQ ID NO: 27) | ATGCCAGTGAGCTTCCCGT TCAG (SEQ ID NO: 28) |
| *For genomic PCR* | | |
| pLL-Oct4 | GAAGGATGTGGTCCGAGT (SEQ ID NO: 29) | GCAGCGTATCCACATAGCG T (SEQ ID NO: 30) |
| pLL-Sox2 | CATGGGTTCGGTGGTCAA (SEQ ID NO: 31) | GCAGCGTATCCACATAGCG T (SEQ ID NO: 32) |
| pLL-Klf4 | ACCACTGTGACTGGGACG (SEQ ID NO: 33) | GCAGCGTATCCACATAGCG T (SEQ ID NO: 34) |
| pLL-cMyc | TACATCCTGTCCGTCCAAGC (SEQ ID NO: 35) | GCAGCGTATCCACATAGCG T (SEQ ID NO: 36) |
| Fu-tet-hOct4 | ACCTCCATAGAAGACACCG (SEQ ID NO: 37) | TAGCCCCACTCCAACCTG (SEQ ID NO: 38) |
| Fu-tet-hSox2 | ACCTCCATAGAAGACACCG (SEQ ID NO: 39) | CTCCGACAAAAGTTTCCAC TCG (SEQ ID NO: 40) |

TABLE 2-continued

Primer sets for PCR reactions

| Genes | Forward (5' to 3') | Reverse (5' to 3') |
|---|---|---|
| Fu-tet-hKlf4 | ACCTCCATAGAAGACACCG (SEQ ID NO: 41) | GAAGAGGAGGCTGACGCT (SEQ ID NO: 42) |
| Fu-tet-hcMyc | ACCTCCATAGAAGACACCG (SEQ ID NO: 43) | GGGTCGCAGATGAAACTC (SEQ ID NO: 44) |

For bisulfite genomic sequencing

| Oct4 | GGAGTGGTTTTAGAAATAATTG (SEQ ID NO: 45) | TCCAACCCTACTAACCCATCACC (SEQ ID NO: 46) |
|---|---|---|
| Nanog | GATTTTGTAGGTGGGATTAATTGTGAATTT (SEQ ID NO: 47) | ACCAAAAAAACCCACACTCATATCAATATA (SEQ ID NO: 48) |

For chromatin immunoprecipitation

| Oct4 | CTGTAAGGACAGGCCGAGAG (SEQ ID NO: 49) | CAGGAGGCCTTCATTTTCAA (SEQ ID NO: 50) |
|---|---|---|
| Nanog | CTATCGCCTTGAGCCGTTG (SEQ ID NO: 51) | AACTCAGTGTCTAGAAGGAAAGATCA (SEQ ID NO: 52) |
| Sox2 | TTTATTCAGTTCCCAGTCCAA (SEQ ID NO: 53) | TTATTCCTATGTGTGAGCAAGA (SEQ ID NO: 54) |

For OG (Oct4 promoter-driven GFP) cassette

| OG | AACCACTACCTGAGCACCC (SEQ ID NO: 55) | ACCTCTACAAATGTGGTATG (SEQ ID NO: 56) |
|---|---|---|

The lentiviral vectors containing the other individual reprogramming factors (Oct4, Sox2, Klf4 or c-Myc) were described by Zhao, et al., *Cell Stem Cell*, 3:475-479 (2008). For tet-on Oct4 systems, Fu-tet-hOct4 and FUdeltaGW-rtTA were the same as described by Li, et al., *Cell Res.*, 21:196-204 (2011); Maherali, et al., *Cell Stem Cell*, 3:340-345 (2008). Genetic knockdown was carried out using shRNAs (SIGMA MissionR shRNA) according to the manufacturer's protocol. The shRNA sequences are listed in Table 3. Lentivirus production, collection and infection were as described by Zhao, et al., *Cell Stem Cell*, 3:475-479 (2008).

TABLE 3

Sequences of shRNAs

| | shRNA | Sequences (5'-3') |
|---|---|---|
| Sall4 | shRNA 1 | CCGGCAGCCCACCTTTGTCAAAGTTCTCGAGAACTTTGACAAAGGTGGGCTGTTTTG (SEQ ID NO: 57) |
| | shRNA 2 | CCGGGCCCACCTTTGTCAAAGTTGACTCGAGTCAACTTTGACAAAGGTGGGCTTTTTG (SEQ ID NO: 58) |
| Gata4 | shRNA 1 | CCGGAGCCCAAGAACCTGAATAAATCTCGAGATTTATTCAGGTTCTTGGGCTTTTTG (SEQ ID NO: 59) |
| | shRNA 2 | CCGGCATCTCCTGTCACTCAGACATCTCGAGATGTCTGAGTGACAGGAGATGTTTTG (SEQ ID NO: 60) |
| Gata6 | shRNA 1 | CCGGCCACTACCTTATGGCGTAGAACTCGAGTTCTACGCCATAAGGTAGTGGTTTTG (SEQ ID NO: 61) |
| | shRNA 2 | CCGGCCTCGACCACTTGCTATGAAACTCGAGTTTCATAGCAAGTGGTCGAGGTTTTG (SEQ ID NO: 62) |
| Sox17 | shRNA 1 | CCGGCCCACAATCACTGTCCAGTTTCTCGAGAAACTGGACAGTGATTGTGGGTTTTG (SEQ ID NO: 63) |
| | shRNA 2 | CCGGCGCACGGAATTCGAACAGTATCTCGAGATACTGTTCGAATTCCGTGCGTTTTG (SEQ ID NO: 64) |
| Ezh2 | shRNA 1 | CCGGGCTAGGCTAATTGGGACCAAACTCGAGTTTGGTCCCAATTAGCCTAGCTTTTT (SEQ ID NO: 65) |
| | shRNA 2 | CCGGCGGCTCCTCTAACCATGTTTACTCGAGTAAACATGGTTAGAGGAGCCGTTTTG (SEQ ID NO: 66) |
| Control | shRNA control | CCGGCAACAAGATGAAGAGCACCAACTCGAGTTGGTGCTCTTCATCTTGTTGTTTTT (SEQ ID NO: 67) |

CiPSC Induction
CiPSC Induction without Selective Priming for XEN-Like Cell Population The initial cells (MEFs, MNFs, MAFs or ADSCs) were seeded at a density of 50,000 cells per well of a 6-well plate or 300,000 cells per 100 mm dish. On the next day (day 0), the original medium was replaced with chemical reprogramming medium containing the small-molecule combinations. The small-molecule combinations-containing medium was changed every 4 days. On day 12, these cells were washed in PBS and digested with 0.25% Trypsin-EDTA (Invitrogen) at 37° C. for 3-5 min. After neutralization, the cell clumps were dissociated into single cells by thorough pipetting. The cells were harvested (300,000-1,000,000 cells per well of a 6-well plate) and replated at a density of 300,000-500,000 cells per well of a 6-well plate in the chemical reprogramming medium containing the small-molecule combinations. DZNep was added to the cell cultures on day 16 or day 20. On day 28-36, the small-molecule combinations including DZNep were removed. Meanwhile, the chemical reprogramming medium was replaced with 2i-medium. After another 8-12 days, 2i-competent, ESC-like and GFP-positive colonies were counted as primary CiPSC colonies. For CiPSC induction from wild-type cells without OG reporter, 2i-competent and ESC-like colonies were counted as primary CiPSC colonies. These CiPSC colonies were picked up for expansion and characterization. Alternatively, CiPSCs could be induced without replating on day 12.

IEC-CiPSC Induction

The initial IECs were seeded at a density of 100,000 cells per well of a 12-well plate. On the next day (day 0), the medium was replaced with chemical reprogramming medium containing the small-molecule cocktail (0.5 mM VPA, 20 µM CHIR, 10 µM 616452, 10 µM Tranylcypromine, 50 M Forskolin, 0.05 UM AM 580) and changed every 4 days. From day 12, 0.01 µM DZnep was added into chemical reprogramming medium, and AM 580 is withdrawn. The medium was replaced with N2B27-2iL medium from day 32. After another 12 days, 2i-competent, ESC-like and OG-positive colonies were counted as primary CiPSC colonies. The primary CiPSC colonies were picked up for expansion and further characterization.

NSC-CiPSC Induction

The initial NSCs were seeded at the density of 50,000 cells per well of a 6-well plate. The original culture medium was replaced by chemical reprogramming medium containing the small-molecule cocktail (0.5 mM VPA, 15 µM CHIR, 5 µM 616452, 10 µM Tranylcypromine, 20 µM Forskolin, 1 µM Ch 55, 5 µM EPZ) and changed every 4 days. From day 20, 0.01 µM DZNep was added into the chemical reprogramming medium. The medium was replaced with N2B27-2iL medium from day 40-44. After another 12 days, 2i-competent, ESC-like and OG-positive colonies were counted as primary CiPSC colonies. The primary CiPSC colonies were picked up for expansion and further characterization.

CiPSC Induction Via Selective Priming/Bias for XEN-Like Cell Population

The induction medium was prepared as following: The basal medium of stage 1 and stage 2 were LIF-free ESC culture medium containing 100 ng/ml and 20 ng/ml bFGF (Origene), respectively. The stage 3 medium was an N2B27-2i medium. The N2B27-2i medium (500 ml) was generated including the following: 240 ml DMEM/F12 (Invitrogen), 240 ml Neurobasal (Invitrogen), 5 ml N2 supplement (Invitrogen), 10 ml B27 supplement (Invitrogen), 2 mM GlutaMAX™-I (Invitrogen), 1% nonessential amino acids (Invitrogen), 0.1 mM 2-mercaptoethanol (Invitrogen), 1% penicillin-streptomycin (Invitrogen), 3 µM CHIR99021, 1 µM PD0325901 and 1,000 U/ml LIF.

MEFs, MNFs or MAFs were plated at 300,000 cells per 100 mm dish, or 50,000 cells per well on a 6-well plate. The next day (day 0), the culture was changed into stage 1 medium supplemented with small-molecule cocktail VC6TFAE (0.5 mM VPA, 20 PM CHIR99021, 10 µM 616452, 5 µM Tranylcypromine, 50 M FSK, 0.05 µM AM580 and 5 µM EPZ004777). On day 12, the cells were washed in PBS and digested with 0.25% Trypsin-EDTA (Invitrogen) at 37° C. for 2-3 min. After neutralization, the cell clumps were dissociated into single cells by thorough pipetting. The cells were harvested and then re-plated at 100,000 cells per well of a 6-well plate (1:15). During days 12-16, the cells were cultured in stage 1 medium supplemented with a modified small-molecule cocktail VC6TFA (0.5 mM VPA, 10 µM CHIR99021, 10 µM 616452, 5 µM Tranylcypromine, 10 µM FSK, 0.05 µM AM580). On day 16, XEN-like epithelial colonies were formed and the culture was changed into stage 2 medium supplemented with small-molecule cocktail VC6TFAZDS (0.5 mM VPA, 10 µM CHIR99021, 10 µM 616452, 5 µM Tranylcypromine, 10 µM FSK, 0.05 µM AM580, 0.05 µM DZNep, 0.5 µM 5-aza-dC and 5 µM SGC0946). On day 28, the culture was transferred into stage 3 medium. After another 8-12 days, 2i-competent, ESC-like and GFP-positive (if using pOct4-GFP reporter) CiPSC colonies emerged and were then picked up for expansion and characterization. During CiPSC induction, the medium and small molecules were changed every 4 days.

Chemical Reprogramming of eXEN Cells eXEN cells or CeXEN cells were plated at 2,000-10,000 cells per well of a 12-well plate on MEF feeders. Following the treatment with stage 1 medium for 4 days (dispensable for induction), stage 2 medium for 12 days and stage 3 medium for another 8-12 days, 2i-competent, ESC-like CiPSC colonies emerged and were then picked up for expansion and characterization. For most experiments, feeder cells were helpful for the survival of XEN cells, and a relatively low cell density was beneficial for CiPSC induction.

Plasmid Construction and Lentivirus Production

Plasmids were constructed as previously described (Zhao et al., 2008). Briefly, SALL4, GATA4 and GATA6 were amplified by qRT-PCR, cloned into the pEASY-Blunt vector (TransGen Biotech), confirmed by sequencing and then introduced into the XhoI/EcoRI sites of pLL3.7-ΔU6. The primers are listed in Table 4.

TABLE 4

Primers for plasmid construction

| SYMBOL | ACCESSION NUMBERS | PRIMERS (5' to 3') |
| --- | --- | --- |
| SALL4 | NM_020436 | TACTCGAGGCCACCATGTCGAGGCGCAAGCAG G (SEQ ID NO: 68) |
|  |  | GGGAATTCATCACAAAGCAGCATAGCAACAAT CGTG (SEQ ID NO: 69) |
| GATA4 | NM_002052 | ACCTCGAGGCCACCATGTATCAGAGCTTGGCC ATGGC (SEQ ID NO: 70) |
|  |  | GCGAATTCATCATTACGCAGTGATTATGTCCC CGTG (SEQ ID NO: 71) |

TABLE 4-continued

Primers for plasmid construction

| SYMBOL | ACCESSION NUMBERS | PRIMERS (5' to 3') |
|---|---|---|
| GATA6 | NM_005257 | ATCTCGAGGCCACCATGGCCTTGACTGACGGC GG (SEQ ID NO: 72) |
| | | CTGAATTCATCATCAGGCCAGGGCCAGGGC (SEQ ID NO: 73) |

Fu-tet-hSOX2 and FUdeltaGW-rtTA were described previously (Li et al., 2011; Maherali et al., 2008). Genetic knockdown, lentivirus production and infection were also the same as previously described (Hou et al., 2013).

Immunofluorescence, RT-PCR, Genomic PCR, Teratoma Formation and Karyotype Analysis Immunofluorescence, RT-PCR, genomic PCR and teratoma formation were all carried out as described in Hou, et al., Science, 341:651-654 (2013). For immunofluorescence, the primary antibodies included SSEA-1 (Millipore, MAB4301), OCT4 (Abcam, ab18976), SOX2 (Santa Cruz, sc-17320), KLF4 (Santa Cruz, sc-20691), REX1 (Santa Cruz, sc-99000), NANOG (R&D, AF2729), UTF1 (Abcam, ab24273), SALL4 (Santa Cruz, sc-166033). Secondary antibodies were Rhodamine-conjugated, including Donkey Anti Mouse IgG (H+L) (Jackson ImmunoResearch, 715-025-150), Donkey Anti Goat IgG (H+L) (Jackson ImmunoResearch, 705-025-147), and Donkey Anti Rabbit IgG (H+L) (Jackson ImmunoResearch, 711-025-152). Primers for RT-PCR were the same as described previously (Li, et al., Cell Res., 21:196-204 (2011)). Primers for genomic PCR are shown in Table 2. Karyotype analyses were performed as reported (Longo, et al., Transgenic Res. 6:321-328 (1997)).

For the imaging analysis, the cells were imaged using the Andor's Revolution WD spinning disk confocal microscopy system (Andor) or ImageXpress Micro XL Widefield High Content Screening System (Molecular Devices).

Real-Time PCR

Total RNA from an entire well of cultured cells was isolated using the RNeasy Plus MiniKit (QIAGEN). For a single colony, RNA was isolated using the RNeasy Micro Kit (QIAGEN). RNA was converted to cDNA using TransScript First-Strand cDNA Synthesis SuperMix (TransGen Biotech). PCR was carried out using Power SYBRR Green PCR Master Mix (Applied Biosystems) and performed on an ABI Prism 7300 Sequence Detection System. The data were analyzed using the delta-delta Ct method. The primers used for real-time PCR are listed in Table 2.

Chimera Construction

Chimeric mice were obtained by the injection of CiPS cells into blastocysts using a sharp injection needle or into eight-cell embryos using a XY Clone laser system (Hamilton ThorneBioscience). For blastocyst injection, 10-15 CiPS cells were injected into the recipient embryo cavity of F2 (intercross of B6D2F1) or CD-1 (albino) female mice at 3.5 d (days postcoitum). Host eight-cell embryos were collected from female mice at 2.5 d, and 7-10 CiPS cells were injected into each embryo. After injection, blastocysts and eight-cell embryos (6-8 embryos in each oviduct or horn of the uterus) were transferred into 2.5 d or 0.5 d pseudopregnant CD-1 females, respectively. Chimeric mice were identified by coat color and then assessed for germline transmission by mating with ICR mice.

XEN Chimera Assay

GFP-labeled XEN-like cells were induced from the GFP-labeled MEF isolated from GFP (ICR X ICR) mice. For chimera test, GFP-labeled XEN-like cell colonies were picked and disaggregated to single cells by 0.25% trypsin-EDTA. Approximately 10 to 15 XEN-like cells were injected into blastocysts and transferred to the uterus of E2.5 pseudopregnant females. Chimera conceptus between E6.5-8.5 were dissected carefully to keep the parietal yolk sac intact and observed with fluorescence stereoscopy. For the chimera test with eXENs and CeXENs, cells were infected with lentiviral vectors expressing EGFP and FASC sorted for the purification of EGFP-positive cells.

DNA Microarray and RNA-Seq

Total mRNA was isolated from mouse fibroblasts, CiPSCs and ESCs. Microarrays were performed as reported by Li, et al., Cell Res., 21:196-204 (2011). RNA sequencing libraries were constructed using the Illumina mRNA-seq Prep Kit (Illumina). Fragmented and randomly primed 200 bp paired-end libraries were sequenced using Illumina HiSeq 2000. Hierarchical clustering of the microarray data was performed as reported by Li, et al., Cell Res., 21:196-204 (2011). Heatmaps were generated using R (Bioconductor). In some studies, total RNA was isolated using the RNeasy Plus Mini Kit (Qiagen). RNA sequencing libraries were constructed using the NEBNext® Ultra™ RNA Library Prep Kit for Illumina® (NEB). Fragmented and randomly primed 200 bp paired-end libraries were sequenced using Illumina HiSeq 2500. Hierarchical clustering, scatter plots and heatmaps were generated in R v3.2.0 using the amap package, the graphics package and the pheatmap package, respectively.

Bisulfite Genomic Sequencing

Genomic DNA was modified by bisulfite treatment and purified using the MethylCode™ Bisulfite Conversion Kit (Invitrogen) according to the manufacturer's protocol. The primers are listed in Table 2. The amplified fragments were cloned into the pEASY-blunt Vector (Transgene). Ten randomly picked clones from each sample were sequenced.

cAMP, S-Adenosylmethionine (SAM) and S-Adenosylhomocysteine (SAH) Quantification CAMP was quantified using the Direct cAMP ELISA Kit (Enzo) according to the manufacturer's protocol. For SAM and SAH quantification, cultured cells (1,000,000 cells) were trypsinized and homogenized by ultrasonication in 200 µl PBS. Then 40 µl of 400 mg/ml TCA was added. Cell extracts were incubated on ice for 30 min. After centrifugation at 4° C. (13,000 rpm, 15 min), the supernatants were filtered through a 0.22 µm filter and analyzed by high-performance liquid chromatography (HPLC, Shimadzu) with HILIC columns (Waters).

Comparative Genomic Hybridization (CGH) Analysis.

For CGH experiments, genomic DNA was extracted and hybridized to NimbleGen 3×720K mouse whole-genome tiling arrays by Imagenes using C57BL/6 MEF DNA as a reference (Gene BioDesign).

Flow Cytometry Analysis

Cultured cells were trypsinized into single cells and then resuspended in PBS containing 3% fetal bovine serum. Using endogenous Oct4-GFP, FACS analyses were performed with a FACSCalibur instrument (BD Biosciences). The data were analyzed with FCS Express 4 (De Novo).

Chromatin Immunoprecipitation (ChIP)

ChIP was performed using the EZ-Magna ChIP A/G Kit (Millipore) according to the manufacturer's protocol. Anti-H3K27me3 (Abcam, ab6002), anti-H3K9me2 (Millipore, 07-441), anti-H3K4me3 (Abcam, ab8580) and anti-H3K9ac (Abcam, ab4441) antibodies were used. Following immunoprecipitation, DNA was analyzed by real-time PCR. The primers used are listed in Table 2.

Southern Blot

Southern blot was performed with the DIG High Prime DNA Labeling and Detection Starter Kit II (Roche, 11 585 614 910), with reference to "Roche Techniques for Hybridization of DIG-labeled Probes to a Blot". 20 µg genomic DNA isolated from iPS cells or MEFs was digested with EcoRI and XbaI. The DNA probe was designed based on psi sequence, which is present in the pLL3.7-_U6 vector and Fu-tet vectors and could thus be integrated into the genome along with exogenous transgenes after virus infection.

Luciferase Activity Assays

MEFs were plated at a density of 40,000 cells per well of a 24-well plate and transiently transfected with Oct4 promoter reporters using Lipofectamine LTX & Plus Reagent (Invitrogen) according to the manufacturer's instructions. pRL-TK plasmids (Promega) were cotransfected in each well as internal references, and the total DNA concentrations for all transfections were equalized by adding empty pLL3.7-_U6 vector. At 48 hours after transfection, cells were washed in PBS and lysed in passive lysis buffer (Promega). Luciferase activity was measured with the Dual-luciferase Reporter Assay System (Promega) using a Centro LB960 96-well luminometer (Berthold Technologies) and normalized to Renilla luciferase activity. Empty expression vector plasmids were used as negative control. The fold activation describes the ratio of firefly to Renilla luciferase activity for each condition compared with that of the empty vector control.

Western Blot Analysis

Cells were cultured in 100 mm dishes, washed in PBS and scraped in lysis buffer. Aliquots were loaded onto an 8-10% SDS-polyacrylamide gel and blotted onto a nitrocellulose membrane. Membranes were incubated overnight at 4° C. with rabbit anti-EZH2 (Abcam, ab3748) at a dilution of 1:1000. Goat anti Rabbit IgG (H+L)/HRP (ZSBIO, ZB-2301) was used as the secondary antibody. Detection was performed using SuperSignal West Pico solutions (Pierce).

Example 1: Chemical Substitutes for Oct 4

To identify chemical substitutes of Oct4, MEFs from OG mice were plated at a density of 20,000 cells per well of a 12-well plate and infected with lentiviruses encoding Sox2, Klf4 and c-Myc. After infection, the medium was replaced with LIF-free ESC culture medium. Individual chemicals from small-molecule libraries were added to each well. The medium and chemicals were changed every 4 days. Chemical treatments were continued for 14-20 days or until GFP-positive colonies appeared. Primary hits were selected for further confirmation and optimization.

Small molecules that enable reprogramming in the absence of Oct4 were searched using Oct4 promoter-driven green fluorescent protein (GFP) expression (OG) mouse embryonic fibroblasts (MEFs), with viral expression of Sox2, Klf4, and c-Myc. After screening up to 10,000 small molecules (Table 1C), Forskolin (FSK), 2-methyl-5-hydroxytryptamine (2-Me-5HT), and D4476 (Table 1D) were identified as chemical "substitutes" for Oct4 (FIG. 1A to 1F).

Figure 1A:
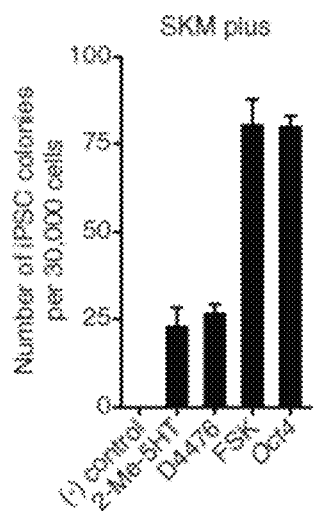
FIGS. 1A and 1B show the numbers of iPSC colonies induced from MEFs infected by SKM (FIG. 1A) or SK (FIG. 1B) plus chemicals or Oct4. Error bars, mean±SD (n=3 biological repeat wells).
Figure 1B:
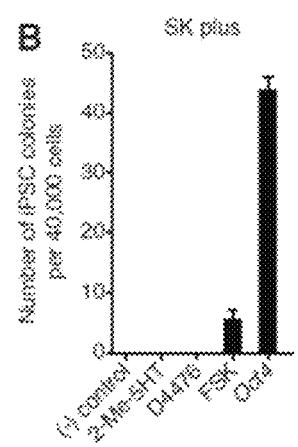
Figure 1C:
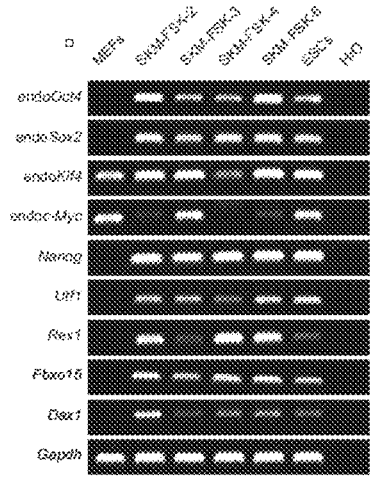
FIG. 1C shows RT-PCR analysis of pluripotency marker genes in MEFs, SKM-FSK-iPSCs and ESCs (R1).
Figure 1D:
FIG. 1D shows genomic PCR analysis of SKM-FSK-iPSCs and SK-FSK-iPSCs.
Figure 1E:
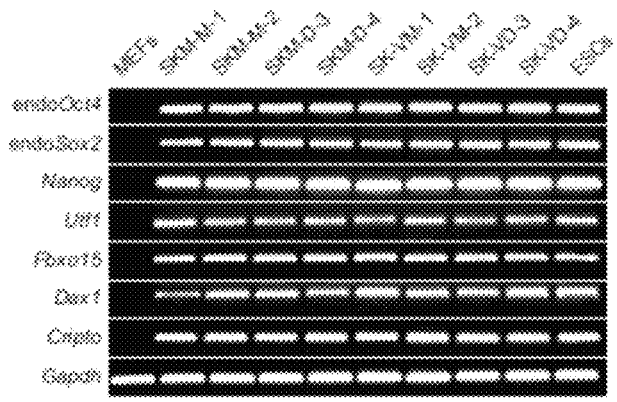
FIGS. 1E and 1F show JRT-PCR (FIG. 1E and genomic PCR (FIG. 1F) analysis of iPSC colonies induced by SKM or SK with chemicals treatment. Abbreviations: M (2-Me-5HT); D (D4476); V (VPA); Tg indicates exogenously introduced genes. Scale bars, 100 μM.
Figure 1F:
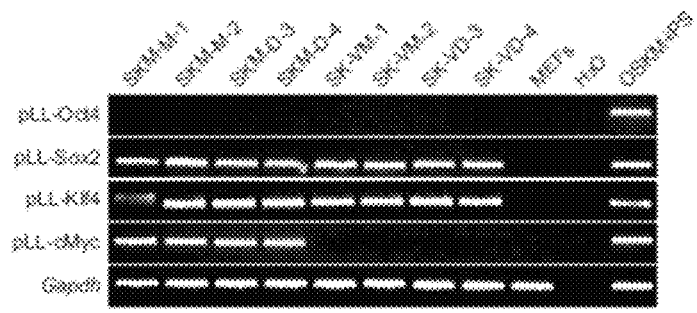

Passaged SKM-FSK-iPSCs exhibit typical ESC morphology and homogeneously express GFP (FIG. 1B). The SKM-FSK-iPSCs can contribute to chimeric mice, including gonadal tissues. Similarly, iPSCs induced by SKM with 2-Me-5HT treatment can contribute to chimeric mice.

Figure 2:
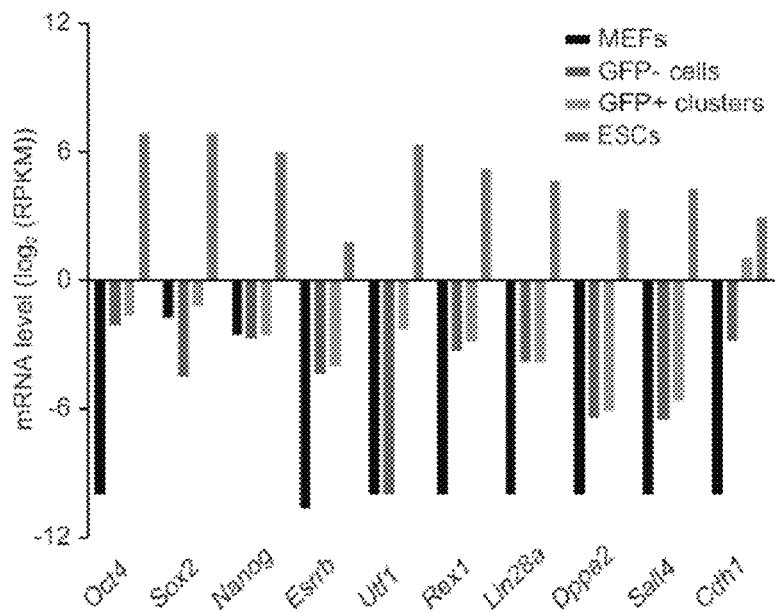
FIG. 2 shows mRNA levels of pluripotency-related genes detected by RNA-seq analysis in MEFs, GFP-negative cells, GFP-positive clusters and ESCs (R1). GFP-negative cells and GFP-positive clusters were collected on day 24. Cdh1=E-cadherin.

A small molecule combination "VC6T" [VPA, CHIR99021 (CHIR), 616452, tranylcypromine], that enables reprogramming with a single gene, Oct4 (Li, et al., Cell Res., 21:196-204 (2011)), was used next to treat OG-MEFs plus the chemical substitutes of Oct4 in the absence of transgenes. The data shows that VC6T plus FSK (VC6TF) induced some GFP-positive clusters expressing E-cadherin, a mesenchyme-to-epithelium transition marker, reminiscent of early reprogramming by transcription factors (Li, et al., Cell Stem Cell, 7:51-63 (2010); Samavarchi-Tehrani, et al., Cell Stem Cell, 7:64-77 (2010)) (FIG. 2). However, the expression of Oct4 and Nanog was not detectable, and their promoters remained hypermethylated, suggesting a repressed epigenetic state (FIGS. 2A and 2B).

Example 2: Small Molecules that Facilitate Late Reprograming

To identify small molecules that facilitate late reprogramming, a doxycycline (DOX)-inducible Oct4 expression screening system was used (Li, et al., Cell Res. 21:196-204 (2011)).

MEFs from OG mice were plated as described above and infected with Fu-tet-hOct4 and FUdeltaGW-rtTA lentiviruses. The induction protocol was carried out as described above.

After infection, the culture medium was replaced with LIF-free ESC culture medium containing VC6T (VPA, CHIR99021, 616452, Tranylcypromine) plus DOX (1 µg/ml). Alternatively, MEFs harboring DOX-inducible Oct4 from Tet-On POUSF1 mouse strain B6; 129-Gt (ROSA) 26Sor$^{tm1(TrtTA*M2)Jae}$ Col1a1$^{tm2(tetO-Pou5f1)Jae}$/J were used in this screen (Li, et al., Cell Res., 21:196-204 (2011)). These two DOX-inducible systems were only used in this screen, but not in complete chemical reprogramming. Individual chemicals from small-molecule libraries were added to each well. The concentrations of small molecules are listed in Table 1D. Small molecules were added at different culture time points. 5-aza-C(5-Azacytidine) and DZNep were added from day 8. The medium and chemicals were changed every 4 days; DOX was added only for the first 4-8 days. Chemical treatments were continued for 16-24 days or until GFP-positive colonies appeared. Primary hits were selected for further confirmation and optimization. CiPSC colonies were counted on day 44. Primary hits were selected for further confirmation and optimization.

Figure 3:
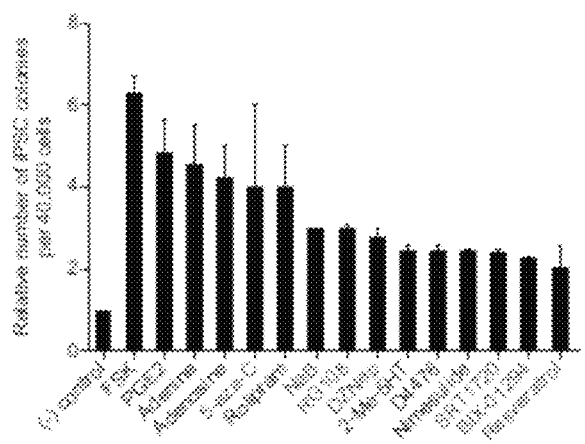
FIG. 3 is a bar graph showing relative number of iPSC colonies following treatment with indicated small molecules. (−) control, DMSO. Error bars indicate s.d (n≥2). Abbreviations: PEG2 (Prostaglandin E12); 5-aza-C(5-Azacytidine); NaB (Sodium Butyrate).

Small molecule hits, including several cAMP agonists (FSK, Prostaglandin E2, and Rolipram) and epigenetic modulators [3-deazaneplanocin A (DZNep), 5-Azacytidine, sodium butyrate, and RG108], were identified in this screen (FIG. 3 and Table 1D).

Example 3: Complete Chemical Reprograming without the Oct-4 Inducible System

Figure 4A:
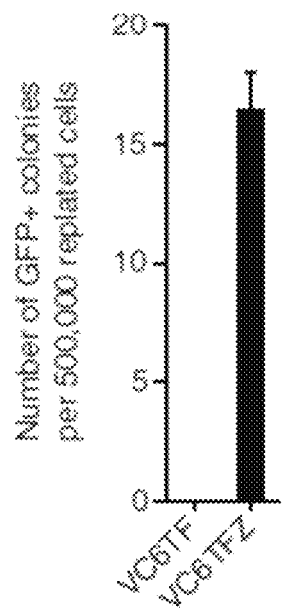
FIG. 4A shows numbers of GFP-positive colonies induced after DZNep treatment on day 36. Error bars, mean±SD (n=2 biological repeat wells).
Figure 4B:
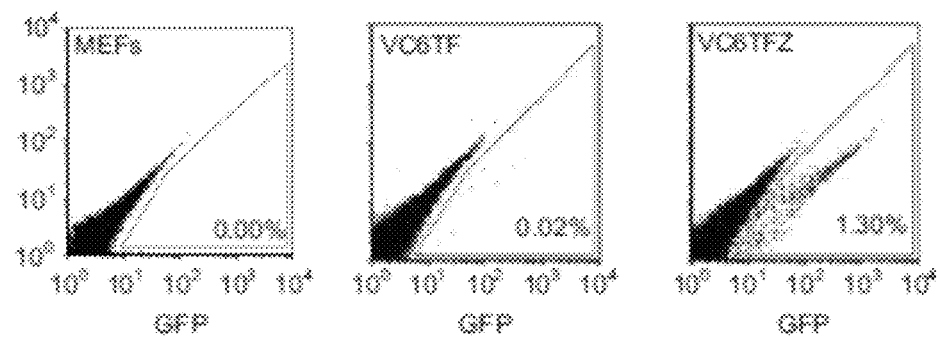
FIG. 4B is a FACS analysis of GFP-positive cells induced from OG-MEFs. Left, the absence of GFP-positive cells in initial MEFs; middle and right, proportion of GFP-positive cells induced by VC6TF (middle) and VC6TFZ (right) on day 44.
Figure 4C:
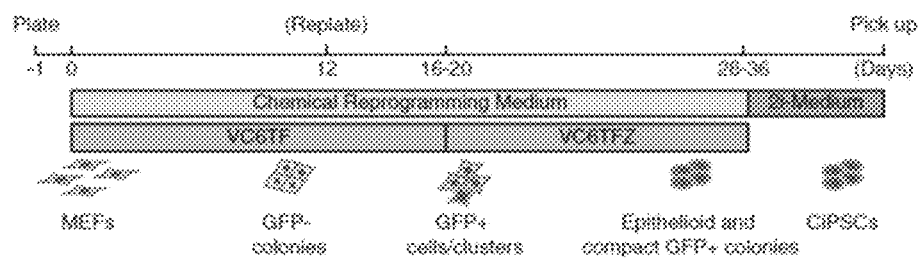
FIG. 4C is a Schematic diagram illustrating the process of CiPSC generation. Scale bars, 100 mm. For (FIG. 4A), cells for reprogramming were replated on day 12.
Figure 4D:
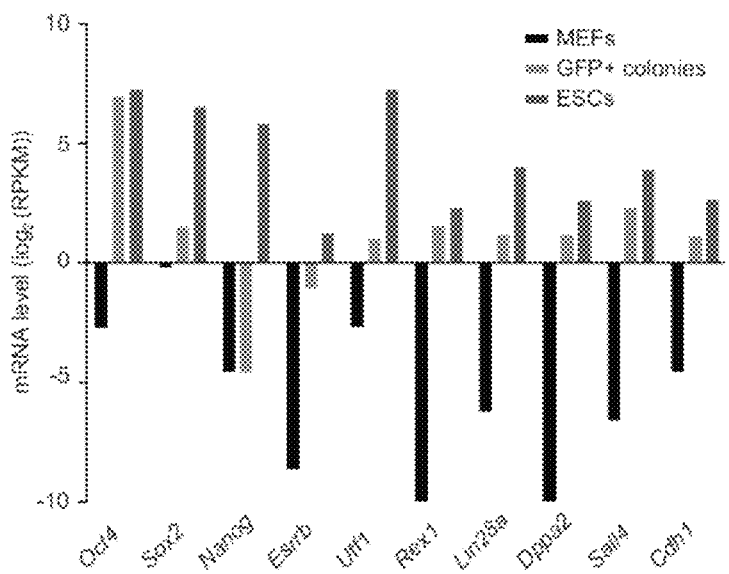
FIG. 4D shows mRNA levels of pluripotency-related genes detected by RNA-seq analysis in MEFs, GFP-positive colonies and ESCs (R1). Unlike mouse ESC colonies, these GFP-positive colonies, which were epithelioid and compact, could not maintain in ESC culture condition and were collected on day 36.
Figure 4E:
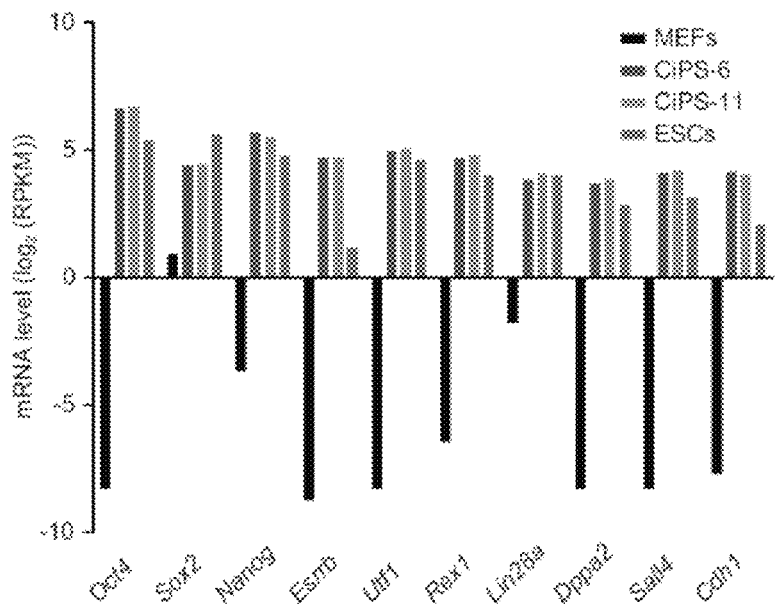
FIG. 4E shows mRNA levels of pluripotency-related genes detected by RNA-seq analysis in MEFs, CiPSCs and ESCs (R1).

To achieve complete chemical reprogramming without the Oct4-inducible system, small molecules were further tested in the chemical reprogramming of OG-MEFs without transgenes. When DZNep was added 16 days after treatment with VC6TF (VC6TFZ), GFP-positive cells were obtained more frequently by a factor of up to 65 than those treated with VC6TF, forming compact, epithelioid, GFP-positive colonies without clearcut edges (FIGS. 4A-B and 4E). In these cells, the expression levels of most pluripotency marker genes were elevated but were still lower than in ESCs, suggesting an incomplete reprogramming state (FIGS. 4G and H). After switching to 2i medium with dual inhibition (2i) of glycogen synthase kinase-3 and mitogen-activated protein kinase signaling after day 28 post treatment, certain GFP-positive colonies developed an ESC-like morphology (domed, phase-bright, homogeneous with clear-cut edges) (FIG. 4C) (Silva, et al., *PLoS Biol.*, 6: e253 (2008); Theunissen, et al., *Curr. Biol.*, 21:65-71 (2011)). These colonies could be further cultured for more than 30 passages, maintaining an ESC-like morphology (FIGS. 4A, 4D and 4G). These are referred to as 2i-competent, ESC-like, and GFP-positive cells as chemically induced pluripotent stem cells (CiPSCs). A schematic diagram for the formation of CiPSCs as described above is shown in FIG. 4F.

Figure 5A:
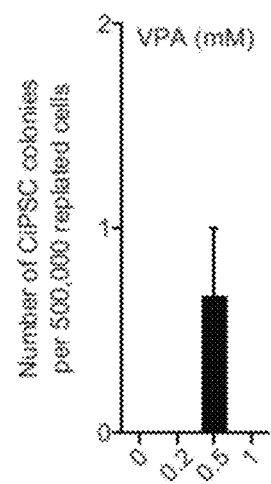
FIGS. 5A-K show optimization of the concentrations and treatment durations for individual chemicals in the VC6TFZ condition.
Figure 5B:
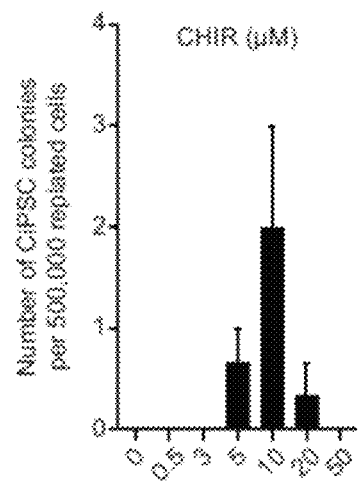
Figure 5C:
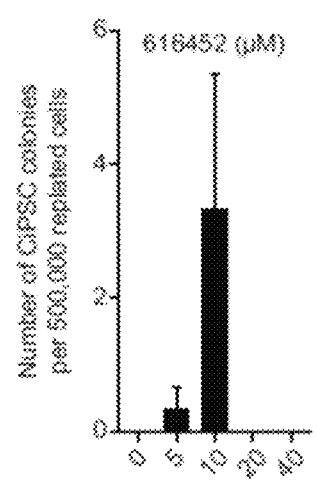
Figure 5D:
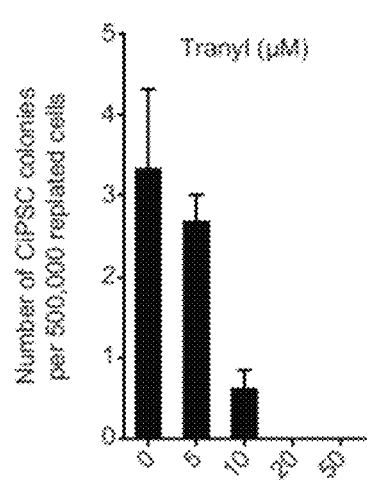
Figure 5E:
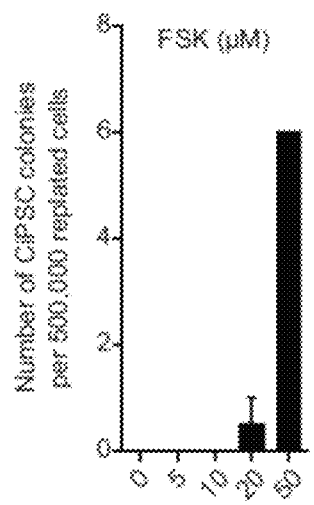
Figure 5F:
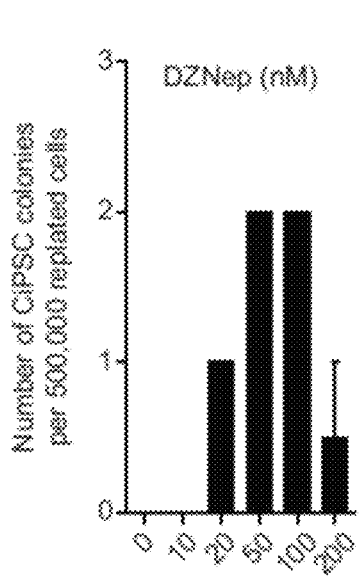
Figure 5G:
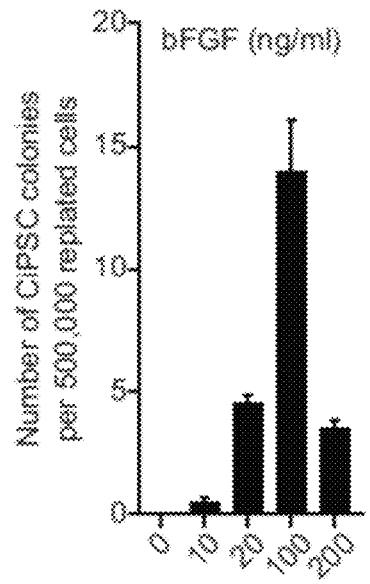
Figure 5H:
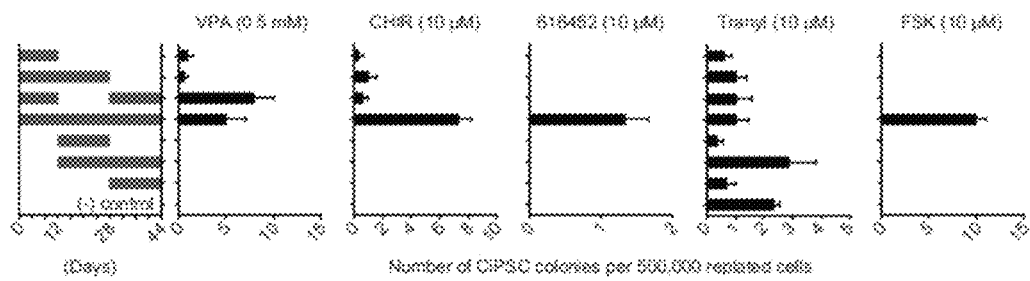
Figure 5I:
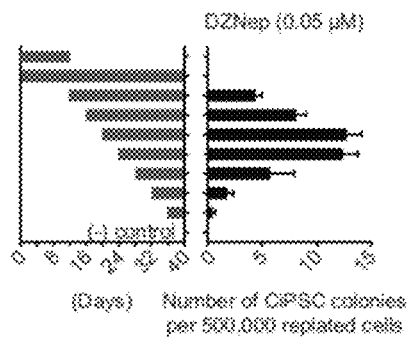
Figure 5J:
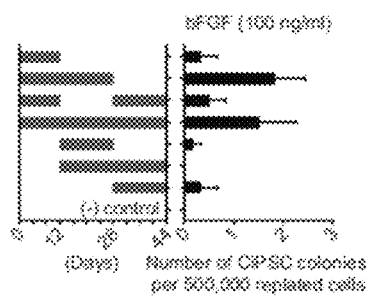
Figure 5K:
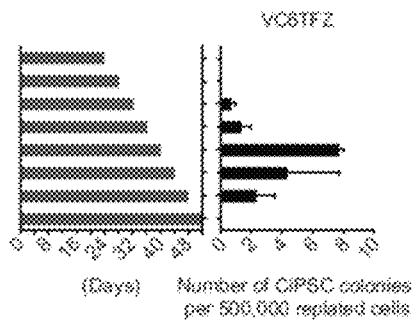

Next, the dosages and treatment duration of the small molecules were optimized leading to generation of 1 to 20 CiPSC colonies from 50,000 initially plated MEFs (FIGS. 5A-K). FIGS. 5A-F show the potential concentrations of VPA, CHIR99021, 616452, tranylcypromine and Forskolin in inducing CiPSCs. They also indicate the reprogramming efficiency may differ from experiments using different concentrations of the small molecules. The preferable concentrations for each small molecule were shown (VPA, 0.5 mM; CHIR99021, 10 µM; 616452, 10 µM; Forskolin, 50 µM and DZNep 50 nM). FIG. 5G shows the preferable concentration of bFGF (100 ng/mL), it also indicate that bFGF is necessary in inducing CiPSCs. FIG. 5H, I, J show the preferable durations of the small molecules and bFGF that were used in inducing CiPSCs. FIG. 5K indicates the preferable time points to change the medium containing VC6TF into 2i-medium. FIG. 5A-F show the potential concentrations of VPA, CHIR99021, 616452, tranylcypromine and Forskolin in inducing CiPSCs. They also indicate the reprogramming efficiency may differ from experiments using different concentrations of the small molecules. The preferable concentrations for each small molecule were shown (VPA, 0.5 mM; CHIR99021, 10 µM; 616452, 10 µM; Forskolin, 50 µM and DZNep 50 nM). FIG. 5G shows the preferable concentration of bFGF (100 ng/mL), it also indicate that bFGF is necessary in inducing CiPSCs. FIG. 5H, I, J show the preferable durations of the small molecules and bFGF that were used in inducing CiPSCs. FIG. 5K indicates the preferable time points to change the medium containing VC6TF into 2i-medium.

Figure 6A:
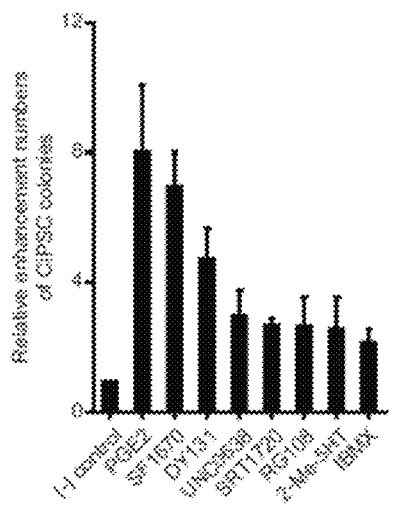
FIGS. 6A-F show validated small molecules improving chemical reprogramming efficiency or kinetics.
Figure 6B:
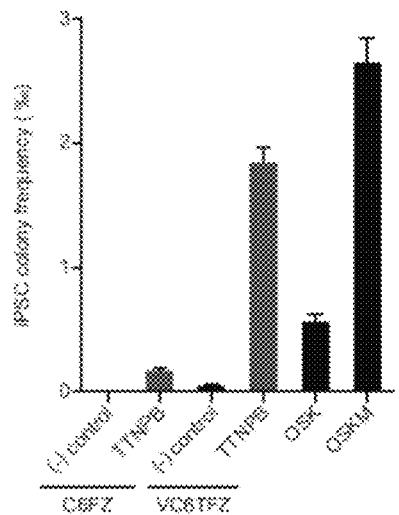
Figure 6C:
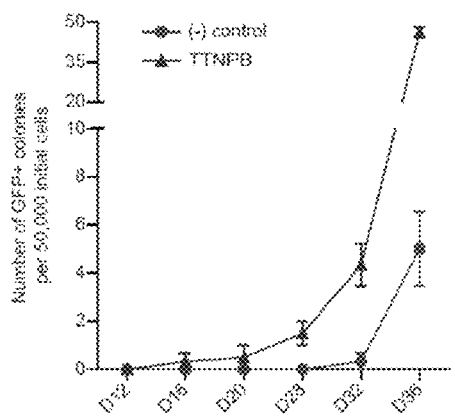
Figure 6D:
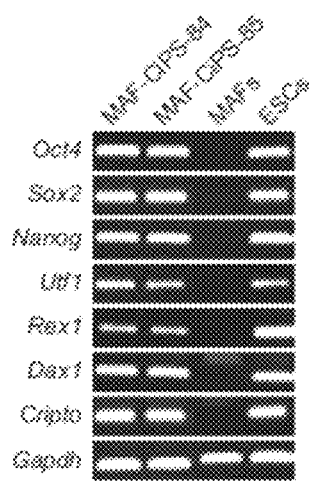
Figure 6E:
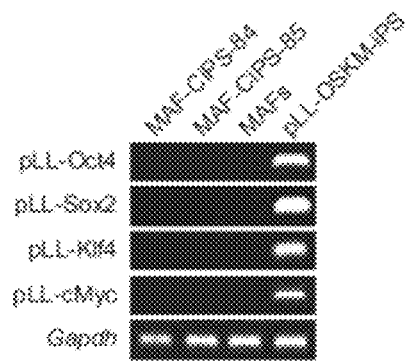
Figure 6F:
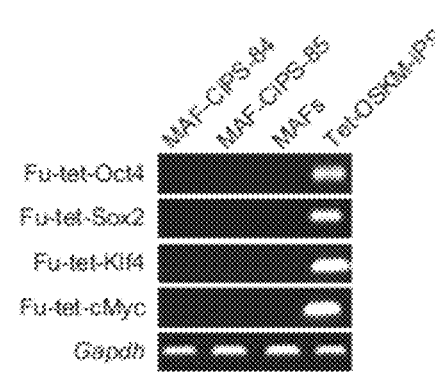
Figure 7A:
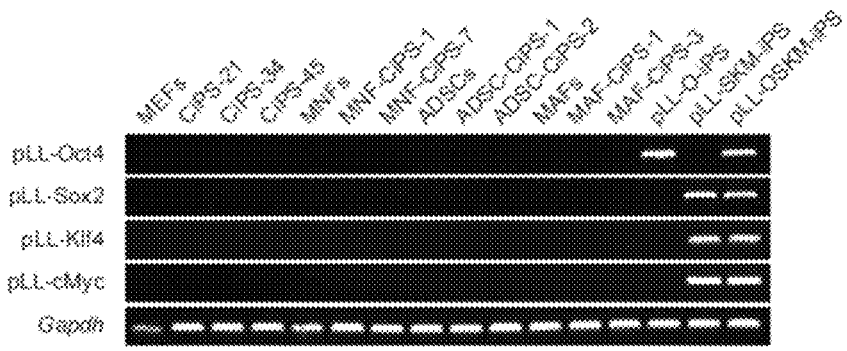
FIGS. 7A-D shows genomic PCR and southern blot analysis showing that CiPSCs were free of transgene contamination.
Figure 7B:
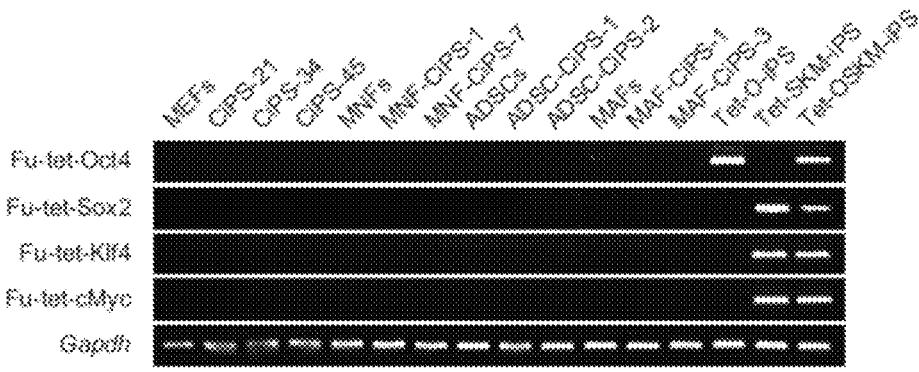
Figures 7C, 7D:
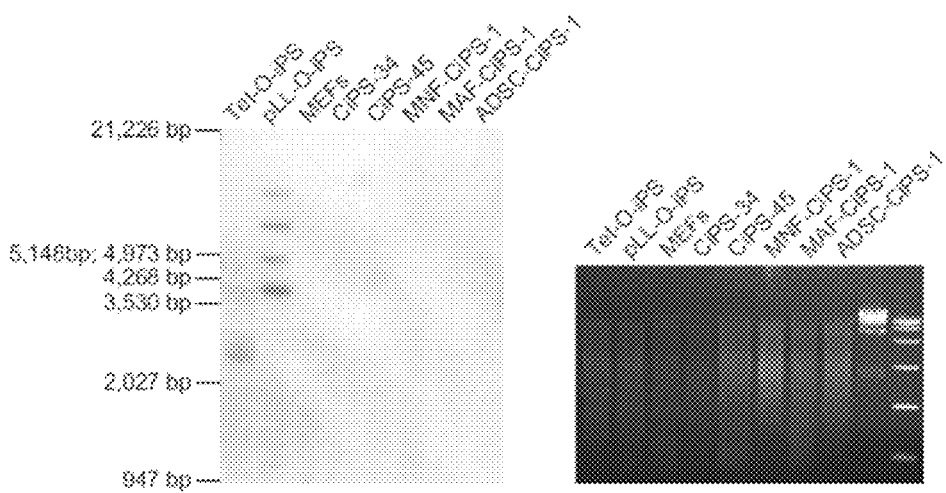

After an additional screen, some small-molecule boosters of chemical reprogramming were identified, among which, a synthetic retinoic acid receptor ligand, TTNPB, enhanced chemical reprogramming efficiency up to a factor of 40, to a frequency comparable to transcription factor-induced reprogramming (up to 0.2%) (FIGS. 6A-C; and Table 1D). An adult chimeric mouse produced with CiPSCs derived from MAFs (clone MAF-CiPS-84) (F) and black F2 offsprings produced with CiPSCs derived from MAFs (clone MAF-CiPS-85). Genomic PCR analysis showed that CiPSCs were free of transgene contamination (FIGS. 6D and E).

Using the small-molecule combination VC6TFZ, CiPSC lines were obtained from mouse neonatal fibroblasts (MNFs), mouse adult fibroblasts (MAFs), and adipose-derived stem cells (ADSCs) with OG cassettes by efficiency lower by a factor of ~10 than that obtained from MEFs. Table 5.

TABLE 5

Summary of CiPS cell characterization

| Clone number | Initial cell types | Mouse strain | Chemical combinations | ESC-like and GFP-positive | Non-transgenic | AP staining | RT-PCR | immuno-staining | Gene expression profiling | Teratoma | karyotype | DNA | chimeras | Germ-line transmission |
|---|---|---|---|---|---|---|---|---|---|---|---|---|---|---|
| CiPS-6 | MEFs | OG (C57) × ICR | VC6TFMB + Z | ✓ | ✓ | ✓ | ✓ | ✓ | ✓ | ✓ | — | — | ✓ | No |
| CiPS-11 | MEFs | OG (C57) × ICR | VC6TFMB + Z | ✓ | ✓ | ✓ | ✓ | ✓ | ✓ | ✓ | ✓ | ✓ | ✓ | ✓ |
| CiPS-21 | MEFs | OG (C57) × ICR | VC6TFDBS + Z | ✓ | ✓ | ✓ | ✓ | ✓ | ✓ | ✓ | ✓ | ✓ | ✓ | ✓ |
| CiPS-25 | MEFs | OG (C57) × ICR | VC6TFMDBSPR + Z | ✓ | ✓ | ✓ | ✓ | ✓ | ✓ | ✓ | ✓ | ✓ | ✓ | — |
| CiPS-30 | MEFs | OG (C57) × ICR | VC6TFMDBSPR + Z | ✓ | ✓ | ✓ | ✓ | ✓ | ✓ | ✓ | ✓ | ✓ | ✓ | ✓ |
| CiPS-34 | MEFs | OG (C57) × ICR | VC6TFMP + Z | ✓ | ✓ | ✓ | ✓ | ✓ | ✓ | — | ✓ | ✓ | ✓ | No |
| CiPS-36 | MEFs | OG (C57) × ICR | VC6TFMDB + Z | ✓ | ✓ | ✓ | ✓ | ✓ | — | ✓ | — | — | ✓ | — |
| CiPS-39 | MEFs | OG (C57) × ICR | VC6TFMDB + Z | ✓ | ✓ | ✓ | ✓ | ✓ | — | ✓ | — | — | ✓ | — |
| CiPS-42 | MEFs | OG (C57) × ICR | FC6 + Z | ✓ | ✓ | ✓ | ✓ | ✓ | ✓ | ✓ | ✓ | ✓ | ✓ | — |
| CiPS-43 | MEFs | OG (C57) × ICR | FC6 + Z | ✓ | ✓ | ✓ | ✓ | ✓ | ✓ | — | — | — | — | — |
| CiPS-44 | MEFs | OG (C57) × ICR | FC6 + Z (w/o bFGF) | ✓ | ✓ | ✓ | ✓ | ✓ | ✓ | ✓ | ✓ | ✓ | ✓ | ✓ |
| CiPS-45 | MEFs | OG (C57) × ICR | VC6TF + Z | ✓ | ✓ | — | ✓ | ✓ | — | — | — | — | — | — |
| CiPS-47 | MEFs | OG (C57) × ICR | VC6F + Z | ✓ | ✓ | — | ✓ | ✓ | ✓ | ✓ | — | ✓ | ✓ | — |
| CiPS-50 | MEFs | OG (C57) × ICR | VC6TFBPS + Z | ✓ | ✓ | ✓ | ✓ | ✓ | ✓ | ✓ | — | ✓ | ✓ | — |
| CiPS-56 | MEFs | OG (C57) × ICR | VC6TF + Z | ✓ | ✓ | ✓ | ✓ | ✓ | ✓ | — | — | ✓ | ✓ | — |
| CiPS-82 | MEFs | OG (C57) × OG (C57) | VC6TFPS + Z | ✓ | ✓ | ✓ | — | — | ✓ | — | — | ✓ | ✓ | — |
| CiPS-453 | MEFs | OG (C57) × 129 | VC6TFMPS + Z | ✓ | ✓ | ✓ | ✓ | ✓ | ✓ | ✓ | ✓ | ✓ | ✓ | ✓ |
| CiPS-WT1 | MEFs (without OG-reporter) | ICR | VC6TFMPS + Z | — | ✓ | ✓ | ✓ | — | — | ✓ | — | ✓ | ✓ | — |
| CiPS-WT2 | MEFs (without OG-reporter) | C57 × 129 | VC6TFMPS + Z | — | ✓ | ✓ | ✓ | — | ✓ | ✓ | ✓ | ✓ | ✓ | No |
| MNF-CiPS-1 | Mouse neonatal fibroblasts (MNFs) | OG (C57) × ICR | VCT6FMDBR + Z | ✓ | ✓ | — | ✓ | ✓ | ✓ | ✓ | — | ✓ | ✓ | — |
| MNF-CiPS-2 | MNFs | OG (C57) × ICR | VC6TFRP + Z | ✓ | ✓ | — | ✓ | ✓ | — | ✓ | — | ✓ | ✓ | — |
| MNF-CiPS-7 | MNFs | OG (C57) × ICR | VC6TFS + Z | ✓ | ✓ | ✓ | ✓ | ✓ | ✓ | ✓ | — | ✓ | ✓ ✓ | No |
| ADSC-CiPS-1 | Adipocyte stem cells | OG (C57) × ICR | VC6TFMPS + Z | ✓ | ✓ | ✓ | ✓ | ✓ | ✓ | ✓ | — | ✓ | — | — |
| ADSC-CiPS-2 | Adipocyte stem cells | OG (C57) × ICR | VC6TFMPS + Z | ✓ | ✓ | — | ✓ | — | ✓ | — | — | ✓ | ✓ | — |
| ADSC-CiPS-3 | Adipocyte stem cells | OG (C57) × ICR | VC6TFDM + Z | ✓ | ✓ | — | ✓ | ✓ | ✓ | — | — | ✓ | ✓ | — |
| ADSC-CiPS-4 | Adipocyte stem cells | OG (C57) × ICR | VC6TFDM + Z | ✓ | ✓ | ✓ ✓ ✓ ✓ ✓ | ✓ ✓ ✓ ✓ | ✓ ✓ ✓ ✓ ✓ | — | ✓ ✓ ✓ ✓ | — | ✓ ✓ ✓ ✓ | ✓ ✓ ✓ | — |
| MAF-CiPS-1 | MAFs | OG (C57) × ICR | VC6TF + Z | ✓ | ✓ | — | — | — | — | — | — | — | — | — |
| MAF-CiPS-3 | MAFs | OG (C57) × ICR | VC6TFDM + Z | ✓ | ✓ | ✓ ✓ ✓ ✓ ✓ | ✓ ✓ ✓ ✓ ✓ | ✓ ✓ ✓ ✓ ✓ | ✓ ✓ ✓ ✓ ✓ | ✓ ✓ ✓ | ✓ ✓ ✓ | ✓ ✓ ✓ ✓ | ✓ ✓ ✓ ✓ ✓ ✓ ✓ ✓ | No |
| MAF-CiPS-62 | MAFs | OG (C57) × ICR | VC6TFBS + Z | ✓ | ✓ | | | | | | | | | ✓ |
| MAF-CiPS-63 | MAFs | OG (C57) × ICR | VC6TFPS + Z | ✓ | ✓ | | | | | | | | | ✓ |
| MAF-CiPS-73 | MAFs | OG (C57) × ICR | VC6TFBS + Z | ✓ | ✓ | | | | | | | | | ✓ |
| MAF-CiPS-76 | MAFs | OG (C57) × ICR | VC6TFB + Z | ✓ | ✓ | | | | | | | | | |
| MAF-CiPS-80 | MAFs | OG (C57) × ICR | FC6 + Z | ✓ | ✓ | | | | | | | | | |
| MAF-CiPS-81 | MAFs | OG (C57) × ICR | FC6 + Z | ✓ | ✓ | | | | | | | | | |
| MAF-CiPS-83 | MAFs | OG (C57) × ICR | VC6TFP + Z | ✓ | ✓ | | | | | | | | | |
| MAF-CiPS-84 | MAFs | OG (C57) × ICR | VC6TFN + Z | ✓ | ✓ | ✓ ✓ ✓ | ✓ ✓ ✓ | ✓ ✓ ✓ | ✓ ✓ ✓ | ✓ ✓ | ✓ ✓ ✓ | ✓ ✓ ✓ | ✓ ✓ ✓ ✓ ✓ ✓ ✓ | ✓ |
| MAF-CiPS-85 | MAFs | OG (C57) × ICR | VC6TFN + Z | ✓ | ✓ | | | | | | | | | |
| CiPS-101 | MEFs | OG (C57) × ICR | FC6 | ✓ | — | ✓ | — | — | — | — | — | ✓ | — | — |

TABLE 5-continued

| Clone number | Initial cell types | Mouse strain | Chemical combinations | ESC-like and GFP-positive | Non-transgenic | AP staining | RT-PCR | immuno-staining | Gene expression profiling | Teratoma | karyotype | DNA | chimeras | Germ-line transmission |
|---|---|---|---|---|---|---|---|---|---|---|---|---|---|---|
| CiPS-102 | MEFs | OG (C57) × ICR | FCT6 + Z | ✓ | — | — | — | — | — | — | — | — | — | — |
| CiPS-103 | MEFs | OG (C57) × ICR | FC6N + Z | ✓ | — | — | — | — | — | — | — | — | — | — |
| CiPS-104 | MEFs | OG (C57) × ICR | FC6T + 4PB + Z | ✓ | — | — | — | — | — | — | — | — | — | — |
| CiPS-105 | MEFs | OG (C57) × ICR | VCT6 + Z | ✓ | — | — | — | — | — | — | — | — | — | — |
| CiPS-31 | MEFs | OG (C57) × ICR | VC6TF | ✓ | ✓ | ✓ | ✓ | ✓ | — | — | — | — | — | — |
| CiPS-106 | MEFs | OG (C57) × ICR | VC6T + DBcAMP + Z | ✓ | — | — | — | — | — | — | — | — | — | — |
| CiPS-107 | MEFs | OG (C57) × ICR | VC6T + IBMX + Z | ✓ | — | — | — | — | — | — | — | — | — | — |
| CiPS-108 | MEFs | OG (C57) × ICR | VC6T + Rloipram + Z | ✓ | — | — | — | — | — | — | — | — | — | — |
| CiPS-109 | MEFs | OG (C57) × ICR | VF6T + TD114-2 + Z | ✓ | — | — | — | — | — | — | — | — | — | — |
| CiPS-110 | MEFs | OG (C57) × ICR | VC6TF + NepA | ✓ | — | — | — | — | — | — | — | — | — | — |
| CiPS-111 | MEFs | OG (C57) × ICR | VC6TF + Adox | ✓ | — | — | — | — | — | — | — | — | — | — |
| CiPS-112 | MEFs | OG (C57) × ICR | VC6TF + DZA | ✓ | — | — | — | — | — | — | — | — | — | — |
| CiPS-113 | MEFs | OG (C57) × ICR | VC6TF + Decitabine + EPZ004777 | ✓ | — | — | — | — | — | — | — | — | — | — |
| CiPS-114 | MEFs | OG (C57) × ICR | VC6TFN + Z | ✓ | — | — | — | — | — | — | — | — | — | — |
| CiPS-115 | MEFs | OG (C57) × ICR | VC6TF + AM580 + Z | ✓ | — | — | — | — | — | — | — | — | — | — |
| CiPS-116 | MEFs | OG (C57) × ICR | VC6TF + Ch55 + Z | ✓ | — | — | — | — | — | — | — | — | — | — |
| CiPS-117 | MEFs | OG (C57) × ICR | VC6TF + TTNPB + PGE2 + 5-aza-C | ✓ | — | — | — | — | — | — | — | — | — | — |
| CiPS-118 | MEFS | OG (C57) × ICR | VC6TF + TTNPB + PGE2 + Decitabine | ✓ | ✓ | — | — | — | — | — | — | — | — | — |
| CiPS-119 | MEFs | OG (C57) × ICR | VC6TFDMB+UNC0638+Scriptaid | ✓ | — | — | ✓ | ✓ | — | ✓ | — | — | — | — |
| CiPS-120 | MEFs | OG (C57) × ICR | VC6TF + Decitabine + EPZ | ✓ | — | — | — | — | — | — | — | — | — | — |

Moreover, CiPSCs were induced from wild-type MEFs without OG cassettes or any other genetic modifications by a comparable efficiency to that achieved from MEFs with OG cassettes. The CiPSCs were also confirmed to be viral-vector free by genomic polymerase chain reaction (PCR) and Southern blot analysis (FIGS. 7A-D).

Furthermore, small molecule combinations were used to generate CiPSCs from neural stem cells and from cells obtained from the intestinal epithelium (Table 6).

TABLE 6

Generation of CiPSCs from neural stem cells and cells from the intestinal epithelium

| Clone number | Initial cell type | mouse strain | small molecules | ES-like morphology | genomic PCR | AP staining | RT-PCR | immuno-fluorescence | microarray | teratoma | karyotype | DNA methylation | chimeric mice | germ-line reansmission |
|---|---|---|---|---|---|---|---|---|---|---|---|---|---|---|
| IE-CiPS-1 | intestinal epithelium cell | OG (C57) × ICR | VC6TFAM580 + Z | √ | √ | ND | √ | √ | √ | √ | √ | √ | √ | √ |
| NS-CiPS-1 | neural stem cell | OG (C57) × ICR | VC6TFZ + Ch55 + Decitabine + EPZ | √ | √ | ND | √ | √ | ND | √ | ND | ND | √ | ND |

("ND" represents "not determined yet")

AM580 is 4-[(5,6,7,8-Tetrahydro-5,5,8,8-tetramethyl-2-naphthalenyl) carboxamido]benzoic acid]; Ch55 is 4-[(1E)-3-[3,5-bis (1,1-Dimethylethyl)phenyl]-3-oxo-1-propenyl] benzoic acid] and EPZ. Intestinal and neural stem cells, likes MEF can be reprogrammed using VC6TFZ, without addition of the indicated small molecules, albeit with a different efficiency.

Figure 8A:
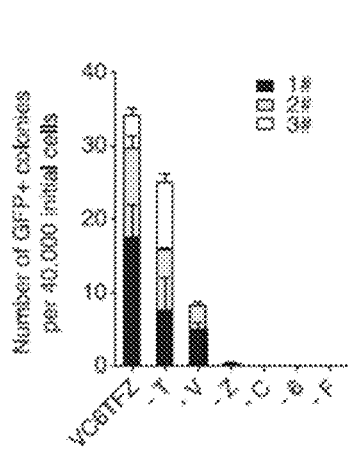
FIGS. 8A-B show the numbers of GFP-positive (FIG. 8A) and CiPSC (FIG. 8B) colonies induced by removing individual chemicals from VC6TFZ. The results of three independent experiments are shown with different colors (white, gray, and black).
Figure 8B:
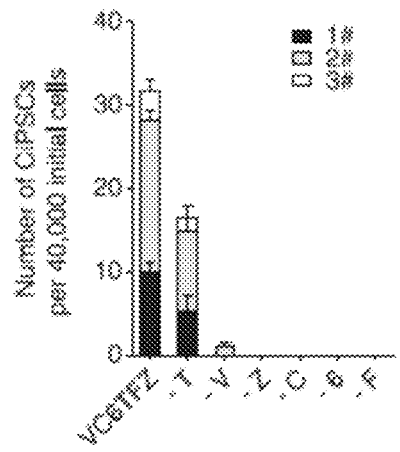
Figure 9A:
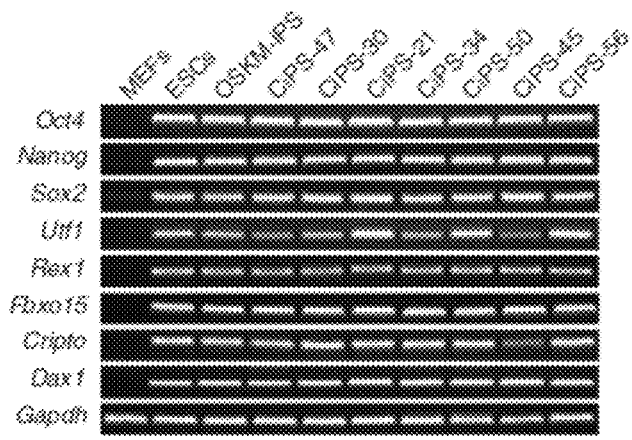
FIG. 9A shows pluripotency marker expression in different clones of CiPS cells compared to MEFS, as illustrated by RT-PCR.
Figure 9B:
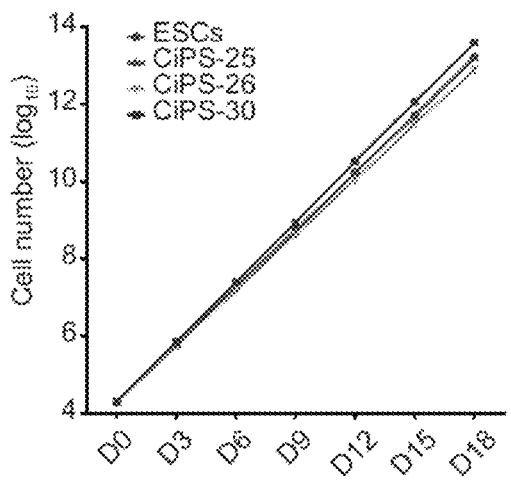
FIG. 9B shows growth curves for CiPSCs.
Figure 9C:
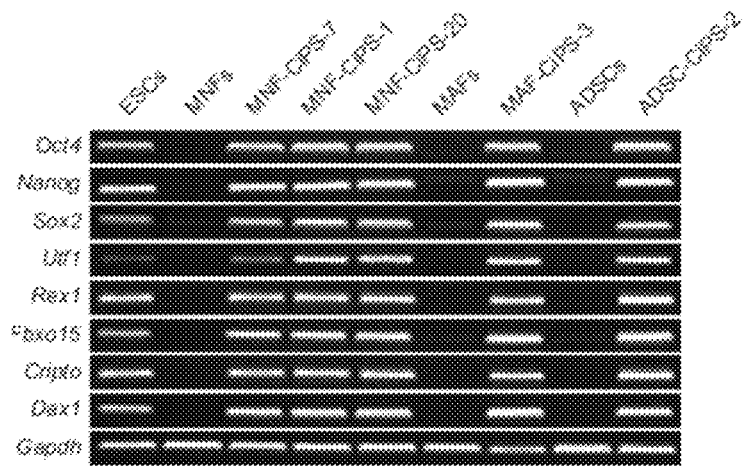
Figure 9D:
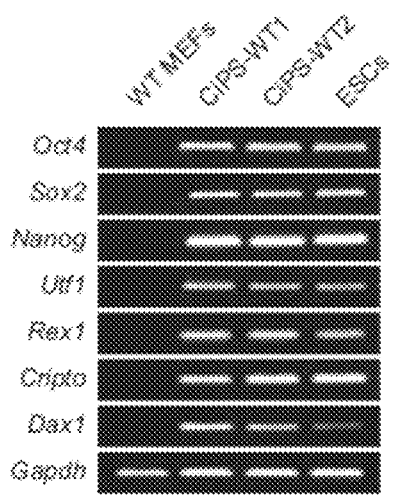

Experiments were next carried out to determine which of these small molecules were critical in inducing CiPSCs. Four essential small molecules (shown below) whose individual withdrawal from the combinations generated significantly reduced GFP-positive colonies and no CiPSCs were identified (FIGS. 8A-B).

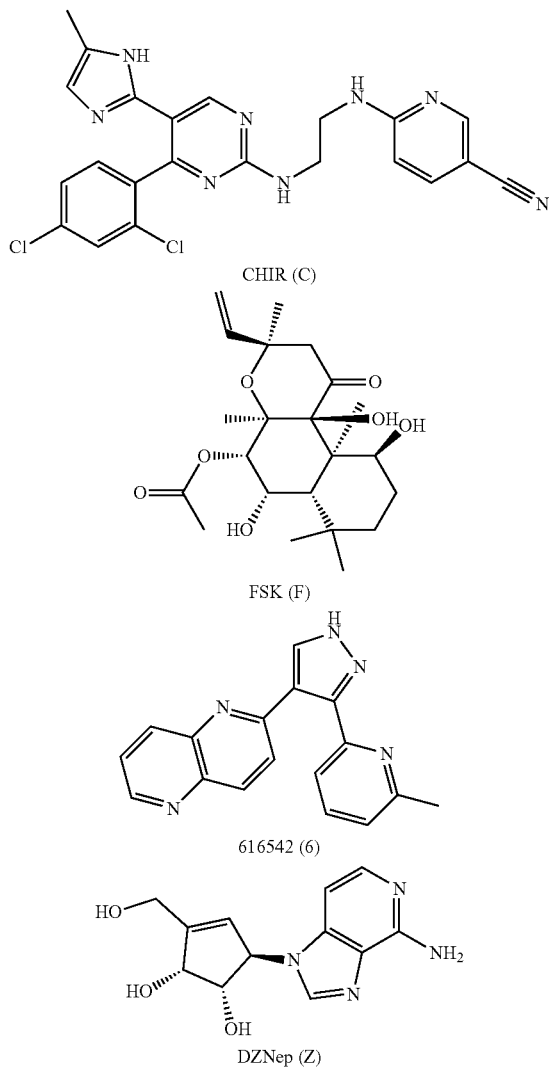

These small molecules (C6FZ) are: CHIR (C), a glycogen synthase kinase 3 inhibitor (Ying, et al., Nature, 453:519-523 (2008)); 616452 (Zhang, et al., Cell Res. 21:196-204 (2011)), a transforming growth factor-beta receptor inhibitor (Maherali, et al., Curr. Biol., 19:1718-1723 (2009)); FSK (F), a cAMP agonist (FIG. 14F) (Insel, et al., Cell. Mol. Neurobiol., 23:305-314 (2003)); and DZNep (Z), an S-adenosylhomocysteine (SAH) hydrolase inhibitor (FIG. 14A) (Chiang, et al., Pharmacol., Ther. 77:115-134 (1998); Gordon, et al., Eur. J. Biochem., 270:3507-3517 (2003)).

C6FZ was able to induce CiPSCs from both MEFs and MAFs, albeit by an efficiency lower by a factor of 10 than that induced by VC6TFZ (Table 5).

Figure 14A:
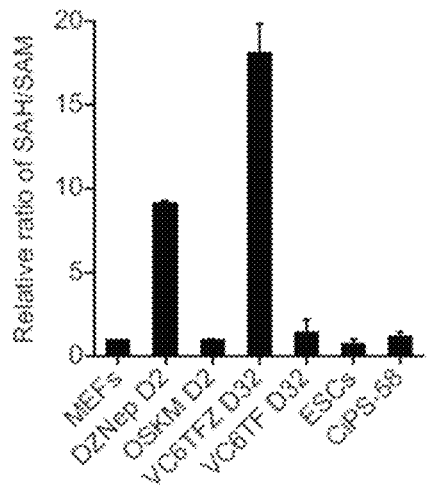
FIGS. 14A-B show biological activity of DZNep during chemical reprogramming.
Figure 14B:
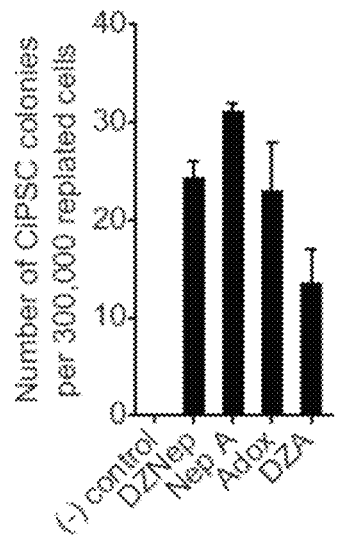
Figure 14C:
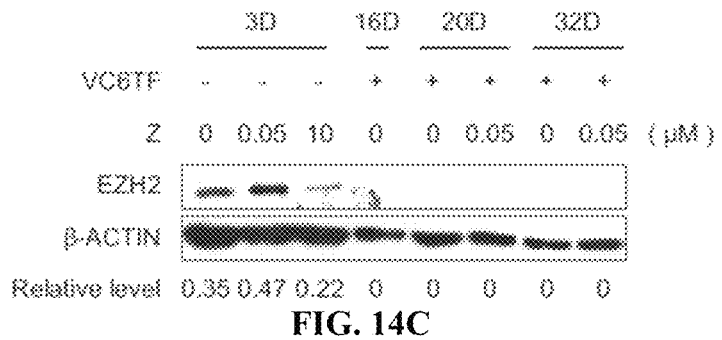
FIG. 14C shows protein levels of EZH2 were analyzed by western blot analysis.
Figure 14D:
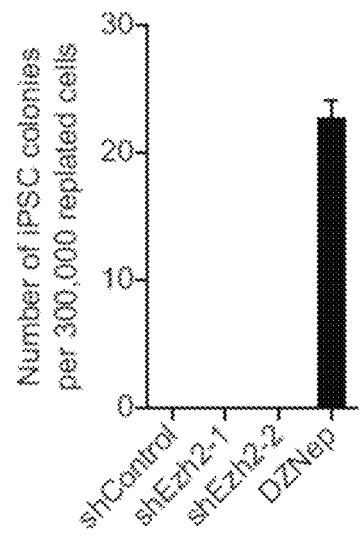
FIG. 14D shows numbers of iPSC colonies induced by VC6TF plus shRNA or DZNep. Error bars indicate the s.d. (n=3).
Figure 14E:
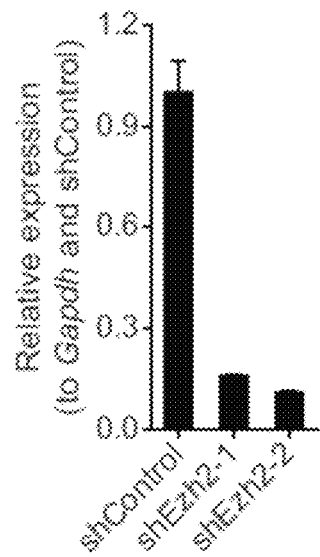
FIG. 14E shows real-time PCR showing that Ezh2 was repressed following shRNA-mediated knockdown of Ezh2. Error bars indicate the s.d. (n=2).
Figure 14F:
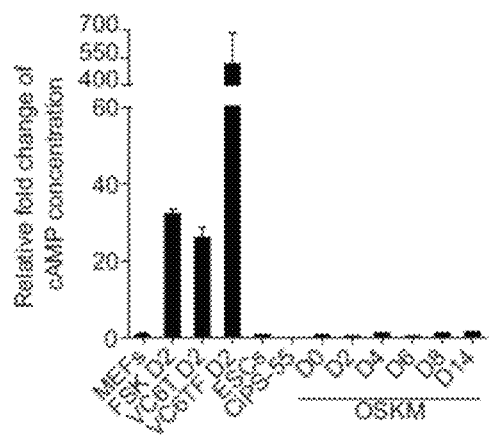
FIG. 14F shows the relative intracellular cAMP levels compared to those in MEFs.
Figure 14G:
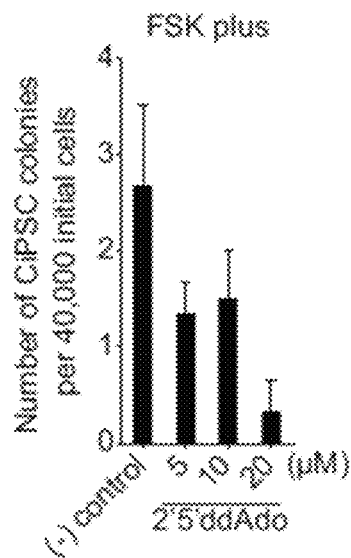
FIG. 14G shows the effect of inhibition of adenylate cyclase by 2'5'ddAdo on the number of CiPSC colonies generated by VC6TFZ. (−) control, DMSO.
Figure 14H:
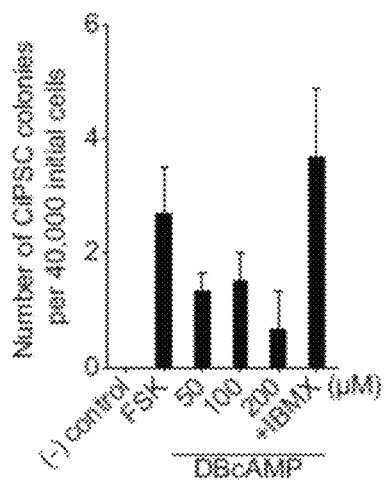
FIG. 14H-J show the effect of replacing FSK with a cAMP analog (DBcAMP with/without IBMX) accompanied by VC6T plus DZNep (VC6TZ) treatment, or the phosphodiesterase inhibitors (Rolipram and IBMX) in combination with VC6TZ during CiPSC induction, on chemical reprogramming.
Figure 14I:
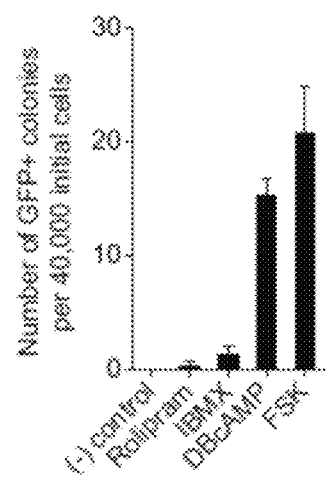
Figure 14J:
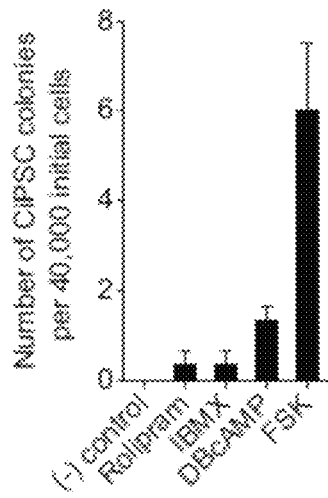
Figure 14K:
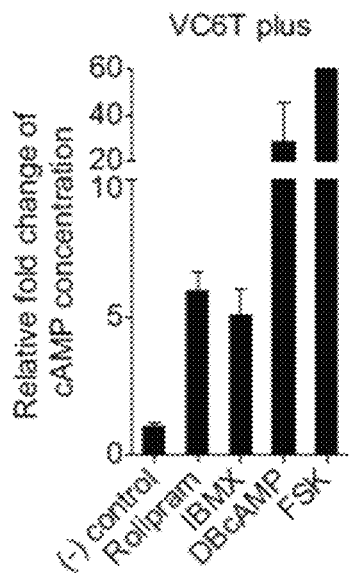
FIG. 14K is a quantification of intracellular cAMP levels following treatment of MEF, with the indicated chemicals. Error bars indicate the s.d. (n≥2).

The effect of inhibiting adenylate cyclase on the number of colonies generated by VC6TFZ was tested. Inhibition of adenylate cyclase by 2'5'ddAdo decreased the number of colonies formed by VC6TFZ (FIG. 14F). The effect of replacing FSK with the cAMP analog (DBcAMP), alone or in combination with phosphodiesterase inhibitors, IBMX, or the phosphodiesterase inhibitor, rolipram and IBMX, on cell reprograming was also tested. Both DBcAMP and IBMX were used at 50 µM in the combination treatment. The data is shown in FIGS. 14G-J. The intracellular levels of cAMP concentrations in MEF following treatment with rolipram (10 µM), IBMX (50 µM, DBcAMP (50 M) and FSK (10 µM) was compared to control (−) DMSO (FIG. 14K). Forskolin significantly elevates the CAMP level, which is similar to other cAMP agonists (Rolipram and IBMX) or analog (DBcAMP). GFP+Pluripotent stem cells were induced with other cAMP agonists or analog, which were used to substitute Forskolin. A CAMP inhibitor, 2'5'ddAdo suppressed the efficiency of CiPSC induction. These taken together suggest that Forskolin facilitate chemical reprogramming by modulating cAMP signaling pathway.

Generation of CiPSCs from NSCs Obtained from Oct4-GFP Transgenic Mice

Figure 14L:
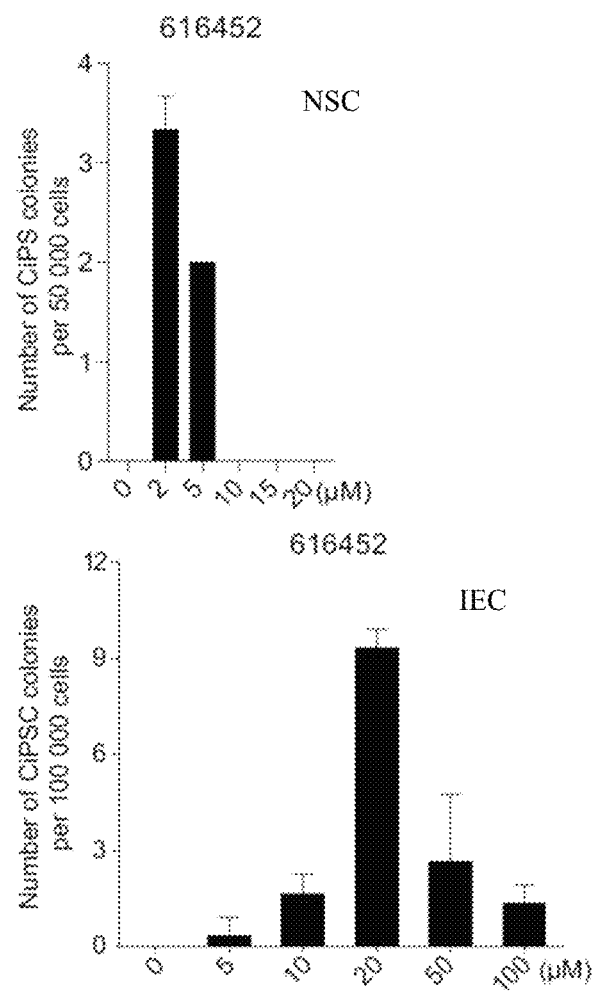
FIG. 14L shows the effect of 616452 concentration during the first 20 days of chemical reprogramming (Error bars, mean±SD, n=3) in NSC and IEC cells.
Figure 14M:
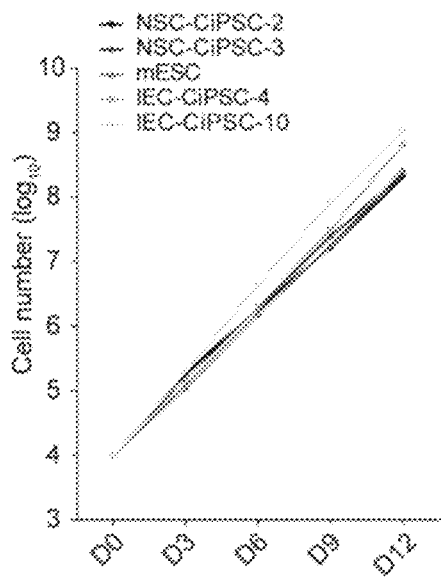
FIG. 14M shows growth curves for CiPSCs. NSC-CiPSC-2 from passage 6; NSC-CiPSC-5 from passage 7; IEC-CiPSC-4 from passage 10; and IEC-CiPSC-10 from passage 7.
Figure 14N:
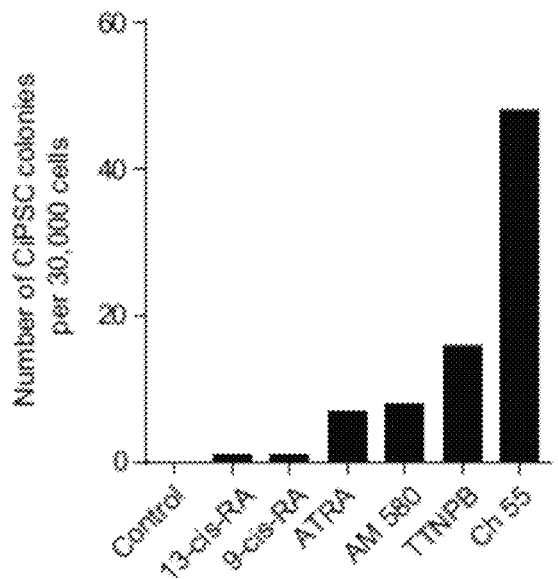
FIG. 14N shows CiPSC colonies obtained from different RAR agonists used for on chemical reprogramming of OG MEFs. 13-cis-RA, 2 μM; 9-cis-RA, 2 μM; ATRA, All-trans Retinoic acid, 2 μM; AM 580, 0.01 μM; TTNPB, 2 μM; Ch 55, 1 μM.

In other experiments NSCs (obtained from Oct4-GFP transgenic mice) were treated with the reprogramming cocktail "VC6TF" (VPA, V; CHIR99021, CHIR, C; 616452, 6; Tranylcypromine, T; Forskolin, F). This did not able to induce pluripotency from NSCs. Then, potential reprograming boosters including a RA agonist, Ch 55 (5) and a Dot11 inhibitor, EPZ 004777 (EPZ, E) were added i.e., VC6TFZE5. The number of CiPSC colonies obtained from 30,000 with different RAR agonists is shown in FIG. 14N. Epithelial clusters emerged on day 8 after adjusting the concentration of 616452 from the traditional 10 µM to 2 µM (data not shown), and proliferated with time. After the addition of DZNep (Z) from day 20, compact and epithelioid colonies were observed on day 32 (data not shown). Subsequently, the Oct4-GFP reporter was gradually turned on after switching these colonies into 2i-medium with dual inhibition (2i) of MAPK signaling and GSK3 from day 40, and ESC-like OG-positive colonies with clear-cut edges were observed. The final cells are referred to as NSC-CiPSCs. The same small molecule combination was used to obtain CiPSCs from NSCs of postnatal mice (data not shown). Primary NSC-CiPSC colonies were harvested and passaged in 2i-medium plus mouse leukemia inhibitory factor (LIF) for more than 20 passages with stable ESC-like morphology and Oct4-GFP expression. There studies indicated that selection of the concentration of 616452 between the early and late stages of reprogramming affects the number of CiPSC obtained with chemical reprogramming from NSCs (14 L). At the late stage, the concentration of 616452 should be readjusted to 5 µM from day 20 (data not shown).

Generation of CiPSCs from Small Intestinal Epithelial Cells Obtained from Oct4-GFP Transgenic Mice IECs isolated from the small intestinal tissue of Oct4-GFP transgenic mice at embryonic day 13.5 were used in these studies. The isolated IECs exhibited epithelial cell morphology, and immunofluorescence staining showed that the IECs highly expressed a specific intestinal epithelial cell marker, KERATIN 20 (KRT20) (data not shown).

Isolated IECs were cultured with the reported chemical reprogramming cocktail VC6TF and the RAR agonist AM 580. DZnep was then added to the cocktail from day 16-20. During this process, epithelioid clusters were observed from day 4-8, and formed colonies from day 16 (data not shown). After switching to 2i-medium from day 32-36, compact, epithelioid, ESC-like OG-positive colonies with clear-cut edges were developed (data not shown). Primary CiPSC colonies were calculated and harvested on day 44-46, and passaged in 2i-medium plus mouse LIF for more than 20 passages, maintaining ESC-like morphology (data not shown). These cells were referred to as IEC-CiPSCs.

A lineage tracing experiment was performed using transgenic mice expressing the Cre recombinase driven by Villin, an epithelium specific gene promoter, crossed with mice expressing a loxP-stop-loxP-td-Tomato located in Rosa26 locus. The IECs were labelled by tdTomato fluorescence (data not shown). After exposure to the chemical cocktail, tdTomato fluorescent CiPSC colonies were generated from IECs (FIG. 14M and data not shown). By contrast to the data shown NSC, increasing the concentration of 616452 up to 20 μM during the first 12 days best support IEC reprograming, whereas a decreased concentration of 616452 is beneficial for NSC reprogramming (FIG. 14L bottom panel).

Example 4: Characterization of CiPSC Lines

Characterization of CiPSC Obtained from Fibroblasts

The established CiPSC lines were then further characterized. They grew with a doubling time (14.1 to 15.1 hours) similar to that of ESCs (14.7 hours), maintained alkaline phosphatase activity, and expressed pluripotency markers, as detected by immunofluorescence and reverse transcription (RT)-PCR (FIG. 9A-9D). Specifically, CiPS-25 from passage 21, CiPS-26 from passage 7 and CiPS-30 from passage 22 were cultured for another 6 passages. ESCs (R1) from passage 29 were used as controls. Cells were passaged every three days and seeded at a density of 20,000 cells per well in a 12-well plate without feeder layers in 2i-medium. Error bars indicate the s.d. (n=3). The calculated population doubling times of these cells were 14.8±2.1 (CiPS-25), 15.1±1.9 (CiPS-26), and 14.1±1.7 (CiPS-30) hours. These times were equivalent to that of ESCs (14.7±1.2 hours).

The gene expression profiles were similar in CiPSCs, ESCs, and OSKM-iPSCs (iPSCs induced by Oct4, Sox2, Klf4, and c-Myc). DNA methylation state and histone modifications at Oct4 and Nanog promoters in CiPSCs were similar to that in ESCs. In addition, CiPSCs maintained a normal karyotype and genetic integrity for up to 13 passages, i.e., CiPS cells maintain normal chromosome numbers, few copy number variations and genetic mutations, making them safe for further clinical application.

Figure 10A:
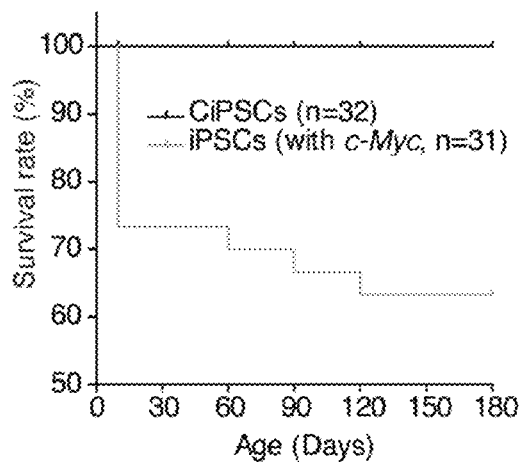
FIG. 10A shows survival curves of chimeras generated from CiPSCs. n, total numbers of chimeras studied.

To characterize their differentiation potential, CiPSCs were injected into immunodeficient (SCID) mice. The cells were able to differentiate into tissues of all three germ layers-respiration epithelium (endoderm); muscle cells (mesoderm); neural epithelium (endoderm) and pigmented epithelium (ectoderm). When injected into eight-cell embryos or blastocysts, CiPSCs were capable of integration into organs of all three germ layers, including gonads and transmission to subsequent generations. An adult chimeric mouse was produced from clone ciPS-34 as well as F2 offspring. Germline contribution of clone CiPS-45 was shown in testes. An adult chimeric mouse was also produced with CiPSCs derived from MNFs (clone MNF-CiPS-1). An adult chimeric mouse was produced with CiPSCs derived from MAFs (clone MAF-CiPS-62). Black F2 offspring were produced with CiPSCs derived from MAFs (clone MAF-CiPS-62). Black F2 offsprings were produced with CiPSCs derived from MAFs (clone MAF-CiPS-63). Chimeras were produced with CiPSCs derived from WT MEFs (clone CiPS-WT1, ICR) that were microinjected into (C57×DBA)× ICR embryos. Unlike chimeric mice generated from iPSCs induced by transcription factors including c-Myc (Nakagawa, et al., Proc. Natl. Acad. Sci. U.S.A. 107:14152-14157 (2010)), the chimeric mice generated from CiPSCs were 100% viable and apparently healthy for up to 6 months (FIG. 10A). These observations show that the CiPSCs were fully reprogrammed into pluripotency (Table 5).

Characterization of NSC- and IEC-Derived CiPSCs

Figure 10B:
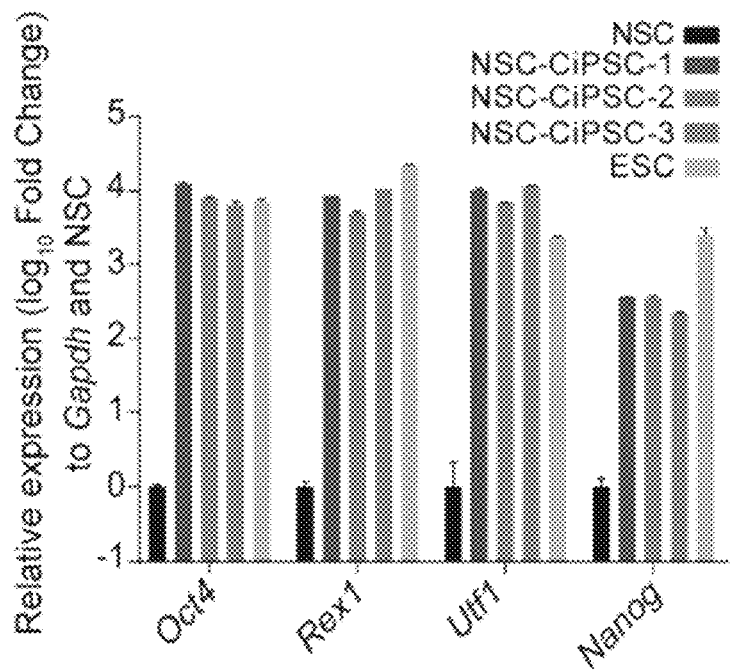
FIGS. 10B and 10C show pluripotency genes expression in NSC-CiPSCs (A) and IEC-CiPSCs (B) as measured by quantitative real-time PCR (Error bars, mean±SD, n=3).
Figure 10C:
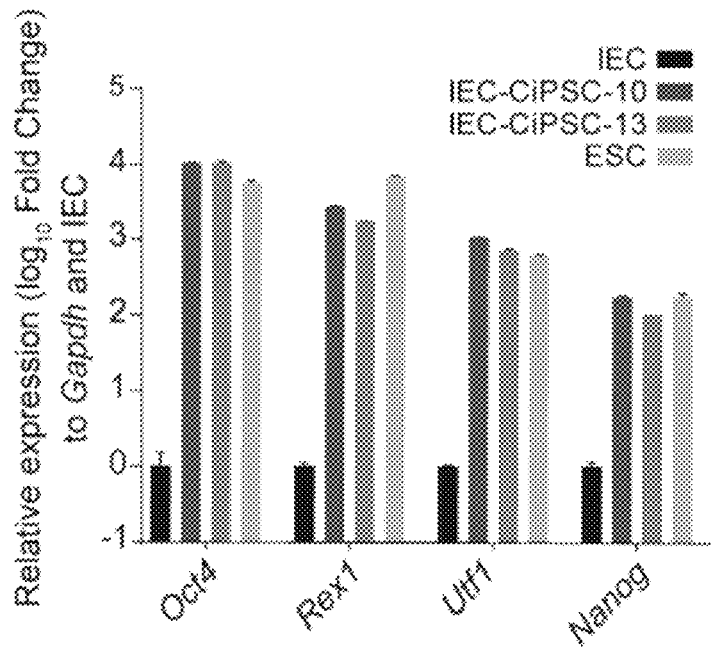

The established NSC-CiPSC lines and IEC-CiPSC lines were further characterized. The doubling time of the established CiPSC lines was 18 h-24 h, similar to mouse ESCs (FIG. 14M). Pluripotency gene expressions in derived CiPSC lines were comparable to mESCs as detected by quantitative real-time PCR and immunofluorescence staining, p (FIG. 10B-C). Global gene expression analysis was performed by RNA-sequencing, and NSC-CiPSCs and IEC-CiPSCs clustered with ESCs, in contrast to initial cells (data not shown). To detect the epigenetic reprogramming status, DNA methylation analysis was performed at two core pluripotency genes, the Oct4 and Nanog promoters, by bisulfite sequencing. The result showed that Oct4 and Nanog promoters were hypomethylated in CiPSCs and mESCs (data not shown). In addition, normal karyotypes were maintained for up to 7 passages (data not shown), and Table 7.

TABLE 7

Number of chromosomes in NSC-CiPSCs and IEC-CiPSCs by karyotype analysis

| | Chromosome number | | |
|---|---|---|---|
| Sample | 2n = 40 | 2n < 40 | 2n > 40 |
| NSC-CiPSC ♀ | 100% | 0% | 0% |
| IEC-CiPSC ♂ | 98% | 2% | 0% |
| pVillin-Cre-Id Tomato IEC-CiPSC ♂ | 100% | 0% | 0% |

To evaluate the pluripotency of CiPSCs derived from NSCs and IECs, their in vivo developmental potential was examined. Both CiPSC lines could form well-differentiated teratomas with tissues from all three germ layers after injection into immunodeficient (NOD/SCID) mice (data not shown). When injected into blastocysts, CiPSCs were able to generate chimeric mice with germline transmission competency (data not shown). These results demonstrated that CiPSC lines derived from NSCs and IECs were pluripotent and fully reprogrammed.

Example 5: Pluripotency Inducing Properties of Small Molecules

Figure 11A:
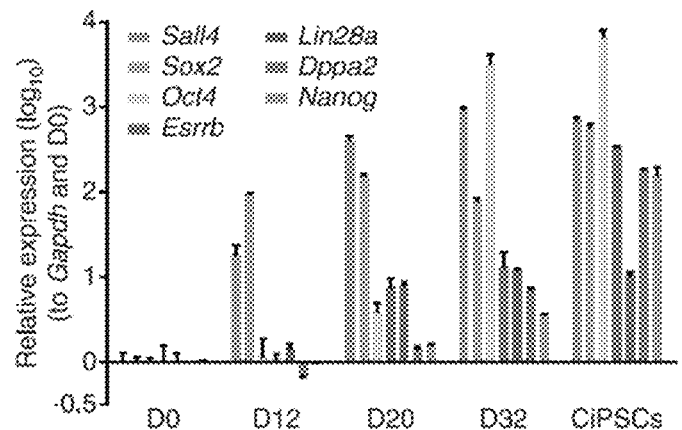
FIGS. 11A-B show the expression of pluripotency-related genes (FIG. 11A) and Gata6, Gata4, and Sox17 (FIG. 11B) as measured by real-time PCR.
Figure 11B:
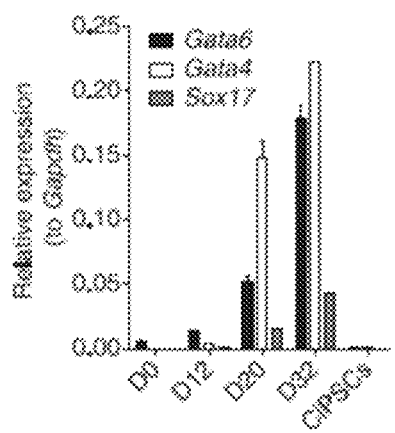
Figure 11C:
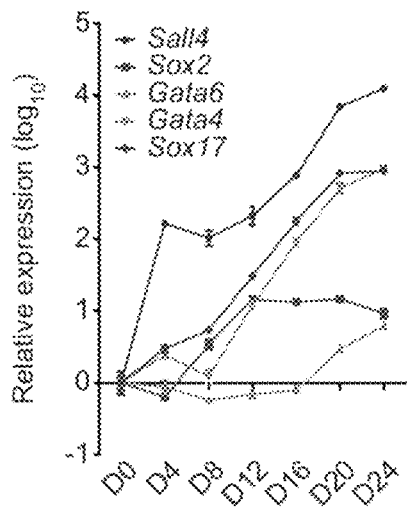
FIGS. 11C-D show expression of Sall4, Sox2, Gata6, Gata4 and Sox17 validated by real-time PCR. The fold changes in Sall4, Sox2, Gata6, Gata4 and Sox17 expression on days 4, 8, 12, 16, 20 and 24 (FIG. 11C) or at 12 h (FIG. 11D) compared with the expression in MEFs on day 0. Error bars indicate the s.d. (n=2).
Figure 11D:
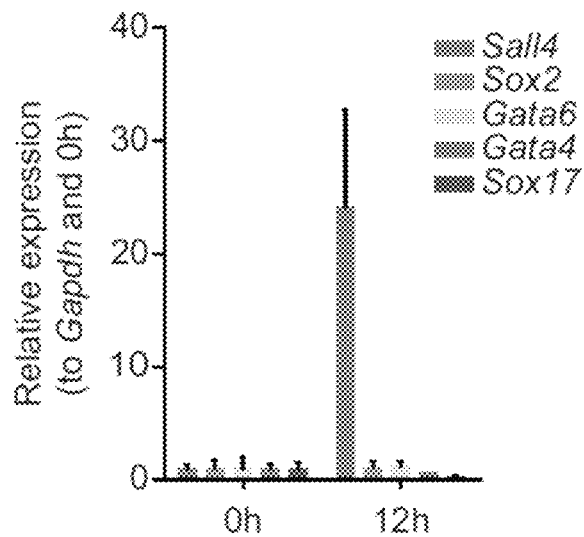
Figure 11E:
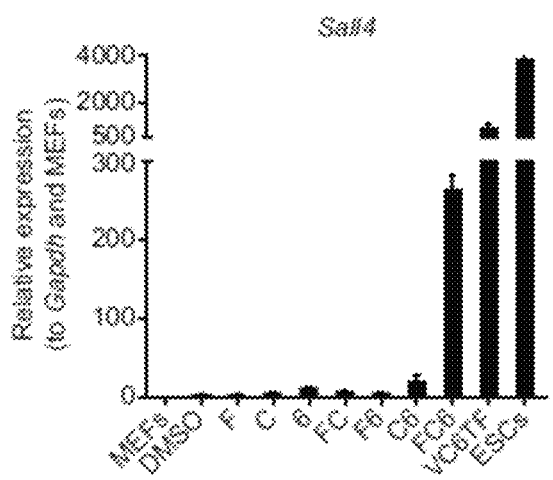
FIGS. 11E-I show the effects of individual and combined chemicals or withdrawing chemicals from VC6TF (or VC6TFZ) on the expression of genes.
Figure 11F:
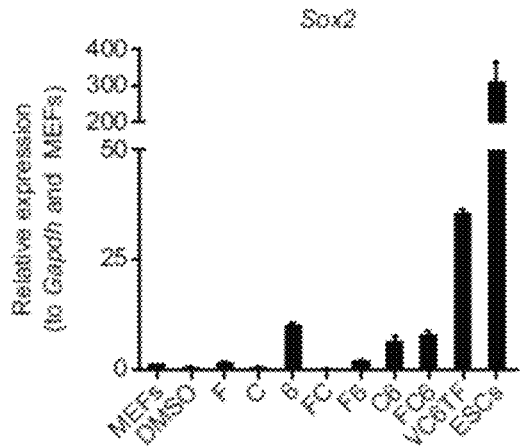
Figure 11G:
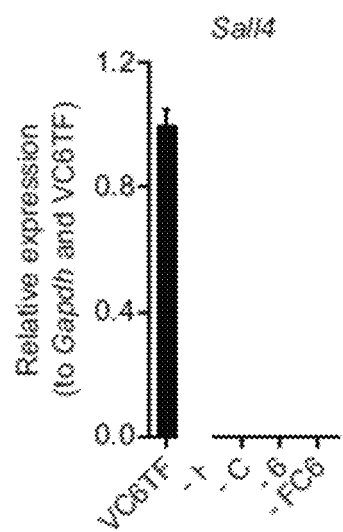
Figure 11H:
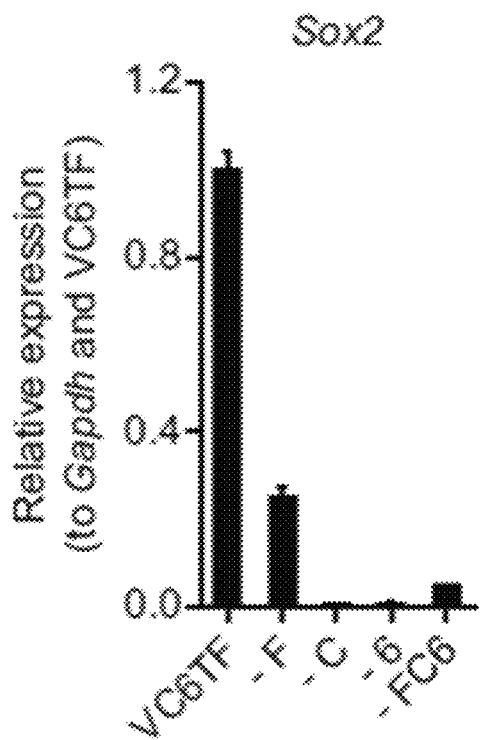
Figure 11I:
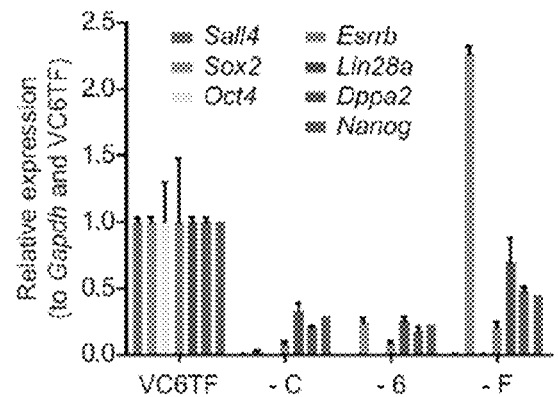
Figure 11J:
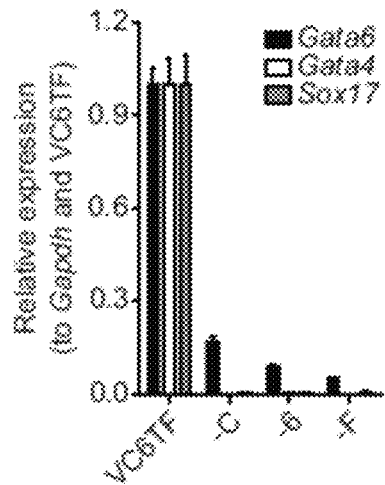
FIG. 11J shows the effects of withdrawing individual chemicals (CHIR, 616452 and FSK) from VC6TFZ on the expression of Gata6, Gata4 and Sox17 on day 32. Error bars indicate the s.d. (n=2).

To better understand the pluripotency-inducing properties of these small molecules, the global gene expression during chemical reprogramming was profiled. To determine clustering of gene expression profiles during chemical reprogramming, cell culture samples treated with VC6TFZ (Z was added from day 20) during chemical reprogramming on day 12, 20 and 32 were analyzed. MEFs on day 0, CiPSCs and ESCs were used as controls. Sequential activation of certain key pluripotency genes was observed, which was validated by real-time PCR and immunofluorescence. Genes that express in ESCs by more than 10 fold and in samples (day 32) by more than 3 fold compared to MEFs (day 0)

include Sall4, Sox2, Lin28a, Dppa2, Esrrb, Klf4 and Pou5f1. Genes that express in samples (day 32) by more than 3 folds compared to MEFs (day 0) and ESCs include Sox 17, Gata6 and Gata4. The expression levels of two pluripotency-related genes, Sall4 and Sox2, were most significantly induced in the early phase in response to VC6TF, as was the expression of several extra-embryonic endoderm (XEN) markers Gata4, Gata6, and Sox17 (FIG. 11A-J). The expression of Sall4 was enhanced most significantly as early as 12 hours after small molecule treatment, suggesting that Sall4 may be involved in the first step toward pluripotency in chemical reprogramming (FIG. 11D). With respect to experiments in which small molecules were withdrawn from the treatment used, the data shows that each of Forskolin, CHIR99021 and 616452 is essential in activating the endogenous expression of Sall4 and Sox2 after 12 days (FIGS. 11G and 11H), and the subsequent expression of other pluripotency genes (FIG. 11I). These molecules were also required in activating XEN-genes, such as Gata6, Gata4 and Sox17.

Figure 12A:
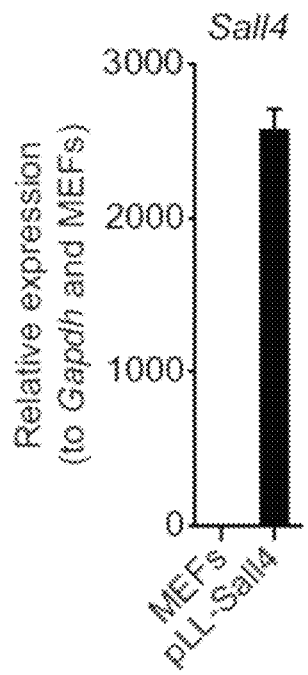
FIGS. 12A-B shows relative expression levels of Sall4 (FIG. 12A) and Sox2 (FIG. 12B) in MEFs on day 4 post-transduction validated by real-time PCR. Error bars indicate the s.d (n=2).
Figure 12B:
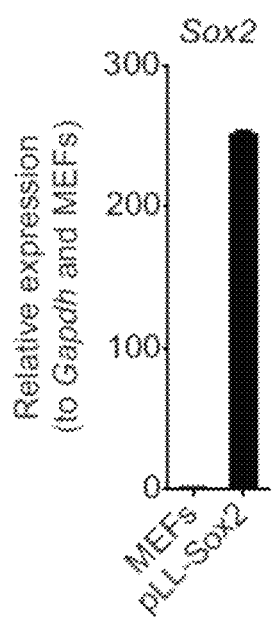
Figure 12C:
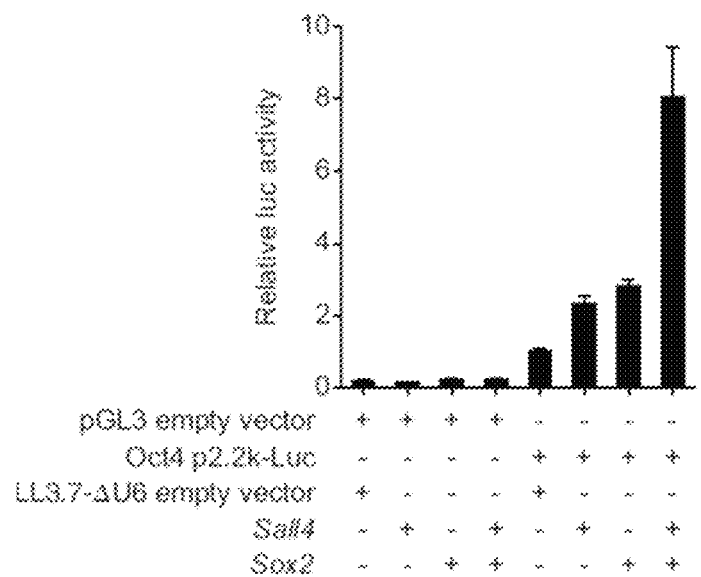
FIG. 12C shows Oct4 promoter-driven luciferase activity was examined in MEFs transfected with Sall4 or/and Sox2 plasmids. Error bars indicate the s.d. (n=3).
Figure 12D:
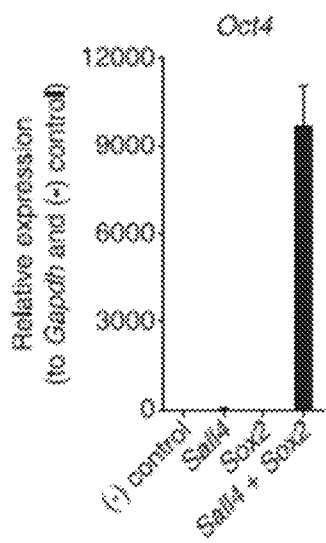
FIGS. 12D-E show Oct4 activation (FIG. 12D) and numbers of GFP-positive and iPSC colonies (FIG. 12E) induced by the overexpression of Sall4 and Sox2, with C6F removed from VC6TFZ.
Figure 12E:
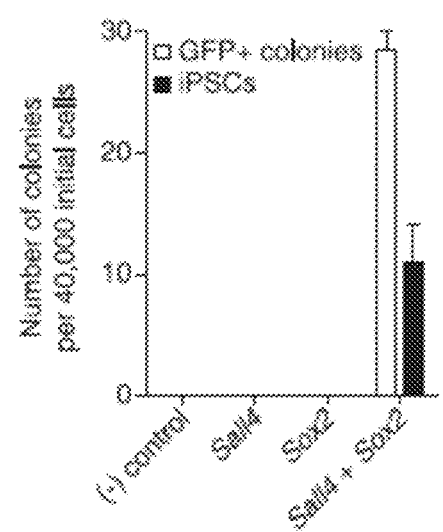
Figure 13A:
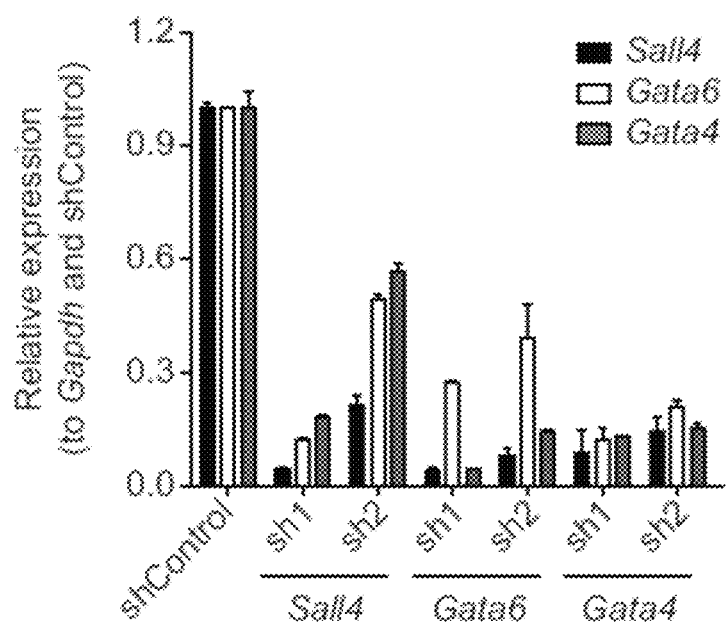
FIGS. 13A-D show gene expression changes by the knockdown of Sall4, Gata6, Gata4 or Sox17 on day 24.
Figure 13B:
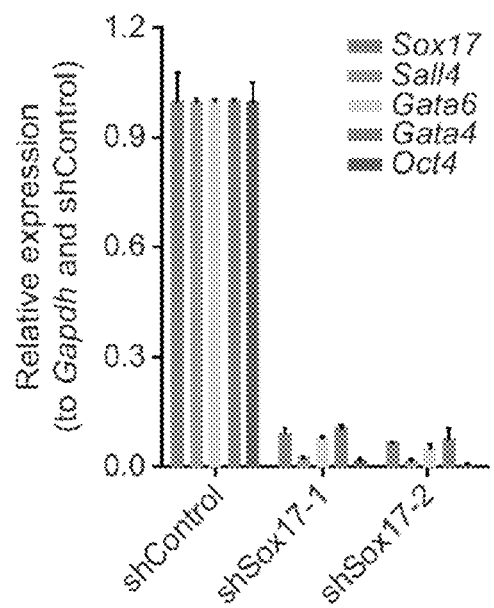
Figure 13C:
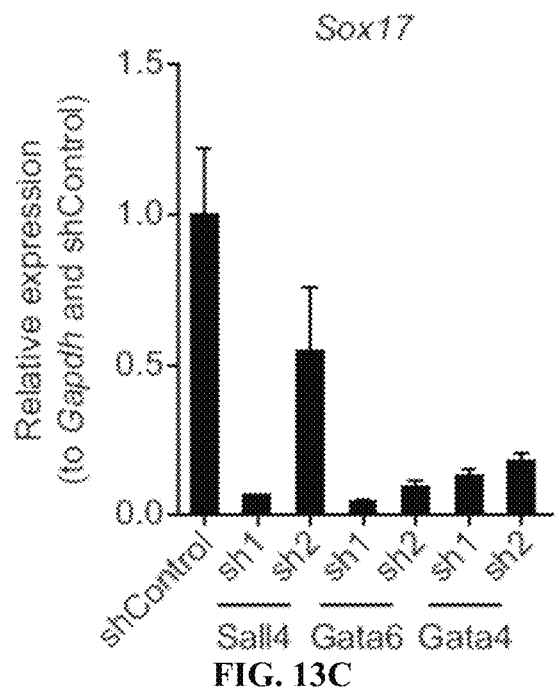
Figure 13D:
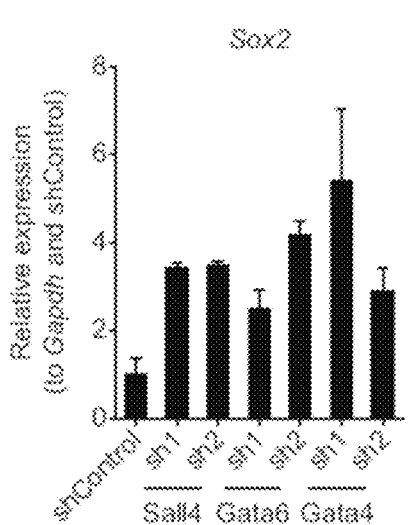
Figure 13E:
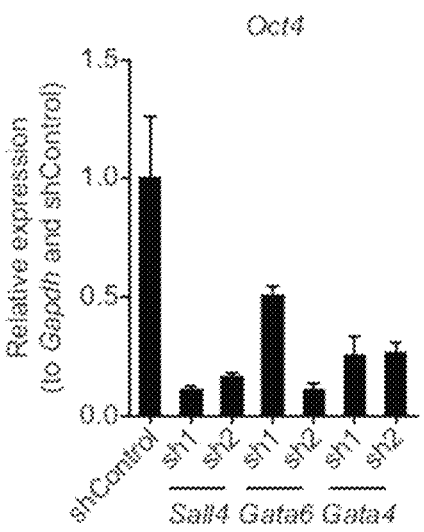
FIGS. 13E-F show the effects of Sall4, Gata6 or Gata4 knockdown on the expression of Oct4 and iPSCs formation.
Figure 13F:
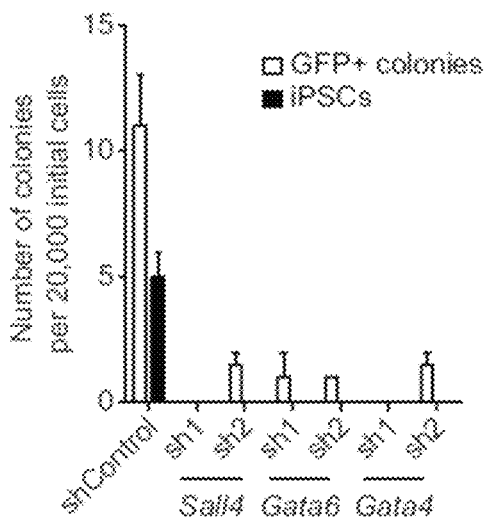
Figure 13G:
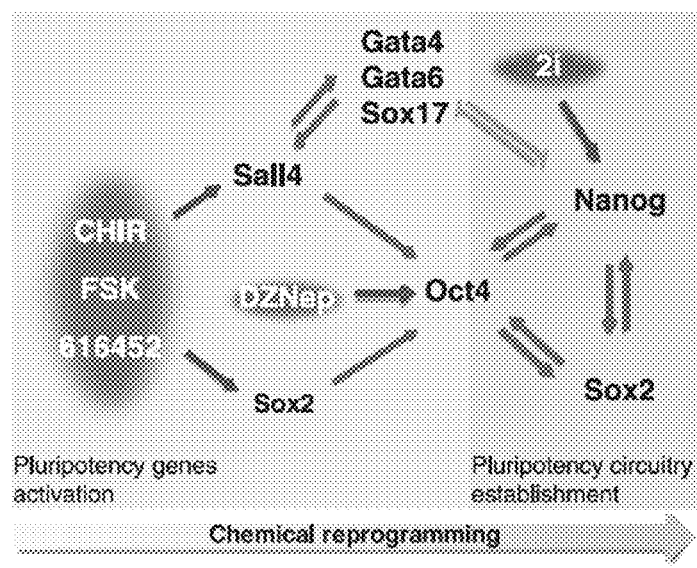
FIG. 13G is a schematic diagram illustrating the stepwise establishment of the pluripotency circuitry during chemical reprogramming.

The roles of the endogenous expression of these genes in chemical reprogramming were examined, using gene overexpression and knockdown strategies. The data shows that the concomitant overexpression of Sall4 and Sox2 was able to activate an Oct4 promoter-driven luciferase reporter (FIGS. 12A-C) and was sufficient to replace C6F in inducing Oct4 expression and generating iPSCs (FIGS. 12D-E). The endogenous expression of Sall4, but not Sox2, requires the activation of the XEN genes, and vice versa (FIGS. 13A-D). This suggests a positive feedback network formed by Sall4, Gata4, Gata6, and Sox17, similar to that previously described in mouse XEN formation (Lim, et al., *Cell Stem Cell*, 3:543-554 (2008)). Knockdown of Sall4 or these XEN genes impaired Oct4 activation and the subsequent establishment of pluripotency (FIGS. 13E-F), inconsistent with previous finding that Gata4 and Gata6 can contribute to inducing pluripotency (Shu, et al., *Cell*, 153:963-975 (2013)). Taken together, these findings revealed a Sall4-mediated molecular pathway that acts in the early phase of chemical reprogramming (FIG. 13G). This step resembles a Sall4-mediated dedifferentiation process in vivo during amphibian limb regeneration (Neff, et al., *Dev. Dyn.*, 240: 979-989 (2011)).

Figure 11K:
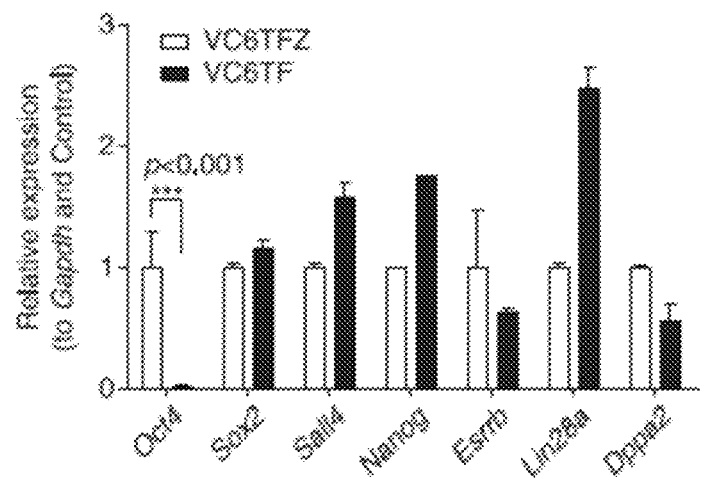
FIG. 11K shows the expression of pluripotency-related genes in the presence and absence of DZNep on day 32.

Next, the role of DZNep, which was added in the late phase of chemical reprogramming was investigated. The data shows that Oct4 expression was enhanced significantly after the addition of DZNep in chemical reprogramming (FIG. 11A), and DZNep was critical for stimulating the expression of Oct4 but not the other pluripotency genes (FIG. 11K). As an SAH hydrolase inhibitor, DZNep elevates the concentration ratio of SAH to S-adenosylmethionine (SAM) and may thereby repress the SAM-dependent cellular methylation process (FIG. 14A). Replacement of DZNep by SAH hydrolase inhibitors ((−) Neplanocin A (Nep A), Adenosine periodate (oxidized) Adox and 3-deazaadenosine (DZA)) ((Chiang, et al., *Pharmacol. Ther.*, 77:115-134 (1998), Gordon, et al., *Eur. J. Biochem.* 270:3507-3517 (2003)), in combination with VC6TF treatment to induce CiPSC generation is shown in FIG. 14B The data shows that NEPA, ADOX and DZA are each useful in replacing DZNep in reprogramming. They modulate the same target as DZNep, and can substitute DZNep in generating CiPSCs.

Figure 11L:
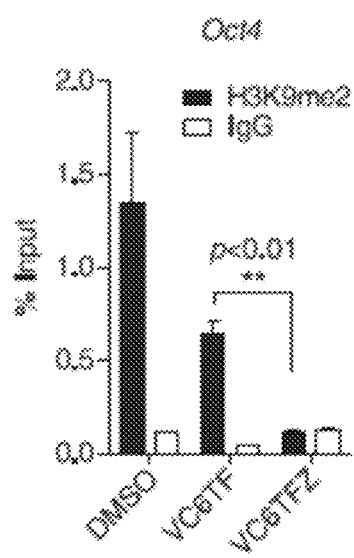
FIG. 11L shows H3K9 methylation in the presence and absence of DZNep on day 32.

Consistently, DZNep significantly decreased DNA methylation and H3K9 methylation (FIG. 11L) at the Oct4 promoter, which may account for its role in Oct4 activation (Feldman, et al., *Nat. Cell Biol.*, 8:188-194 (2006); Chen, et al., *Nat. Genet.*, 45:34-42 (2013)). The function of DZNep in inducing CiPSCs could not be replaced by down-regulating Ezh2 expression (FIGS. 14C-E). GFP+/ES-like colonies in the primary culture, unlike other colonies, express high mRNA level of Nanog and low level of Gata6, resembling ESCs and the established CiPSCs (data not shown). As master pluripotency genes, Oct4 and Sox2 may thereby activate other pluripotency-related genes and fulfill the chemical reprogramming process, along with the activation of Nanog and the silencing of Gata6, in the presence of 2i (Silva, et al., *PLoS Biol.* 6: e253 (2008), Theunissen, et al., *Curr. Biol.*, 21:65-71 (2011). Boyer, et al., Cell, 122:947-956 (2005); Chazaud, et al., Dev. Cell, 10:615-624 (2006)).

In summary, as a master switch governing pluripotency, Oct4 expression, which is kept repressed in somatic cells by multiple epigenetic modifications, is unlocked in chemical reprogramming by the epigenetic modulator DZNep and stimulated by C6F-induced expression of Sox2 and Sall4 (FIG. 13G).

Initial Gene Activation was Conserved in Chemical Reprogramming from Different Cell Types At the initial stage of chemical-induced reprogramming to pluripotency, NSCs and IECs were transformed into highly refractive phase-bright and epithelial-like cells, which share similar morphology of partial colonies during MEF chemical reprogramming. Compact epithelioid colonies were observed around day 20-32 (data not shown), and all CiPSC colonies were derived from these epithelioid colonies in at least ten independent experiments. Time-course quantitative real-time PCR was performed during the chemical reprogramming of NSCs and IECs. The data analysis results showed that during reprogramming of NSCs and IECs, a pluripotency gene Sall4, and differentiation-associated genes Gata4, Gata6 and Sox17, were activated as early as day 4 and increased with time in the early stage, while other pluripotency genes such as Lin28a, Dppa2, Esrrb and Oct4 were activated much later (FIGS. 15B, 15C and 15E), which is similar to the chemical reprogramming process from MEFs. Additionally, no innate expression of Sall4, Gata4, Gata6 and Sox17 were detected in NSCs (FIG. 15D and data not shown). Interestingly, fine-tuning the concentration of 616452, which is critical for the reprogramming of different cell types reprogramming, results in higher gene expression of Sall4, Gata4 and Sox17 (FIGS. 15F and 15D). These results suggest that the chemical reprogramming from cell types of all three germ layers shares the similar initial gene activation programs, regardless of cell origins and innate cellular features.

Figure 15A:
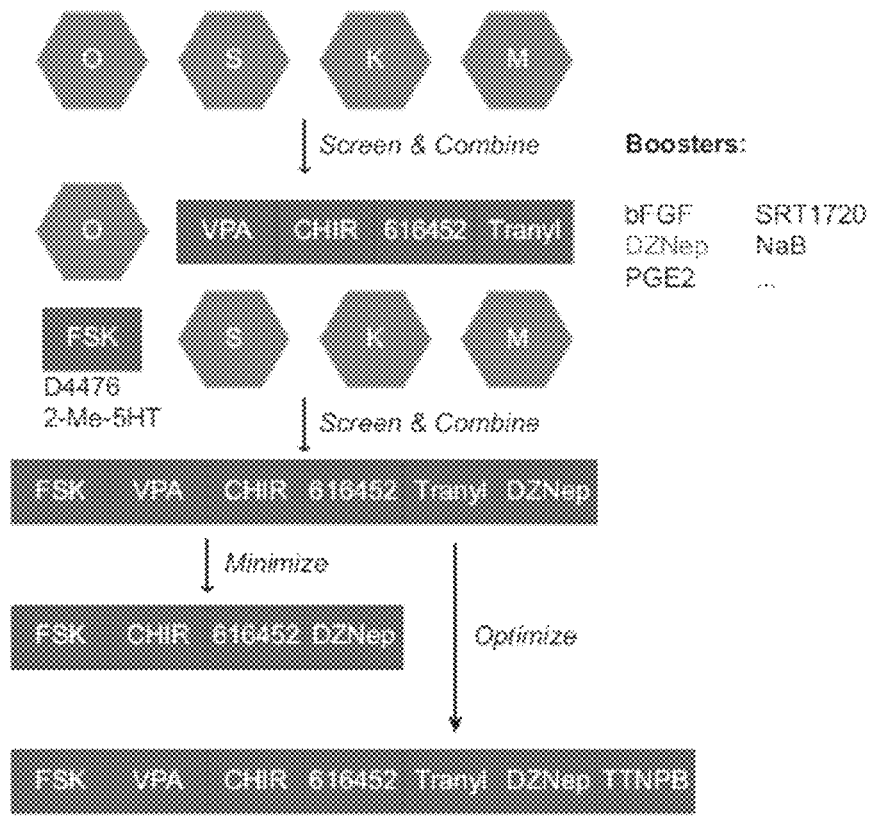
FIG. 15A is a schematic representation of the major steps in the development of chemical reprogramming systems. The blue hexagons represent reprogramming transcription factors, and the red squares represent the major small molecules identified at each step. Reprogramming boosters are displayed on the right, corresponding to different reprogramming conditions. The alternative Oct4 substitutes D4476 and 2-Me-5HT are displayed below FSK. Abbreviations: O (Oct4), S (Sox2), K (Klf4), M (c-Myc), Tranyl (Tranylcypromine).
Figure 15B:
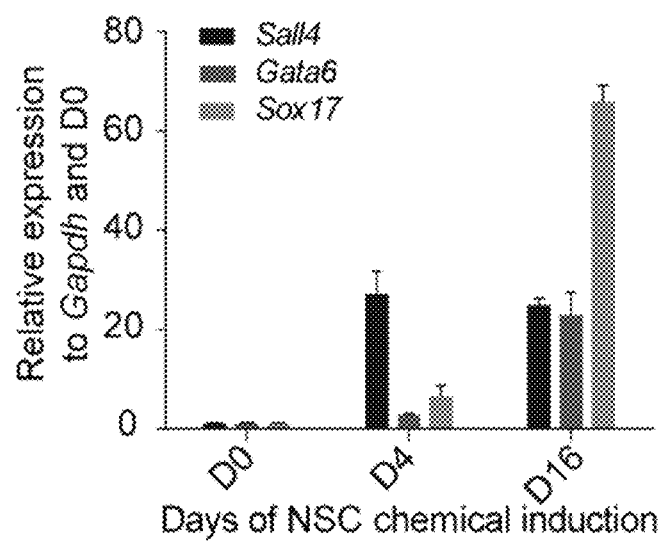
FIGS. 15B and 15C show expression of Sall4, Gata4 and Sox17 genes at the early stage of chemical reprogramming from NSCs (FIG. 15B) and IECs (FIG. 15C) at day 0 (DO)), day 4 (D4) and day 16 (D16), respectively, measured by quantitative real-time PCR.
Figure 15C:
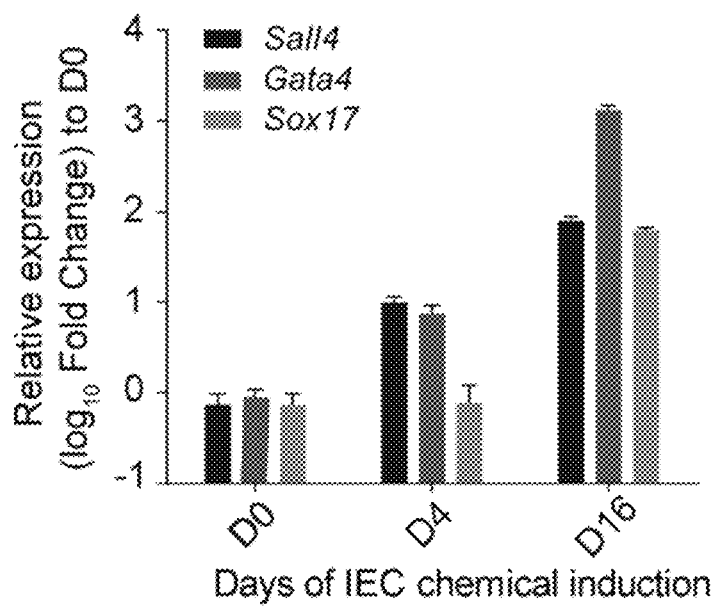
Figure 15D:
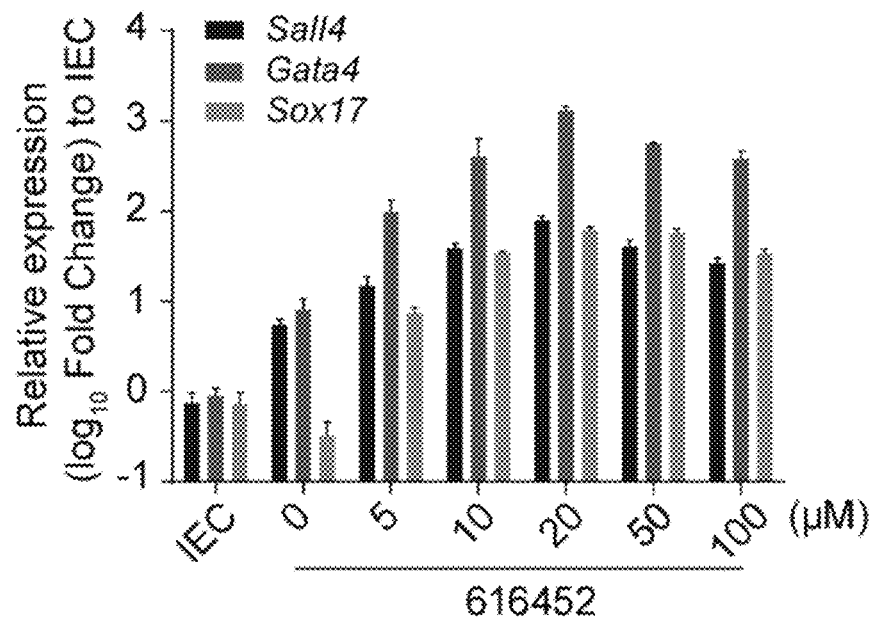
FIGS. 15D and 15F show expression of Sall4, Gata4 and Sox17 genes by the chemical cocktail with different concentration of 616452 at day 16 (FIG. 15F) and day 20 (FIG. 15D) (error bars, mean±SD, n=3).
Figure 15E:
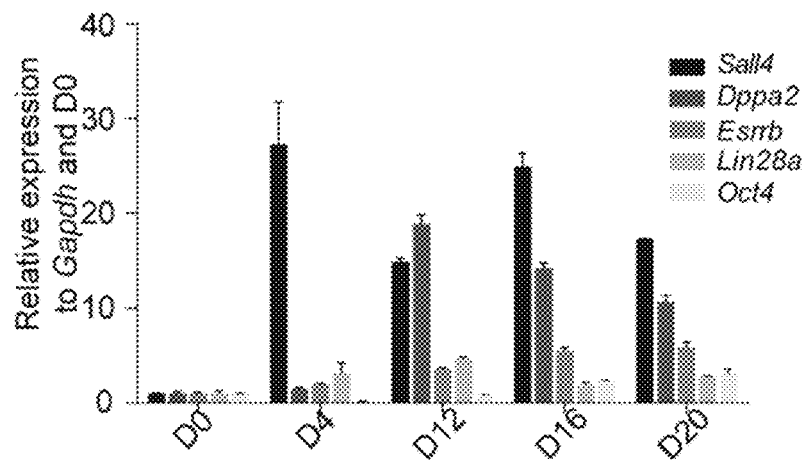
FIG. 15E shows expression of pluripotency genes Sall4, Lin28, Esrrb, Dppa2 and Oct4 during the chemical reprogramming from NSC (day 0 (DO), day 4 (D4), day 12 (D12), day 16 (D16) and day 20 (D20), respectively) measured by quantitative real-time PCR. FIG.
Figure 15F:
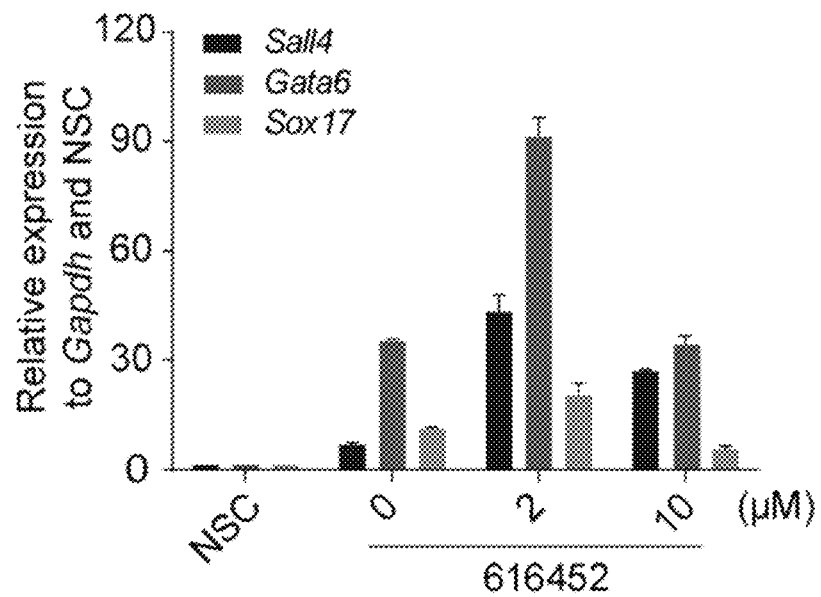
Figure 15G:
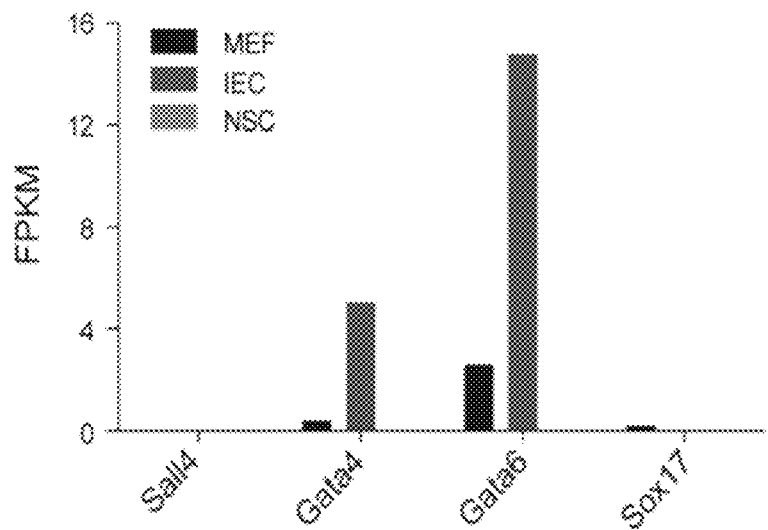

This proof-of-principle study demonstrates that somatic reprogramming toward pluripotency can be manipulated using only small-molecule compounds (FIG. 15A). It established that the endogenous pluripotency program can be established by the modulation of molecular pathways non-specific to pluripotency via small molecules rather than by exogenously provided "master genes." These findings understanding of the establishment of cell identities and open up the possibility of generating functionally desirable cell types in regenerative medicine by cell fate reprogramming using specific chemicals or drugs, instead of genetic manipulation and difficult-to-manufacture biologics.

In sum, the present data establishes that although a similar chemical cocktail is generally required for different cell types, fine-tuning the treatment of small molecules allows for improved reprogramming initiation in different cell types. Especially for the chemical reprogramming of NSCs, the concentration 616452, should be reduced to 2 µM in comparison of 10 µM, which is used on MEFs. Notably, the reduced 616452 concentration resulted in enhanced expression of Sall4 and Gata4 genes (FIG. 15D), which further supports the role high expression of these genes in chemical initiation of pluripotency. In addition, 616452 shows different function in chemical reprogramming and traditional transcription factor-induced reprogramming. In traditional transcription factor-induced reprogramming, ectopic expression of Oct4 and Klf4 or c-Myc is sufficient to generate iPS cells from NSCs, in the absence of exogenous Sox2 (Kim et al., 2008). Besides, 616452, also named as RepSox, was reported to substitute for Sox2 overexpression in traditional transcription factor-induced reprogramming (Ichida et al., 2009). However, by contrast, in chemical reprogramming from NSCs, 616452 cannot be removed, despite the high endogenous expression of Sox2. In chemical reprogramming, 616452 rather facilitates the early expression of Sall4, Gata4, Gata6 and Sox17 and the subsequent epithelioid colony formation (FIGS. 15F and 15D). These findings indicate that chemical reprogramming is a different process from transcription factor-induced reprogramming.

Interestingly, the reprogramming kinetics and frequency of NSCs and IECs are distinct from each other. The former underwent a longer early stage, with less epithelioid colonies generated, but almost 100 percent of the colonies could be converted into CiPSC colonies. In contrast, the latter could easily form more epithelioid colonies, but only 20-30 percent of these colonies were converted into CiPSC colonies.

Example 6. Identification of the Induction of Cell Colonies Expressing XEN Cell Markers as a Cornerstone Event During Chemical Reprogramming In the method for inducing pluripotent stem cells from non-pluripotent stem cells described in Hou et al., *Science* 341, 651-654 (2013)), there are three essential stages in the chemical reprogramming process. Reprogramming of cells into CiPSC was obtained a cocktail of five small molecules, "VC6TF" was used in stage 1 for 16-20 days, following which, another small molecule, DZNep, was added at the start of stage 2 (i.e., VC6TFZ) for the next 20-24 days, and 2i-medium was used in stage 3 for the last 12-16 days, in some cases adding additional small molecules. In total, the chemical reprogramming process can take as long as 48-60 days, resulting in a maximum of about 40 colonies (FIG. 19A).

In order to improve on the efficiency of reprogramming non-pluripotent cells into CiPSC, studies were conducted to characterize the chemical reprogramming process, by carefully following the change in cell morphology during chemical reprogramming in each stage. These studies revealed a number of epithelial colonies formed at the end of stage 1, which rapidly expanded during stage 2. By tracing the dynamic changes in cell fate during chemical reprogramming, these studies revealed that CiPSCs predominantly emerged from the inside of these epithelial cell colonies (FIG. 16A). In some experiments, 100% of the CiPSCs were generated from these colonies, even when the cells were re-plated at a lower density; the epithelial cell colonies had grown to less than 20% confluence. These findings indicate that there exist a subpopulation of cells during reprogramming, which are better primed for conversion into CiPSCs.

Immunofluorescence and quantitative real-time PCR (qRT-PCR) was then used to examine the gene expression pattern of these epithelial cell colonies. Immunofluorescence showed that all epithelial colonies formed in the end of stage 1 co-expressed SALL4, GATA4 and SOX17, master genes of XENs (Lim et al., *Cell Stem Cell.*, 3:543-554 (2008)) (data not shown). qRT-PCR analysis further detected the expression of other XEN marker genes, such as Sox7 and Gata6 in these colonies (FIG. 16B), which were comparable to that of embryo-derived XEN cells (eXENs) (Kunath et al., 2005) (FIG. 16C). These epithelial cells expressing XEN markers are referred to herein as XEN-like cells.

Studies were further conducted to determine whether these XEN-like cells represent an intermediate state of chemical reprogramming. Using a XEN-expressing surface protein, EpCAM, XEN-like cells were enriched at day 20 by FACS sorting and found that selection for EpCAM-positive cells greatly enriched the proportions of cells forming XEN-like cell colonies and subsequently generating CiPSCs by more than 20-fold (FIGS. 16C and 16D). Similar results were obtained when the starting cells were neural stem cells and intestinal epithelium cells. EpCAM also strongly enriched the cells that formed XEN-like colonies during chemical reprogramming and improved the ability to generate CiPSCs from these two initial cell types (FIG. 16E). To determine whether there exist transitional colonies which co-expressed XEN master genes and pluripotency-associated genes if pluripotent stem cells were induced from XEN-like cells, expression of two markers was assessed in stage 2. Cells that co-expressed GATA4 and OCT4 were detected during stage 2 of reprogramming (data not shown). Cell colonies expressing GATA4 in the peripheral, and expressing pOct4-GFP in the middle of the colonies were identified in in stage 3, which could be the intermediate cell colonies of the cell fate transition from XEN-like to pluripotent stem cells (data not shown). Together, these results indicate that the XEN-like cells represent an intermediate state of chemical reprogramming toward pluripotency.

Example 7. Identification of Small Molecules that Promote the Transition from Fibroblasts to XEN-Like Cells The identification of an intermediate state of chemical reprogramming in Example 6 provides a target for enhancing reprogramming conditions and for screening novel small-molecule boosters in early reprogramming by using XEN-like colony numbers as the readout. Increased concentration of CHIR99021 is proved beneficial for the formation of XEN-like colonies from MEFs (FIG. 17A). Through qRT-PCR analysis showed that this increased concentration of CHIR99021 promotes an up to 10-fold increase in the expression of XEN master genes Gata4 and Sox17 and an epithelium cell marker, EpCAM (FIGS. 17B and 17C).

Next, the effects of a selected small-molecule library of previously reported reprogramming boosters was tested in the presence of a small-molecule cocktail, VC6TF, with 20 µM CHIR99021, on the reprogramming of cell fate from fibroblasts to XEN-like cells. Among the tested small molecules, an RA agonist, AM580 (A), and a DOT1L inhibitor, EPZ004777 (E), each enhanced the formation of XEN-like colonies by 2 to 3-fold When these small molecules were used together in a cocktail of seven small molecules, VC6TFAE, the number of XEN-like colonies was enhanced by more than 5-fold (FIG. 17D). These findings were further validated by counting the numbers of SALL4 and GATA4 double-positive colonies and by detecting the expression of XEN marker genes by qRT-PCR (FIG. 17E-I). Together, the numbers of XEN-like colonies, an indicator of early reprogramming, could be enhanced more than 50-fold by selecting a combination of small molecule concentrations and additional small molecules type included in the cell culture medium.

Example 8. The Identification of Small Molecules that Promote the Transition from a XEN-Like to a Pluripotent State Studies were next conducted to identify small molecules that facilitate the transition of XEN-like colonies to CiPSCs during stages 2 and 3. Small-molecule screenings were performed in the presence of small molecule cocktail VC6TFA plus DZNep (Z) for 12 days with successful enhanced generation of CiPSC colonies. By contrast, in Hou et al., Science 341:651-654 (2013), the optimal duration for stage 2 was 20-24 days; few CiPSC colonies were obtained if stage 2 was shortened to 12 days.

After selecting and screening 88 small molecules, it was discovered that CiPSC colonies formed in stage 3 only when the cell culture medium was supplemented with 5-aza-dC during stage 2. 5-aza-dC (D) and EPZ004777 (E) had synergistic effects and promoted the kinetics of stage 2. Thus, by using a cocktail of eight small molecules, VC6TFA+ZDE, for 12 days during stage 2, up to 20 CiPSC colonies were obtained from 100,000 re-plated cells at the end of the reprogramming process of 44 days (FIG. 18A). In contrast, few CiPSC colonies were obtained during the same time course without 5-aza-dC and EPZ004777. When another DOT1L inhibitor, SGC0946 (S) was used in place of EPZ004777 during stage 2, however, the reprogramming efficiency was increased further by as much as 5-fold at a replating density of 100,000 or 20,000 cells per well in a 6-well plate (FIG. 18A-C) (original cell density of 300,000 to 500,000 cells per well in a 6-well plate), particularly when a further supplemented 2i-medium (N2B27-2i medium) was used (FIGS. 18B and 18C). Next, the effect if any, of replating density and concentration of small molecules the on the number of CiPSC colonies obtained was investigated. Using the small-molecule cocktail VC6TFA+ZDS during stage 2 for 12 days, approximately 100-600 CiPSC colonies was obtained from 50,000 re-plated cells during the final stage of chemical reprogramming. The data showed that although SGC0946 can be more effective than EPZ004777 during stage 2, SGC0946 could not substitute for EPZ004777 during stage 1 because cell viability was decreased if SGC0946 was used from the start of chemical reprogramming. (FIG. 18D-18G). Importantly, CiPSC colonies emerged from 24-53% of the XEN-like colonies in five independent experiments, indicating the transition ratio of a single XEN-like cell in the start of stage 2 to CiPSCs in the end of stage 3 (FIG. 18H-I). In addition, almost all CiPSC colonies were derived from XEN-like colonies, even though the efficiency was greatly improved (FIG. 18I).

These studies showed that the duration of the small-molecule treatment and the re-plating cell density were both highly critical during the later stages of reprogramming. The previous studies which did not follow a reprograming route of biasing/enriching the XEN-like cell population favors a re-plating cell density of 300,000 cells per well (Hou et al., (2013)). However, when CiPSC reprograming progresses via enriching for the XEN-like cells, it is preferable to replate cells at a cell density of 50,000-100,000 cells per well of a 6-well plate (FIG. 18D). Furthermore, the previously described protocol required 24 days of reprogramming during stage 2 to achieve optimal reprogramming efficiency ((Hou et al., (2013)). By contrast, a protocol which biases/enriches the XEN-like cell population as described herein requires an optimal stage 2 duration of 12 days (FIG. 18E).

In summary, the methods disclosed herein greatly improve the cell transition from non-pluripotent into pluripotent cells, by selecting a first cocktail of small molecules to enrich/bias cells to be reprogrammed towards the XEN-like state, selecting a second cocktail of small molecules and replating density and cell culture time for transition from XEN to CiPSCs.

Example 9. Establishment of a Robust CiPSC Induction Protocol was Established Through Modulation of the Cell Transitions Through a XEN-Like State Next, reprogramming conditions for stages 1, 2 and 3 identified in Example 8 were combined to reprogram fibroblasts into CiPSCs. Using this new protocol, a well of 50,000 initial fibroblasts was induced, and the cells were expanded to more than 1,000,000 or more re-plated cells (re-plated into 10-15 wells). A total of 1,000-9,000 CiPSC colonies were obtained at the end of the reprogramming period with a total induction time of 40 days (16, 12, and 12 days for stages 1, 2 and 3, respectively). A comparison of the reprogramming protocol which includes biasing towards XEN-like cells and the previous protocol exemplified in Example 3 is shown in FIG. 19A. Moreover, this new protocol was reproduced independently more than 20 times, and CiPSCs could also be generated from neonatal dermal fibroblasts (MNFs) and adult lung fibroblasts (MAFs) at a significantly enhanced efficiency (FIG. 19B).

The minimal time course required in inducing CiPSCs was further examined by using this new small-molecule cocktail and the reprogramming conditions established in Example 8. A minimum of 12 days were required in the formation of XEN-like colonies (cells were re-plated at day 8), and that at least another 14 days were required to induce CiPSCs from XEN-like cells (FIG. 19C). In total, at the cost of efficiency, a minimum of 26 days are required to induce CiPSCs by using the new protocol (FIG. 19C). In comparison, at least 44 days were required to generate only 0-1 CiPSC colony from 40,000 initial cells using the original protocol, and up to about 40 CiPSC colonies could be generated if the treatment time frame was extended to more than 60 days (Table 1A).

CiPSC colonies were then picked to establish CiPSC lines for further characterization. As shown by immunostaining and qRT-PCR, the CiPSCs expressed all the tested marker genes for pluripotent stem cells, such as Oct4, Sox2 and Nanog (FIG. 19D, 19E). RNA-seq analysis showed that CiPSCs induced with this protocol had gene expression profiles similar to those of ESCs (data not shown). CiPSCs were further tested for their potential for in vivo development. All tested 6 CiPSC lines were able to form teratoma after injection into SCID mice (data not shown) and generate chimeric mice after blastocyst injection (data not shown). Among 5 tested CiPSC lines, 4 lines showed germ line integration potential in chimeric mice (data not shown). Moreover, CiPSCs were maintained with normal karyotypes (data not shown). Together, these results establish a robust CiPSC induction protocol, obtained by manipulating the cell fate transition more precisely through the XEN-like state.

Gene Expression Dynamics During CiPSC Generation

Expression of some typical pluripotency-associated genes during chemical reprogramming was examined at different stages of chemical reprogramming. The data showed sequential expression of pluripotency genes (FIG. 20A).

Single cell qRT-PCR analysis showed that approximately 50% of the cells in stage 2 co-expressed XEN cell markers (FIG. 20B). Similar to embryo-derived XEN cells, the XEN-like cells formed during chemical reprogramming expressed several pluripotency genes, such as Sall4 and Lin28a, during the early stages of reprogramming (Lim et al., *Cell Stem Cell,* 3:543-554 (2008); McDonald et al., *Cell Reports,* 9:780-793 (2014). During an extended time in culture, the XEN-like cells expressed other pluripotency-associated genes on days 16-28, such as Oct4 and Dppa2. During stage 3, the expression of most pluripotency marker genes, including Nanog, was activated in CiPSCs (FIGS. 20A and 20C). This finding indicates a process of sequential gene activation from XEN-like cells to pluripotent stem cells. Interestingly, Sall4, Lin28a, Esrrb, the major genes associated with pluripotency that are highly expressed during stages 1 and 2 of cell reprogramming, have previously been reported to be predictive markers of transcription factor-induced reprogramming and to be sufficient for inducing iPSCs with high quality when concomitantly expressed with Nanog (Buganim et al., *Cell,* 150:1209-1222 (2012); Buganim et al., *Cell Stem Cell,* 15:295-309 (2014)).

Through qRT-PCR analysis and RNA sequencing, AM580 and EPZ004777 were identified as molecules which both promote the expression of XEN marker genes, such as Sall4, Gata4 and Sox17, during stage 1 of chemical reprogramming from fibroblasts to XEN-like cells (FIG. 17F). SGC0946 and 5-aza-dC promote the expression of pluripotency genes, such as Oct4 and Dppa family genes in XEN-like cells, during stage 2 of chemical reprogramming (FIG. 20D). These findings indicate that stage 1 of chemical reprograming into XEN-like cells is promoted by additional small molecules that act by enhancing the expression of XEN master genes, and stage 2 can be shortened possibly due to the enhanced activation of pluripotency-associated genes by additional small molecules. Studies were next conducted to determine whether the reprogramming process through a XEN-like state is a unique route towards pluripotency compared to that of the transgenic strategy, which uses OSKM (Takahashi et al., *Cell,* 131:861-872 (2007); Takahashi et al., *Nature Communications* 5:3678 (2014); Takahashi and Yamanaka, *Cell,* 126:663-676 (2006). Notably, OSKM-induced reprogramming processes do not show XEN-like gene profiles, analyzed by qRT-PCR (FIG. 20C). This finding was also consistent with the original data from RNA sequencing or microarray during the reprogramming process in other reports (Golipour et al., *Cell Stem Cell* 11:769-782 (2012); Mikkelsen et al., *Nature,* 454:49-55 (2008); Polo et al., *Cell* 151:1617-1632 (2012); Sridharan et al., *Cell* 136:364-377 (2009).

Also examined was whether primitive streak genes were expressed during the chemical reprogramming process, because a primitive streak state has been reported during the process of OSKM-induced reprogramming (Takahashi et al., *Nature Communications,* 5:3678 (2014)). The expression of primitive streak markers, such as T and Mix11, was not detected during chemical reprogramming (data not shown), demonstrating a unique XEN-like state during the chemical reprogramming process, which differs from that of the reprogramming induced by transgenes (FIG. 20E).

XEN Master Gene Expression is Essential During Chemical Reprogramming

To further support the XEN state as an intermediate for chemical reprogramming and to understand the role of XEN master genes in chemical reprogramming, knockdown and ectopic expression experiments were performed. Knockdown of any one of the key XEN genes Sall4, Gata4, Gata6 or Sox17 led to a significant down regulation in the mRNA levels of the other XEN genes and decreased XEN-like colony numbers, thus resulting in less Oct4 expression and fewer CiPSCs at the end of the reprogramming period (FIGS. 21A-E). The expression of XEN genes was essential to Oct4 expression. XEN-gene expression was also enhanced in chemical reprogramming from neural stem cells and intestinal epithelium cells (data not shown), and the knockdown of these genes impaired XEN-like colony formation and further CiPSC induction from these two initial cell types (FIG. 21F). These results further indicate that the XEN-like state is essential to the chemical reprogramming process. In contrast, these XEN master genes, such as Gata4, Gata6 and Sox17, were not required in OSKM-induced reprogramming (FIG. 21G), which suggest different roadmaps underlying chemical reprogramming and OSKM-induced reprogramming (20E).

Furthermore, the overexpression of two of the XEN master genes (SALL4 plus GATA4 or SALL4 plus GATA6) in fibroblasts sufficed in inducing XEN-like colony formation in the absence of the three key small molecules, CHIR99021, 616452 and Forskolin (FIG. 21H). The resulting XEN-like cells showed gene expression pattern similar to that of the small molecule-induced XEN-like cells (FIG. 21I). Moreover, Oct4 expression was detected in the XEN-like colonies induced by the two combinations of XEN cell master transcription factors (FIG. 21J and data not shown). These findings suggest that XEN genes are both necessary and sufficient to initiate the expression of Oct4, a master gene of pluripotency.

Notably, although these XEN master gene-induced XEN-like cells expressed Oct4, they could not be further reprogrammed into iPSCs, even with a prolonged culture in 2i-medium. Exogenous XEN genes downregulated the endogenous expression of Sox2 (FIG. 21K). Accordingly, when Sox2 was exogenously provided in an appropriate time window after XEN gene overexpression, iPSCs were obtained (FIG. 21L and data not shown). This finding is consistent with our previous findings of a seesaw model in regulating pluripotency establishment, in which the Gata family genes and Sox2 should be in a balance to achieve pluripotency (Shu et al., *Cell,* 153:963-975 (2013), whereas in chemical reprogramming such a balance could be a dynamic process rather than a steady equilibrium.

The XEN-Like Intermediates Resemble Embryo-Derived XEN Cells in Gene Expression Patterns, In Vivo Development Potential and Reprogramming Potential Chemically-induced XEN-like cells were compared to embryo-derived XEN cells (eXENs) (Kunath et al., *Development* 132:1649-1661 (2005) with respect to in vitro culture conditions. The studies showed that XEN-like cells could not be maintained in the traditional XEN culture medium (RPMI CM (traditional XEN culture medium; RPMI-medium with 70% MEF-condition medium (Kunath, et al., *Development,* 132:1649-1661 (2005)) (data not shown). In addition, eXEN cell lines could be maintained long-term and expanded in the stage 1 medium of chemical reprogramming for more than 20 passages, with the gene expression pattern and in vivo development potential similar to eXENs maintained in traditional XEN medium (data not shown).

By using stage 1 medium including chemical cocktail VC6TF, chemically-derived eXEN cell lines (CeXENs) could be established directly from blastocysts and expanded long-term for more than 25 passages, with a XEN-like gene expression pattern and in vivo integration capability into extraembryonic parietal endoderm (FIGS. 22A-B, Table 7, and data not shown).

TABLE 7

Statistical table of XEN integration chimeric ability of different cell types as indicated to parietal endoderm. EGFP-labeled fibroblasts were set as negative control.

| Cell Type | No. of embryos red (E6.5-8.5) | Xen integration |
| --- | --- | --- |
| Xen-like D11 | 18 | 7 (39%) |
| Xen-like D116 | 24 | 21 (88%) |
| Xen-like D125 | 22 | 10 (45%) |
| eXen-1 | 31 | 20 (65%) |
| eXen-2 | 23 | 9 (39%) |
| CeXen | 20 | 7 (35%) |
| Fibroblasts | 10 | 0 | qRT-PCR analysis showed that XEN-like cells express a comparable level of XEN master genes to that of eXENs and CeXEN (FIGS. 16B, 22A and data not shown). Global gene expression profiling at the end of stages 1 and 2 showed that XEN-like cells showed gene expression profiles close to eXENs and CeXENs (FIG. 22B). Principal component analysis (PCA) analysis of gene expression profiling showed a clear roadmap from fibroblasts toward pluripotent stem cells through such a XEN-like state close to eXENs and CeXENs (data not shown).

In particular, the XEN-like intermediates in chemical reprogramming were closer to CeXENs than traditional eXENs in gene expression profiles (FIG. 22B and data not shown). Moreover, mRNA level of EpCAM, Cdh1 and Sox2 in XEN-like cells and CeXENs was notably higher than that in traditional eXENs (FIG. 22C). It is possible that the differences of the gene expression pattern between XEN-like cells and traditional eXENs were resulted from their different culture conditions. Interestingly, authentic XEN cells in vivo express EPCAM and CDH1 in a high level comparable to that of ESCs and express SOX2 in a relatively low level, a pattern similar to that of XEN-like cells and CeXENs, but not eXENs (FIG. 22D). This suggests that although XEN-like cells showed some differences to eXENs in culture conditions and gene expression patterns, they were more similar to CeXEN, another type of embryo-derived XEN cells.

The in vivo development potential of XEN-like cells during chemical reprogramming was also examined. XEN-like cells induced in different time courses of chemical reprogramming were injected into mouse blastocysts. Similarly to eXEN cells, XEN-like cells at days 11-25 of chemical reprogramming were able to integrate into the parietal endoderm of the extraembryonic tissues with a comparable efficiency of eXENs, without any integration in the embryos (data not shown and Table 7). In particular, XEN-like cells in day 16 of chemical reprogramming showed the highest ratio of XEN integration (Table 7). These findings suggest that XEN-like cells resemble embryo-derived XEN cells in terms of development potential.

Furthermore, either eXENs derived by traditional XEN culture medium or CeXENs established by the stage 1 medium of chemical reprogramming, were capable of further reprogramming into CiPSCs by using the protocol of late chemical reprogramming in stages 2 and 3 (data not shown). Notably, 17-34 CiPSC colonies were generated from 2,000 CeXENs within 24 days, a reprogramming efficiency even higher than that of XEN-like cells.

CiPSCs generated from eXENs and CeXENs were further characterized to possess an expression pattern similar to pluripotency stem cells (FIG. 22D and data not shown). These findings further support that XEN-like cells induced in the early stage of CiPSC generation, which were similar to CeXENs, were amenable to being further reprogrammed in the late stage of chemical reprogramming.

Discussion

In summary, we demonstrated a XEN-like state as an intermediate for chemical reprogramming, which differs from other reprogramming scenarios. The chemical reprogramming process can be divided into two major steps. In the first step of reprogramming, fibroblasts are directly converted into XEN-like cells, whereas in the later step of reprogramming, XEN-like cells are converted into CiPSCs (FIG. 15D).

The determination of the role of a XEN-like state in chemical reprogramming uncovered a unique route in chemical reprogramming of somatic cells toward pluripotency, but not in OSKM-induced reprogramming (FIG. 20E). This route also differs from a primitive streak-like state mediated reprogramming process induced by transcription factors (Takahashi et al., Nature Communications 5:3678 (2014)). In addition, fibroblasts from mouse embryos were induced into a cell type resembling extraembryonic lineages in chemical reprogramming process, which is definitely not a reversed normal development process with multiple transient waves of gene expression changes as recently reported (Cacchiarelli et al., Cell 162:412-424 (2015)). The XEN-like state is also required to generate CiPSCs from other cell types, such as neural stem cells and intestinal epithelium cells, indicative of a general pathway to reprogram other cell types using small molecules. Interestingly, the XEN-like cells induced during chemical reprogramming are similar to embryo-derived XEN cells in gene expression pattern, development potential and reprogramming potential. These in together provide a new framework to further study cell fate determination of XEN cells and pluripotent cells and the transition of these cell fates.

Moreover, the XEN-like state is unique, as it is primed to undergo further conversion to the pluripotency state. Similarly to XEN cells in vivo, the induced XEN-like cells have already expressed Sall4 and Lin28a, two master genes of pluripotency. It is possible that the shared genes that are expressed in both XEN cells and pluripotent stem cells, such as Sall4 and Lin28a, make the pluripotency state more accessible during the cell fate transition from the XEN-like state to pluripotency. Moreover, sequential expression of many pluripotency marker genes in XEN-like cells, during stage 2 of chemical reprogramming was also demonstrated. For example, the expression of Esrrb and Oct4 was activated, and the expression of Oct4 was compatible with the expression of XEN genes. This finding indicates that the pluripotency network is easily established in XEN-like cells. This finding is consistent with the recent report that in vivo XEN cells spontaneously transition into epiblast stem cells, which are in a primed pluripotency state (Xenopoulos et al., Cell Reports, 10:1508-1520 (2015). The compatibility of XEN-like genes and the expression of pluripotency genes make the XEN-like state an ideal bridge between somatic cells and pluripotent cells.

These studies establish that XEN-like state is essential for inducing pluripotency during chemical reprogramming, possibly because that the master genes of XEN directly contribute to the establishment of pluripotency. In addition, the studies suggest that XEN-like genes may have dual roles in chemical reprogramming. As previously reported, there are several mutual antagonistic mechanisms between XEN genes and pluripotency-associated genes, such as the incompatibility between Sox17 and Sox2 and between Gata6 and Nanog (Aksoy et al., *The EMBO Journal* 32:938-953 (2013); Chazaud et al., *Developmental Cell*, 10:615-624 (2006; Niakan et al., *Genes & Development*, 24:312-326 (2010). In this study, the expression of Sox2 was repressed by the XEN genes. Further, during stage 3 of chemical reprogramming, the expression of Nanog and Sox2 was incompatible with the expression of Gata4, reminiscent of the cell fate determination between XENs and epiblasts regulated by FGF/ERK signaling in the mouse blastocyst as previously reported (Yamanaka et al., *Development*, 137: 715-724 (2010). During the early stage of chemical reprogramming, the XEN state is necessary to initiate the expression of select pluripotency genes, such as Sall4, Lin28a and Oct4. However, in the later stage of reprogramming, these XEN genes need to be silenced to initiate the expression of additional pluripotency genes, such as Nanog and Sox2.

Most important, in this study, chemical reprogramming was greatly improved by manipulating cell fate transitions through the XEN-like state, through careful selection the small-molecule cocktails which bias cells towards the XEN-like state, and then CiPSC, concentrations, durations and other details of cell manipulation during each stage, greatly improving the efficiency of CiPSC generation and increasing the total yields of CiPSC colonies by up to 1,000-fold compared a chemical reprogramming protocol which does not proceed via biasing to a XEN-like state as described herein.

We claim:

1. A method of inducing pluripotency in partially or completely differentiated cells, the method comprising:
   (a) contacting the partially or completely differentiated cells with a first cocktail comprising VC6TFAE (XEN-Cocktail) for a sufficient period of time to obtain XEN-like cells;
   (b) contacting the XEN-like cells for a sufficient period of time to reprogram the XEN-like cells into chemically induced pluripotent stem cells (CiPSCs) with a second cocktail comprising VC6TFZASD (XEN-CiPSC cocktail); and
   (c) culturing the CiPSCs in 2i-medium,
   wherein V is valproic acid,
   C is [6-[[2-[[4-(2,4-Dichlorophenyl)-5-(5-methyl-1H-imidazol-2-yl)-2-pyrimidinyl]amino]ethyl]amino]-3-pyridinecarbonitrile] (CHIR99021),
   6 is [2-(3-(6-Methylpyridin-2-yl)-1H-pyrazol-4-yl)-1,5-naphthyridine] (616452),
   T is tranylcypromine,
   F is Forskolin,
   A is (4-[(5,6,7,8-Tetrahydro-5,5,8,8-tetramethyl-2-naphthalenyl) carboxamido]benzoic acid) (AM-580),
   E is 1-(3-((((2R,3S,4R,5R)-5-(4-amino-7H-pyrrolo[2,3-d]pyrimidin-7-yl)-3,4-dihydroxytetrahydrofuran-2-yl) methyl) (isopropyl)amino) propyl)-3-(4-(tert-butyl) phenyl) urea (EPZ004777),
   Z is 3-deazaneplanocin A (DZNep),
   S is (1-[3-[[[(2R,3S,4R,5R)-5-(4-Amino-5-bromo-7H-pyrrolo[2,3-d]pyrimidin-7-yl)-3,4-dihydroxytetrahydrofuran-2-yl]methyl](isopropyl)amino]propyl]-3-[4-(2,2-dimethylethyl)phenyl]urea) (SGC 0946), and
   D is 5-azacytidine.

2. The method of claim 1, wherein the differentiated cells are selected from the group consisting of multipotent stem cells, cells of hematological origin, cells of embryonic origin, skin derived cells, fibroblasts, adipose cells, epithelial cells, endothelial cells, mesenchymal cells, parenchymal cells, neurological cells, and connective tissue cells.

3. The method of claim 1, wherein the partially or completely differentiated cells are selected from the group consisting of fibroblasts, adipose-derived cells, neural derived cells and intestinal epithelial cells.

4. The method of claim 1, wherein the partially or completely differentiated cells are not transfected to express markers selected from the group comprising Oct4, KLF4, SOX2, C-Myc and NANOG.

5. The method of claim 1, wherein the partially or completely differentiated cells are cultured in reprograming medium comprising the XEN-CiPSC cocktail for a period between 26-30 days.

6. The method of claim 1 wherein the XEN-Cocktail comprises VC6TFA the entire time before the use of 2i-medium.

7. The method of claim 1 wherein the partially or completely differentiated cells in step (a) are replated at a density between 50,000 to 100,000 per well in a 6-well plate between day 6-10.

8. The method of claim 1 wherein the chemically induced pluripotent stem cells are transferred to 2i-medium between day 26 and day 30.

9. The method of claim 8 wherein the 2i-medium further comprises N2B27, wherein N2 is N2 supplement, and wherein B27 is B27 supplement.

10. The method of claim 8 wherein the chemically induced pluripotent stem cells are cultured in 2i-medium for about 10-14 days.

11. The method of claim 1 wherein the XEN-Cocktail, the XEN-CiPSC cocktail, or both the XEN-Cocktail and XEN-CiPSC cocktail further comprise small molecules that facilitate late reprograming selected from the group consisting of cAMP agonists, epigenetic modulators and small molecules that boost chemical reprograming efficiency.

12. The method of claim 1 wherein the XEN-cocktail does not comprise SGC 0946.

13. The method of claim 1, wherein the XEN-Cocktail, the XEN-CiPSC cocktail, or both the XEN-Cocktail and XEN-CiPSC cocktail comprise a small molecule which boosts reprograming efficiency, wherein the small molecule is [4-[(E)-2-(5,6,7,8-Tetrahydro-5,5,8,8-tetramethyl-2-naphthalenyl)-1-propenyl]benzoic acid] (TTNPB).

14. The method of claim 1, comprising identifying the pluripotent cells based on possession of one or more ESC-like properties selected from the group consisting of morphology, doubling time, the ability of the cell to differentiate into tissues of the three embryonic germ layers, and expression of ESC markers.

15. The method of claim 14, wherein the ESC markers are selected from the group consisting of alkaline phosphatase (AP); nanog; Rex1; Sox2; Dax1; Sall4; undifferentiated embryonic cell transcription factor (Utf1); stage specific embryonic antigen-4 (SSEA-4) and combinations thereof.

16. The method of claim 1, further comprising isolating the pluripotent cells.

17. The method of claim 3, wherein the partially or completely differentiated cells do not express Oct4.

18. The method of claim 1 wherein the cells in step (a) are replated at a density between 50,000 to 100,000 per well in a 6-well plate at day 8.

19. The method of claim 1 wherein the chemically induced pluripotent stem cells are transferred to 2i-medium on day 28.

20. The method of claim 8 wherein the chemically induced pluripotent stem cells are cultured in 2i-medium for 12 days.

* * * * *

SEQUENCE LISTING

<160> NUMBER OF SEQ ID NOS: 73

<210> SEQ ID NO 1
<211> LENGTH: 35
<212> TYPE: DNA
<213> ORGANISM: Artificial Sequence
<220> FEATURE:
<223> OTHER INFORMATION: Synthetic Sall4 forward primer

<400> SEQUENCE: 1
actcgagcca ccatgtcgag gcgcaagcag gcgaa                                35

<210> SEQ ID NO 2
<211> LENGTH: 35
<212> TYPE: DNA
<213> ORGANISM: Artificial Sequence
<220> FEATURE:
<223> OTHER INFORMATION: Synthetic Sall4 reverse primer for plasmid
      construction

<400> SEQUENCE: 2
gcaattgtta gctgacagca atcttatttt cctcc                                35

<210> SEQ ID NO 3
<211> LENGTH: 22
<212> TYPE: DNA
<213> ORGANISM: Artificial Sequence
<220> FEATURE:
<223> OTHER INFORMATION: Synthetic Sox2 forward primer for qRT-PCR

<400> SEQUENCE: 3
cgggaagcgt gtacttatcc tt                                              22

<210> SEQ ID NO 4
<211> LENGTH: 21
<212> TYPE: DNA
<213> ORGANISM: Artificial Sequence
<220> FEATURE:
<223> OTHER INFORMATION: Synthetic SOX2 reverse primer

<400> SEQUENCE: 4
gcggagtgga aactttgtc c                                                21

<210> SEQ ID NO 5
<211> LENGTH: 22
<212> TYPE: DNA
<213> ORGANISM: Artificial Sequence
<220> FEATURE:

<223> OTHER INFORMATION: Synthetic Klf4 forward primer

<400> SEQUENCE: 5
ttgcggtagt gcctggtcag tt                                            22

<210> SEQ ID NO 6
<211> LENGTH: 22
<212> TYPE: DNA
<213> ORGANISM: Artificial Sequence
<220> FEATURE:
<223> OTHER INFORMATION: Synthetic Klf4 reverse primer

<400> SEQUENCE: 6
ctatgcaggc tgtggcaaaa cc                                            22

<210> SEQ ID NO 7
<211> LENGTH: 19
<212> TYPE: DNA
<213> ORGANISM: Artificial Sequence
<220> FEATURE:
<223> OTHER INFORMATION: Synthetic Oct 4 forward primer

<400> SEQUENCE: 7
cagggctttc atgtcctgg                                                19

<210> SEQ ID NO 8
<211> LENGTH: 20
<212> TYPE: DNA
<213> ORGANISM: Artificial Sequence
<220> FEATURE:
<223> OTHER INFORMATION: Synthetic Oct 4 reverse primer

<400> SEQUENCE: 8
agttggcgtg gagactttgc                                               20

<210> SEQ ID NO 9
<211> LENGTH: 24
<212> TYPE: DNA
<213> ORGANISM: Artificial Sequence
<220> FEATURE:
<223> OTHER INFORMATION: Synthetic forward Gata4 primer

<400> SEQUENCE: 9
gagctggcct gcgatgtctg agtg                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic Gata4 reverse primer

<400> SEQUENCE: 10
aaacggaagc ccaagaacct gaat                                          24

<210> SEQ ID NO 11
<211> LENGTH: 20
<212> TYPE: DNA
<213> ORGANISM: Artificial Sequence
<220> FEATURE:
<223> OTHER INFORMATION: Synthetic forward Gata6 primer

<400> SEQUENCE: 11
tgaggtggtc gcttgtgtag                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Gata6 reverse primer

<400> SEQUENCE: 12
atggcgtaga aatgctgagg                                              20

<210> SEQ ID NO 13
<211> LENGTH: 21
<212> TYPE: DNA
<213> ORGANISM: Artificial Sequence
<220> FEATURE:
<223> OTHER INFORMATION: Synthetic Sox17 forward primer

<400> SEQUENCE: 13
gtcaacgcct tccaagactt g                                            21

<210> SEQ ID NO 14
<211> LENGTH: 21
<212> TYPE: DNA
<213> ORGANISM: Artificial Sequence
<220> FEATURE:
<223> OTHER INFORMATION: Synthetic Sox17 reverse primer

<400> SEQUENCE: 14
gtaaaggtga aaggcgaggt g                                            21

<210> SEQ ID NO 15
<211> LENGTH: 19
<212> TYPE: DNA
<213> ORGANISM: Artificial Sequence
<220> FEATURE:
<223> OTHER INFORMATION: Synthetic Esrrb forward primer

<400> SEQUENCE: 15
gtggctgagg gcatcaatg                                               19

<210> SEQ ID NO 16
<211> LENGTH: 21
<212> TYPE: DNA
<213> ORGANISM: Artificial Sequence
<220> FEATURE:
<223> OTHER INFORMATION: Synthetic Errb reverse primer

<400> SEQUENCE: 16
aaccgaatgt cgtccgaaga c                                            21

<210> SEQ ID NO 17
<211> LENGTH: 21
<212> TYPE: DNA
<213> ORGANISM: Artificial Sequence
<220> FEATURE:
<223> OTHER INFORMATION: Synthetic Sall4 forward primer

<400> SEQUENCE: 17
tggcagacga gaagttcttt c                                            21

<210> SEQ ID NO 18
<211> LENGTH: 22
<212> TYPE: DNA
<213> ORGANISM: Artificial Sequence
<220> FEATURE:
<223> OTHER INFORMATION: Synthetic Sall4 reverse primer

<400> SEQUENCE: 18
tccaacattt atccgagcac ag                                              22

<210> SEQ ID NO 19
<211> LENGTH: 21
<212> TYPE: DNA
<213> ORGANISM: Artificial Sequence
<220> FEATURE:
<223> OTHER INFORMATION: Synthetic Lin28a forward primer

<400> SEQUENCE: 19
ccgcagttgt agcacctgtc t                                               21

<210> SEQ ID NO 20
<211> LENGTH: 22
<212> TYPE: DNA
<213> ORGANISM: Artificial Sequence
<220> FEATURE:
<223> OTHER INFORMATION: Synthetic Lin28a reverse primer

<400> SEQUENCE: 20
gaagaacatg cagaagcgaa ga                                              22

<210> SEQ ID NO 21
<211> LENGTH: 21
<212> TYPE: DNA
<213> ORGANISM: Artificial Sequence
<220> FEATURE:
<223> OTHER INFORMATION: Synthetic Dppa2 forward primer

<400> SEQUENCE: 21
gcgtagcgta gtctgtgttt g                                               21

<210> SEQ ID NO 22
<211> LENGTH: 22
<212> TYPE: DNA
<213> ORGANISM: Artificial Sequence
<220> FEATURE:
<223> OTHER INFORMATION: Synthetic Dppa2 reverse primer

<400> SEQUENCE: 22
tcaacgagaa ccaatctgag ga                                              22

<210> SEQ ID NO 23
<211> LENGTH: 21
<212> TYPE: DNA
<213> ORGANISM: Artificial Sequence
<220> FEATURE:
<223> OTHER INFORMATION: Synthetic Nanog forward primer

<400> SEQUENCE: 23
agttatggag cggagcagca t                                               21

<210> SEQ ID NO 24
<211> LENGTH: 18
<212> TYPE: DNA
<213> ORGANISM: Artificial Sequence
<220> FEATURE:
<223> OTHER INFORMATION: Synthetic Nanog reverse primer

<400> SEQUENCE: 24
aggcctggac cgctcagt                                                   18

<210> SEQ ID NO 25
<211> LENGTH: 23

```
<212> TYPE: DNA
<213> ORGANISM: Artificial Sequence
<220> FEATURE:
<223> OTHER INFORMATION: Synthetic Actb forward primer

<400> SEQUENCE: 25
cattgctgac aggatgcaga agg                                              23

<210> SEQ ID NO 26
<211> LENGTH: 22
<212> TYPE: DNA
<213> ORGANISM: Artificial Sequence
<220> FEATURE:
<223> OTHER INFORMATION: Synthetic Actb reverse primer

<400> SEQUENCE: 26
tgctggaagg tggacagtga gg                                               22

<210> SEQ ID NO 27
<211> LENGTH: 23
<212> TYPE: DNA
<213> ORGANISM: Artificial Sequence
<220> FEATURE:
<223> OTHER INFORMATION: Synthetic Gadph forward primer

<400> SEQUENCE: 27
catcactgcc acccagaaga ctg                                              23

<210> SEQ ID NO 28
<211> LENGTH: 23
<212> TYPE: DNA
<213> ORGANISM: Artificial Sequence
<220> FEATURE:
<223> OTHER INFORMATION: Synthetic Gadph reverse primer

<400> SEQUENCE: 28
atgccagtga gcttcccgtt cag                                              23

<210> SEQ ID NO 29
<211> LENGTH: 18
<212> TYPE: DNA
<213> ORGANISM: Artificial Sequence
<220> FEATURE:
<223> OTHER INFORMATION: Synthetic pLL-Oct4 forward primer

<400> SEQUENCE: 29
gaaggatgtg gtccgagt                                                    18

<210> SEQ ID NO 30
<211> LENGTH: 20
<212> TYPE: DNA
<213> ORGANISM: Artificial Sequence
<220> FEATURE:
<223> OTHER INFORMATION: Synthetic pLL-Oct4 reverse primer

<400> SEQUENCE: 30
gcagcgtatc cacatagcgt                                                  20

<210> SEQ ID NO 31
<211> LENGTH: 18
<212> TYPE: DNA
<213> ORGANISM: Artificial Sequence
<220> FEATURE:
<223> OTHER INFORMATION: Synthetic pLL-Sox2 forward primer

<400> SEQUENCE: 31
```
catgggttcg gtggtcaa                                          18

<210> SEQ ID NO 32
<211> LENGTH: 20
<212> TYPE: DNA
<213> ORGANISM: Artificial Sequence
<220> FEATURE:
<223> OTHER INFORMATION: Synthetic pLL-Sox2 reverse primer

<400> SEQUENCE: 32
gcagcgtatc cacatagcgt                                        20

<210> SEQ ID NO 33
<211> LENGTH: 18
<212> TYPE: DNA
<213> ORGANISM: Artificial Sequence
<220> FEATURE:
<223> OTHER INFORMATION: Synthetic pLL-Klf4 forward primer

<400> SEQUENCE: 33
accactgtga ctgggacg                                          18

<210> SEQ ID NO 34
<211> LENGTH: 20
<212> TYPE: DNA
<213> ORGANISM: Artificial Sequence
<220> FEATURE:
<223> OTHER INFORMATION: Synthetic pLL-Klf4 reverse primer

<400> SEQUENCE: 34
gcagcgtatc cacatagcgt                                        20

<210> SEQ ID NO 35
<211> LENGTH: 20
<212> TYPE: DNA
<213> ORGANISM: Artificial Sequence
<220> FEATURE:
<223> OTHER INFORMATION: Synthetic pLL-cMyc forward primer

<400> SEQUENCE: 35
tacatcctgt ccgtccaagc                                        20

<210> SEQ ID NO 36
<211> LENGTH: 20
<212> TYPE: DNA
<213> ORGANISM: Artificial Sequence
<220> FEATURE:
<223> OTHER INFORMATION: Synthetic pLL-cMyc reverse primer

<400> SEQUENCE: 36
gcagcgtatc cacatagcgt                                        20

<210> SEQ ID NO 37
<211> LENGTH: 19
<212> TYPE: DNA
<213> ORGANISM: Artificial Sequence
<220> FEATURE:
<223> OTHER INFORMATION: Synthetic Fu-tet-hOct4 forward primer

<400> SEQUENCE: 37
acctccatag aagacaccg                                         19

<210> SEQ ID NO 38
<211> LENGTH: 18
<212> TYPE: DNA
<213> ORGANISM: Artificial Sequence

```
<220> FEATURE:
<223> OTHER INFORMATION: Synthetic Fu-tet-hOct4 reverse primer

<400> SEQUENCE: 38
tagccccact ccaacctg                                                   18

<210> SEQ ID NO 39
<211> LENGTH: 19
<212> TYPE: DNA
<213> ORGANISM: Artificial Sequence
<220> FEATURE:
<223> OTHER INFORMATION: Synthetic Fu-tet-hSox2 forward primer

<400> SEQUENCE: 39
acctccatag aagacaccg                                                  19

<210> SEQ ID NO 40
<211> LENGTH: 22
<212> TYPE: DNA
<213> ORGANISM: Artificial Sequence
<220> FEATURE:
<223> OTHER INFORMATION: Synthetic Fu-tet-hSox2 reverse primer

<400> SEQUENCE: 40
ctccgacaaa agtttccact cg                                              22

<210> SEQ ID NO 41
<211> LENGTH: 19
<212> TYPE: DNA
<213> ORGANISM: Artificial Sequence
<220> FEATURE:
<223> OTHER INFORMATION: Synthetic Fu-tet-hKlf4 forward primer

<400> SEQUENCE: 41
acctccatag aagacaccg                                                  19

<210> SEQ ID NO 42
<211> LENGTH: 18
<212> TYPE: DNA
<213> ORGANISM: Artificial Sequence
<220> FEATURE:
<223> OTHER INFORMATION: Synthetic Fu-tet-hKlf4 reverse primer

<400> SEQUENCE: 42
gaagaggagg ctgacgct                                                   18

<210> SEQ ID NO 43
<211> LENGTH: 19
<212> TYPE: DNA
<213> ORGANISM: Artificial Sequence
<220> FEATURE:
<223> OTHER INFORMATION: Synthetic hcMyc forward primer

<400> SEQUENCE: 43
acctccatag aagacaccg                                                  19

<210> SEQ ID NO 44
<211> LENGTH: 18
<212> TYPE: DNA
<213> ORGANISM: Artificial Sequence
<220> FEATURE:
<223> OTHER INFORMATION: Synthetic hcMyc reverse primer

<400> SEQUENCE: 44
gggtcgcaga tgaaactc                                                   18
```

```
<210> SEQ ID NO 45
<211> LENGTH: 22
<212> TYPE: DNA
<213> ORGANISM: Artificial Sequence
<220> FEATURE:
<223> OTHER INFORMATION: Synthetic Oct4 forward primer

<400> SEQUENCE: 45
ggagtggttt tagaaataat tg                                              22

<210> SEQ ID NO 46
<211> LENGTH: 23
<212> TYPE: DNA
<213> ORGANISM: Artificial Sequence
<220> FEATURE:
<223> OTHER INFORMATION: Synthetic Oct4 reverse primer

<400> SEQUENCE: 46
tccaaccctA ctaacccatc acc                                             23

<210> SEQ ID NO 47
<211> LENGTH: 30
<212> TYPE: DNA
<213> ORGANISM: Artificial Sequence
<220> FEATURE:
<223> OTHER INFORMATION: Synthetic Nanog forward primer

<400> SEQUENCE: 47
gattttgtag gtgggattaa ttgtgaattt                                      30

<210> SEQ ID NO 48
<211> LENGTH: 30
<212> TYPE: DNA
<213> ORGANISM: Artificial Sequence
<220> FEATURE:
<223> OTHER INFORMATION: Synthetic Nanog reverse primer

<400> SEQUENCE: 48
accaaaaaaa cccacactca tatcaatata                                      30

<210> SEQ ID NO 49
<211> LENGTH: 20
<212> TYPE: DNA
<213> ORGANISM: Artificial Sequence
<220> FEATURE:
<223> OTHER INFORMATION: Synthetic Oct4 forward primer

<400> SEQUENCE: 49
ctgtaaggac aggccgagag                                                 20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oct4 reverse primer

<400> SEQUENCE: 50
caggaggcct tcattttcaa                                                 20

<210> SEQ ID NO 51
<211> LENGTH: 19
<212> TYPE: DNA
<213> ORGANISM: Artificial Sequence
<220> FEATURE:
<223> OTHER INFORMATION: Synthetic Nanog forward primer
```

<400> SEQUENCE: 51
ctatcgcctt gagccgttg                                                    19

<210> SEQ ID NO 52
<211> LENGTH: 26
<212> TYPE: DNA
<213> ORGANISM: Artificial Sequence
<220> FEATURE:
<223> OTHER INFORMATION: Synthetic Nanog reverse primer

<400> SEQUENCE: 52
aactcagtgt ctagaaggaa agatca                                            26

<210> SEQ ID NO 53
<211> LENGTH: 21
<212> TYPE: DNA
<213> ORGANISM: Artificial Sequence
<220> FEATURE:
<223> OTHER INFORMATION: Synthetic Sox2 forward primer

<400> SEQUENCE: 53
tttattcagt tcccagtcca a                                                 21

<210> SEQ ID NO 54
<211> LENGTH: 22
<212> TYPE: DNA
<213> ORGANISM: Artificial Sequence
<220> FEATURE:
<223> OTHER INFORMATION: Synthetic Sox2 reverse primer

<400> SEQUENCE: 54
ttattcctat gtgtgagcaa ga                                                22

<210> SEQ ID NO 55
<211> LENGTH: 19
<212> TYPE: DNA
<213> ORGANISM: Artificial Sequence
<220> FEATURE:
<223> OTHER INFORMATION: Synthetic OG forward primer

<400> SEQUENCE: 55
aaccactacc tgagcaccc                                                    19

<210> SEQ ID NO 56
<211> LENGTH: 20
<212> TYPE: DNA
<213> ORGANISM: Artificial Sequence
<220> FEATURE:
<223> OTHER INFORMATION: Synthetic OG reverse primer

<400> SEQUENCE: 56
acctctacaa atgtggtatg                                                   20

<210> SEQ ID NO 57
<211> LENGTH: 58
<212> TYPE: DNA
<213> ORGANISM: Artificial Sequence
<220> FEATURE:
<223> OTHER INFORMATION: SALL4 shRNA

<400> SEQUENCE: 57
ccggcagccc acctttgtca aagttctcga gaactttgac aaaggtgggc tgtttttg         58

<210> SEQ ID NO 58

```
<211> LENGTH: 58
<212> TYPE: DNA
<213> ORGANISM: Artificial Sequence
<220> FEATURE:
<223> OTHER INFORMATION: SALL4 shRNA

<400> SEQUENCE: 58
ccgggcccac ctttgtcaaa gttgactcga gtcaactttg acaaggtgg gcttttttg        58

<210> SEQ ID NO 59
<211> LENGTH: 58
<212> TYPE: DNA
<213> ORGANISM: Artificial Sequence
<220> FEATURE:
<223> OTHER INFORMATION: Gata4 shRNA

<400> SEQUENCE: 59
ccggagccca agaacctgaa taaatctcga gatttattca ggttcttggg cttttttg        58

<210> SEQ ID NO 60
<211> LENGTH: 58
<212> TYPE: DNA
<213> ORGANISM: Artificial Sequence
<220> FEATURE:
<223> OTHER INFORMATION: Gata4 shRNA

<400> SEQUENCE: 60
ccggcatctc ctgtcactca gacatctcga gatgtctgag tgacaggaga tgttttttg        58

<210> SEQ ID NO 61
<211> LENGTH: 58
<212> TYPE: DNA
<213> ORGANISM: Artificial Sequence
<220> FEATURE:
<223> OTHER INFORMATION: Gata6 shRNA

<400> SEQUENCE: 61
ccggccacta ccttatggcg tagaactcga gttctacgcc ataaggtagt ggtttttg        58

<210> SEQ ID NO 62
<211> LENGTH: 58
<212> TYPE: DNA
<213> ORGANISM: Artificial Sequence
<220> FEATURE:
<223> OTHER INFORMATION: Gata6 shRNA

<400> SEQUENCE: 62
ccggcctcga ccacttgcta tgaaactcga gtttcatagc aagtggtcga ggtttttg        58

<210> SEQ ID NO 63
<211> LENGTH: 58
<212> TYPE: DNA
<213> ORGANISM: Artificial Sequence
<220> FEATURE:
<223> OTHER INFORMATION: Sox17 shRNA

<400> SEQUENCE: 63
ccggcccaca atcactgtcc agtttctcga gaaactggac agtgattgtg ggtttttg        58

<210> SEQ ID NO 64
<211> LENGTH: 58
<212> TYPE: DNA
<213> ORGANISM: Artificial Sequence
<220> FEATURE:
<223> OTHER INFORMATION: Sox17 shRNA

<400> SEQUENCE: 64
```
ccggcgcacg gaattcgaac agtatctcga gatactgttc gaattccgtg cgtttttg        58

<210> SEQ ID NO 65
<211> LENGTH: 58
<212> TYPE: DNA
<213> ORGANISM: Artificial Sequence
<220> FEATURE:
<223> OTHER INFORMATION: Ezh2 shRNA

<400> SEQUENCE: 65
ccgggctagg ctaattggga ccaaactcga gtttggtccc aattagccta gctttttg        58

<210> SEQ ID NO 66
<211> LENGTH: 58
<212> TYPE: DNA
<213> ORGANISM: Artificial Sequence
<220> FEATURE:
<223> OTHER INFORMATION: Ezh2 shRNA

<400> SEQUENCE: 66
ccggcggctc ctctaaccat gtttactcga gtaaacatgg ttagaggagc cgtttttg        58

<210> SEQ ID NO 67
<211> LENGTH: 57
<212> TYPE: DNA
<213> ORGANISM: Artificial Sequence
<220> FEATURE:
<223> OTHER INFORMATION: Control shRNA

<400> SEQUENCE: 67
ccggcaacaa gatgaagagc accaactcga gttggtgctc ttcatcttgt gtttttg         57

<210> SEQ ID NO 68
<211> LENGTH: 33
<212> TYPE: DNA
<213> ORGANISM: Artificial Sequence
<220> FEATURE:
<223> OTHER INFORMATION: SALL4 Primer for plasmid construction

<400> SEQUENCE: 68
tactcgaggc caccatgtcg aggcgcaagc agg                                   33

<210> SEQ ID NO 69
<211> LENGTH: 36
<212> TYPE: DNA
<213> ORGANISM: Artificial Sequence
<220> FEATURE:
<223> OTHER INFORMATION: SALL4 Primer for plasmid construction

<400> SEQUENCE: 69
gggaattcat cacaaagcag catagcaaca atcgtg                                36

<210> SEQ ID NO 70
<211> LENGTH: 37
<212> TYPE: DNA
<213> ORGANISM: Artificial Sequence
<220> FEATURE:
<223> OTHER INFORMATION: GATA4 Primer for plasmid construction

<400> SEQUENCE: 70
acctcgaggc caccatgtat cagagcttgg ccatggc                               37

<210> SEQ ID NO 71
<211> LENGTH: 36
<212> TYPE: DNA

```
<213> ORGANISM: Artificial Sequence
<220> FEATURE:
<223> OTHER INFORMATION: GATA4 Primer for plasmid construction

<400> SEQUENCE: 71
gcgaattcat cattacgcag tgattatgtc cccgtg                                36

<210> SEQ ID NO 72
<211> LENGTH: 34
<212> TYPE: DNA
<213> ORGANISM: Artificial Sequence
<220> FEATURE:
<223> OTHER INFORMATION: GATA6 Primer for plasmid construction

<400> SEQUENCE: 72
atctcgaggc caccatggcc ttgactgacg gcgg                                  34

<210> SEQ ID NO 73
<211> LENGTH: 34
<212> TYPE: DNA
<213> ORGANISM: Artificial Sequence
<220> FEATURE:
<223> OTHER INFORMATION: GATA6 Primer 2 for plasmid construction

<400> SEQUENCE: 73
atctcgaggc caccatggcc ttgactgacg gcgg                                  34
```